US007078493B1

(12) United States Patent
Greene et al.

(10) Patent No.: US 7,078,493 B1
(45) Date of Patent: Jul. 18, 2006

(54) ANTIBODIES TO HUMAN TUMOR NECROSIS FACTOR RECEPTOR-LIKE GENES

(75) Inventors: John M. Greene, Gaithersburg, MD (US); Robert D. Fleischmann, Gaithersburg, MD (US); Jian Ni, Rockville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/526,437

(22) Filed: Mar. 15, 2000

Related U.S. Application Data

(63) Continuation-in-part of application No. 08/718,737, filed on Sep. 18, 1996, which is a continuation-in-part of application No. 08/469,637, filed on Jun. 6, 1995, which is a continuation of application No. PCT/US95/03216, filed on Mar. 15, 1995.

(60) Provisional application No. 60/136,248, filed on May 26, 1999, provisional application No. 60/124,489, filed on Mar. 15, 1999.

(51) Int. Cl.
*C07K 16/00* (2006.01)
*G01N 33/53* (2006.01)

(52) U.S. Cl. .............................. 530/389.2; 530/387.1; 530/388.1; 530/388.15; 530/389.1; 435/7.1

(58) Field of Classification Search ................ 530/350, 530/351, 387.1, 387.3, 387.9, 388.1, 388.15, 530/389.1, 389.2
See application file for complete search history.

(56) References Cited

U.S. PATENT DOCUMENTS

| 5,395,760 | A  | 3/1995  | Smith et al. | ............. 435/240.1 |
| 5,464,938 | A  | 11/1995 | Smith et al. | ................. 530/350 |
| 5,712,155 | A  | 1/1998  | Smith et al. | ............. 435/320.1 |
| 5,741,899 | A  | 4/1998  | Capon et al. | .............. 536/23.4 |
| 6,015,938 | A  | 1/2000  | Boyle et al. | .................. 800/18 |
| 6,284,485 | B1 | 9/2001  | Boyle et al. | ............... 435/69.1 |
| 6,284,728 | B1 | 9/2001  | Boyle et al. | .................. 514/12 |
| 6,284,740 | B1 | 9/2001  | Boyle et al. | .................. 514/44 |
| 6,288,032 | B1 | 9/2001  | Boyle et al. | .................. 514/12 |
| 6,369,027 | B1 | 4/2002  | Boyle et al. | .................... 514/2 |

FOREIGN PATENT DOCUMENTS

| EP | 0 585 939   | 3/1994  |
| EP | 0 816 380   | 1/1998  |
| EP | 0 816 380 A | 1/1998  |
| EP | 0 897 114   | 2/1999  |
| WO | WO 91/09045 | 6/1991  |
| WO | WO 94/09137 | 4/1994  |
| WO | WO 94/13808 | 6/1994  |
| WO | WO 96/26217 | 8/1996  |
| WO | WO 96/26217 A | 8/1996 |
| WO | WO 96/28546 | 9/1996  |
| WO | WO 96/28546 A | 9/1996 |
| WO | WO 98/48051 | 10/1998 |

OTHER PUBLICATIONS

Kohno, T. et al., "A second tumor necrosis factor receptor gene product can shed a naturally occurring tumor necrosis factor inhibitor," *Proc. Natl. Acad. Sci. USA* 87:8331-8335 (1990).

Schall, T.J. et al., "Molecular Cloning and Expression of a Receptor for Human Tumor Necrosis Factor," *Cell* 61:361-370 (1990).

Aruffo, A.A. et al., Database A-Geneseq24 on MASPAR, Accession No. R38859 (1993).

Aggarwal, B. B. and K. Natarajan, "Tumor necrosis factors: Developments during the last decade," *Eur. Cytokine Netw.* 7(2):93-124 (Apr.-Jun. 1996).

Aslanidis, C., Database EMBL-new3 on MASPAR, Accession No. X75491 (Mar. 1994).

Beutler, B. et al., "Unraveling function in the TNF ligand and receptor families," *Science* 264:667-668 (1994).

Bowie, J.U. et al., "Deciphering the message in protein sequences: tolerance to amino acid substitutions," *Science* 247:1306-1310 (1990).

Camerini, D. et al., "The T Cell Activation Antigen CD27 Is a Member of the Nerve Growth Factor/Tumor Necrosis Factor Receptor Gene Family," *J. Immunol.* 147(9):3165-3169 (1991).

Chinnaiyan, A.M. et al., "Signal Transduction by DR3, a Death Domain-Containing Receptor Related to TNFR-1 and CD95," *Science* 274:990-992 (1996).

Crowe, P.D. et al., "A lymphotoxin-beta-specific receptor," *Science* 264:707-710 (1994).

Dürkop, H. et al., "Molecular Cloning and Expression of a New Member of the Nerve Growth Factor Receptor Family That Is Characteristic for Hodgkin's Disease," *Cell* 68:421-427 (1992).

Engelmann, H. et al., "Two Tumor Necrosis Factor-Binding Proteins Purified from Human Urine. Evidence for Immunological Cross-Reactivity with Cell Surface Tumor Necrosis Factor Receptors," *J. Biol. Chem.* 265(3):1531-1536 (1990).

(Continued)

*Primary Examiner*—Robert S. Landsman
*Assistant Examiner*—Seharaseyon Jegatheesan
(74) *Attorney, Agent, or Firm*—Human Genome Sciences, Inc.

(57) ABSTRACT

The present inventors have discovered novel receptors in the Tumor Necrosis Factor (TNF) receptor family. In particular, receptors having homology to the type 2 TNF receptor (TNF-RII) are provided. Isolated nucleic acid molecules are also provided encoding the novel receptors of the present invention. Receptor polypeptides are further provided as are vectors, host cells and recombinant methods for producing the same.

32 Claims, 11 Drawing Sheets

OTHER PUBLICATIONS

Feinstein, E. et al., "The death domain: a module shared by proteins with diverse cellular functions," *TIBS 20*:342-344 (Sep. 1995).

Genexpress, Database EMBL/GenBank/DDBJ on MASPAR, Accession No. Z38433 (Oct. 1994).

George, et al., in *Macromolecular Sequencing and Synthesis*, Schlessinger, D.H., ed., Alan R. Liss, Inc., New York, pp. 127-149 (1988).

Glasgow, E. and Schechter, N., Database EMBL-new3 on MASPAR, Accession No. L23876 (1993).

Hillier, L. et al., Database EST-STS on MASPAR, Accession No. H14106 (Jul. 1995).

Himmler, A. et al., "Molecular Cloning and Expression of Human and Rat Tumor Necrosis Factor Receptor Chain (p60) and Its Soluble Derivative, Tumor Necrosis Factor-Binding Protein," *DNA and Cell Biol. 9*(10):705-715 (1990).

Hohmann, H.-P. et al., "Two Different Cell Types Have Different Major Receptors for Human Tumor Necrosis Factor (TNFα)" *J. Biol. Chem. 264*(25):14927-14934 (1989).

Hsu, K. C. and M. V. Chao, "Differential Expression and Ligand Binding Properties of Tumor Necrosis Factor Receptor Chimeric Mutants," *J. Biol. Chem. 268*(22):16430-16436 (1993).

Hudson, T., Database EST-STS on MASPAR, Accession No. G11923 (Oct. 1995).

Itoh, N. et al., "The Polypeptide Encoded by the cDNA for Human Cell Surface Antigen Fas Can Mediate Apoptosis," *Cell 66*:233-243 (1991).

Johnson, D. et al., "Expression and Structure of the Human NGF Receptor," *Cell 47*:545-554 (1986).

Lewis, M. et al., "Cloning and expression of cDNAs for two distinct murine tumor necrosis factor receptors demonstrate one receptor is species specific," *Proc. Natl. Acad. Sci. USA 88*:2830-2834 (1991).

Loetscher, H. et al., "Molecular Cloning and Expression of the Human 55 kd Tumor Necrosis Factor Receptor," *Cell 61*:351-359 (1990).

Mallett, S. et al., "Characterization of the MRC 0X40 antigen of activated CD4 positive T lymphocytes—a molecule related to nerve growth factor receptor ," *EMBO J. 9*(4):1063-1068 (1990).

Muzio, M. et al., "FLICE, A Novel FADD-Homologous ICE/CED-3-like Protease, Is Recruited to the CD95 (Fas/APO-1) Death-Inducing Signaling Complex," *Cell 85*:817-827 (1996).

NCBI Entrez, GenBank Report, Accession No. D62967, from Fujiwara, T. et al. (Aug. 1995).

NCBI Entrez, GenBank Report, Accession No. D63118, from Fujiwara, T. et al. (Aug. 1995).

NCBI Entrez, GenBank Report, Accession No. D63125, from Fujiwara, T. et al. (Aug. 1995).

NCBI Entrez, GenBank Report, Accession No. D63126, from Fujiwara, T. et al. (Aug. 1995).

NCBI Entrez, GenBank Report, Accession No. AA296905, from Adams, MD. et al. (Sep. 1995).

NCBI Entrez, GenBank Report, Accession No. AA296908, from Adams, M.D. et al. (Sep. 1995).

NCBI Entrez, GenBank Report, Accession No. 298429, from Adams, M.D. et al. (Sep. 1995).

NCBI Entrez, GenBank Report, Accession No. H88769, from Hillier, L. et al. (Nov. 1995).

NCBI Entrez, GenBank Report, Accession No. C02463, from Okubo, K. et al. (Jul. 1996).

NCBI Entrez, GenBank Report, Accession No. AA037313, from Hillier, L. et al. (Nov. 1996).

NCBI Entrez, GenBank Report, Accession No. AA195113, from Hillier, L. et al. (May 1997).

NCBI Entrez, GenBank Report, Accession No. AA233719, from Hillier, L. et al. (Aug. 1997).

NCBI Entrez, GenBank Report, Accession No. AA706996, from Hillier, L. et al. (Dec. 1997).

NCBI Entrez, GenBank Report, Accession No. AA599841, from Jia, L. et al. (Mar. 1998).

Nophar, Y. et al., "Soluble forms of tumor necrosis factor receptors (TNF-Rs). The cDNA for the type I TNF-R, cloned using amino acid sequence data of its soluble form, encodes both the cell surface and a soluble form of the receptor," *EMBO J. 9*(10):3269-3278 (1990).

Pfeffer, K. et al., "Mice Deficient for the 55 kd Tumor Necrosis Factor Receptor Are Resistant to Endotoxic Shock, yet Succumb to L. monocytogenes Infection," *Cell 73*:457-467 (1993).

Piguet, P. F. et al., "Evolution of collagen arthritis in mice is arrested by treatment with anti-tumour necrosis factor (TNF) antibody or a recombinant soluble TNF receptor," *Immunol. 77*:510-514 (1992).

Radeke, M. J. et al., "Gene transfer and molecular cloning of the rat nerve growth factor receptor," *Nature 325*:593-597 (1987).

Salgaller, M.L. et al., "Generation of specific anti-melanoma reactivity by stimulation of human tumor-infiltrating lymphocytes with MAGE-1 synthetic peptide," *Cancer Immunol. Immunother. 39*:105-116 (1994).

Smith, C.A. et al., "A receptor for tumor necrosis factor defines an unusual family of cellular and viral proteins," *Science 248*:1019-1023 (1990).

Smith, C. A. et al., "T2 Open Reading Frame from the Shope Fibroma Virus Encodes a Soluble Form of the TNF Receptor," *Biochem. Biophys. Res. Comm. 176*(1):335-342 (1991).

Stamenkovic, I. et al., "A B-lymphocyte activation molecule related to the nerve growth factor receptor and induced by cytokines in carcinomas," *EMBO J. 8*(5):1403-1410 (1989).

Van Ostade, X. et al., "Human tumor necrosis factor mutants with preferential binding to and activity on either the R55 or R75 receptor," *Eur. J. Biochem. 220*(3):771-779 (Mar. 1994).

Zauner, W. et al., Database EMBL-new3 on MASPAR, Accession No. X60370, X60371, X60550 (1992).

International Search Report issued by the International Searching Authority for Appl. No. PCT/US96/15003, mailed Jan. 21, 1997.

International Search Report issued by the International Searching Authority for Appl. No. PCT/US96/16849, mailed Mar. 26, 1997.

International Search Report issued by the International Searching Authority for Appl. No. PCT/US96/18540, mailed Mar. 18, 1997.

Dialog File 351, WPI Accession No. 96-402320, Derwent WPI English Language Abstract for WO 96/26217.

Kwon et al. "TR1, a new member of the tumor necrosis factor receptor superfamily, induces fibroblast proliferation and inhibits osteoclastogenesis and bone resorption" FASEB Journal 12(10):845-854 (1998).

Simonet et al. "Osteoprotegerin: A novel secreted protein involved in the regulation of bone density" Cell 89(2):309-319 (1997).

Tsuda et al. "Isolation of a novel cytokine from human fibroblasts that specifically inhibits osteoclastogenesis" Biochemical and Biophysical Res. Comms. 234(1):137-142 (1997).

Supplementary Partial European Search Report, Application No. 96 93 5862, dated Jan. 13, 2003.

```
              10                    30                    50
CGCCCAGCCGCCGCCTCCAAGCCCCTGAGGTTTCCGGGGACCACAATGAACAAGTTGCTG
                                                 M  N  K  L  L
              70                    90                   110
TGCTGCGCGCTCGTGTTTCTGGACATCTCCATTAAGTGGACCACCCAGGAAACGTTTCCT
 C  C  A  L  V  F  L  D  I  S  I  K  W  T  T  Q  E  T  F  P
             130                   150                   170
CCAAAGTACCTTCATTATGACGAAGAAACCTCTCATCAGCTGTTGTGTGACAAATGTCCT
 P  K  Y  L  H  Y  D  E  E  T  S  H  Q  L  L  C  D  K  C  P
             190                   210                   230
CCTGGTACCTACCTAAAACAACACTGTACAGCAAAGTGGAAGACCGTGTGCGCCCCTTGC
 P  G  T  Y  L  K  Q  H  C  T  A  K  W  K  T  V  C  A  P  C
             250                   270                   290
CCTGACCACTACTACACAGACAGCTGGCACACCAGTGACGAGTGTCTATACTGCAGCCCC
 P  D  H  Y  Y  T  D  S  W  H  T  S  D  E  C  L  Y  C  S  P
             310                   330                   350
GTGTGCAAGGAGCTGCAGTACGTCAAGCAGGAGTGCAATCGCACCCACAACCGCGTGTGC
 V  C  K  E  L  Q  Y  V  K  Q  E  C  N  R  T  H  N  R  V  C
             370                   390                   410
GAATGCAAGGAAGGGCGCTACCTTGAGATAGAGTTCTGCTTGAAACATAGGAGCTGCCCT
 E  C  K  E  G  R  Y  L  E  I  E  F  C  L  K  H  R  S  C  P
             430                   450                   470
CCTGGATTTGGAGTGGTGCAAGCTGGAACCCCAGAGCGAAATACAGTTTGCAAAAGATGT
 P  G  F  G  V  V  Q  A  G  T  P  E  R  N  T  V  C  K  R  C
             490                   510                   530
CCAGATGGGTTCTTCTCAAATGAGACGTCATCTAAAGCACCCTGTAGAAAACACACAAAT
 P  D  G  F  F  S  N  E  T  S  S  K  A  P  C  R  K  H  T  N
             550                   570                   590
TGCAGTGTCTTTGGTCTCCTGCTAACTCAGAAAGGAAATGCAACACACGACAACATATGT
 C  S  V  F  G  L  L  L  T  Q  K  G  N  A  T  H  D  N  I  C
             610                   630                   650
TCCGGAAACAGTGAATCAACTCAAAAATGTGGAATAGATGTTACCCTGTGTGAGGAGGCA
 S  G  N  S  E  S  T  Q  K  C  G  I  D  V  T  L  C  E  E  A
             670                   690                   710
TTCTTCAGGTTTGCTGTTCCTACAAAGTTTACGCCTAACTGGCTTAGTGTCTTGGTAGAC
 F  F  R  F  A  V  P  T  K  F  T  P  N  W  L  S  V  L  V  D
             730                   750                   770
AATTTGCCTGGCACCAAAGTAAACGCAGAGAGTGTAGAGAGGATAAAACGGCAACACAGC
 N  L  P  G  T  K  V  N  A  E  S  V  E  R  I  K  R  Q  H  S
             790                   810                   830
TCACAAGAACAGACTTTCCAGCTGCTGAAGTTATGGAAACATCAAAACAAAGACCAAGAT
 S  Q  E  Q  T  F  Q  L  L  K  L  W  K  H  Q  N  K  D  Q  D
```

FIG. 1A

```
                850                  870                  890
ATAGTCAAGAAGATCATCCAAGATATTGACCTCTGTGAAAACAGCGTGCAGCGGCACATT
 I  V  K  K  I  I  Q  D  I  D  L  C  E  N  S  V  Q  R  H  I
                910                  930                  950
GGACATGCTAACCTCACCTTCGAGCAGCTTCGTAGCTTGATGGAAAGCTTACCGGGAAAG
 G  H  A  N  L  T  F  E  Q  L  R  S  L  M  E  S  L  P  G  K
                970                  990                 1010
AAAGTGGGAGCAGAAGACATTGAAAAAACAATAAAGGCATGCAAACCCAGTGACCAGATC
 K  V  G  A  E  D  I  E  K  T  I  K  A  C  K  P  S  D  Q  I
               1030                 1050                 1070
CTGAAGCTGCTCAGTTTGTGGCGAATAAAAAATGGCGACCAAGACACCTTGAAGGGCCTA
 L  K  L  L  S  L  W  R  I  K  N  G  D  Q  D  T  L  K  G  L
               1090                 1110                 1130
ATGCACGCACTAAAGCACTCAAAGACGTACCACTTTCCCAAAACTGTCACTCAGAGTCTA
```

FIG.1A1

```
M   H   A   L   K   H   S   K   T   Y   H   F   P   K   T   V   T   Q   S   L
        1150                    1170                    1190
AAGAAGACCATCAGGTTCCTTCACAGCTTCACAATGTACAAATTGTATCAGAAGTTATTT
K   K   T   I   R   F   L   H   S   F   T   M   Y   K   L   Y   Q   K   L   F
        1210                    1230                    1250
TTAGAAATGATAGGTAACCAGGTCCAATCAGTAAAAATAAGCTGCTTATAACTGGAAATG
L   E   M   I   G   N   Q   V   Q   S   V   K   I   S   C   L   *
        1270                    1290                    1310
GCCATTGAGCTGTTTCCTCACAATTGGCGAGATCCCATGGATGAGTAAACTGTTTCTCAG
        1330                    1350                    1370
GCACTTGAGGCTTTCAGTGATATCTTTCTCATTACCAGTGACTAATTTTGCCACAGGGTA
        1390                    1410                    1430
CTAAAAGAAACTATGATGTGGAGAAAGGACTAACATCTCCTCCAATAAACCCCAAATGGT
        1450                    1470                    1490
TAATCCAACTGTCAGATCTGGATCGTTATCTACTGACTATATTTTCCCTTATTACTGCTT
        1510
GCAGTAATTCAACTGGAAAAAAAAAAA
```

FIG. 1B

```
          10                    30                    50
ATGAACAAGTTGCTGTGCTGCCGCGCTCGTGTTTCTGGACATCTCCATTAAGTGGACCACC
 M  N  K  L  L  C  C  A  L  V  F  L  D  I  S  I  K  W  T  T
          70                    90                   110
CAGGAAACGTTTCCTCCAAAGTACCTTCATTATGACGAAGAAACCTCTCATCAGCTGTTG
 Q  E  T  F  P  P  K  Y  L  H  Y  D  E  E  T  S  H  Q  L  L
         130                   150                   170
TGTGACAAATGTCCTCCTGGTACCTACCTAAAACAACACTGTACAGCAAAGTGGAAGACC
 C  D  K  C  P  P  G  T  Y  L  K  Q  H  C  T  A  K  W  K  T
         190                   210                   230
GTGTGCGCCCCTTGCCCTGACCACTACTACACAGACAGCTGGCACACCAGTGACGAGTGT
 V  C  A  P  C  P  D  H  Y  Y  T  D  S  W  H  T  S  D  E  C
         250                   270                   290
CTATACTGCAGCCCCGTGTGCAAGGAGCTGCAGTACGTCAAGCAGGAGTGCAATCGCACC
 L  Y  C  S  P  V  C  K  E  L  Q  Y  V  K  Q  E  C  N  R  T
         310                   330                   350
CACAACCGCGTGTGCGAATGCAAGGAAGGGCGCTACCTTGAGATAGAGTTCTGCTTGAAA
 H  N  R  V  C  E  C  K  E  G  R  Y  L  E  I  E  F  C  L  K
         370                   390                   410
CATAGGAGCTGCCCTCCTGGATTTGGAGTGGTGCAAGCTGGAACCCCAGAGCGAAATACA
 H  R  S  C  P  P  G  F  G  V  V  Q  A  G  T  P  E  R  N  T
         430                   450                   470
GTTTGCAAAAGATGTCCAGATGGGTTCTTCTCAAATGAGACGTCATCTAAAGCACCCTGT
 V  C  K  R  C  P  D  G  F  F  S  N  E  T  S  S  K  A  P  C
         490                   510                   530
AGAAAACACACAAATTGCAGTGTCTTTGGTCTCCTGCTAACTCAGAAAGGAAATGCAACA
 R  K  H  T  N  C  S  V  F  G  L  L  L  T  Q  K  G  N  A  T
         550                   570                   590
CACGACAACATATGTTCCGGAAACAGTGAATCAACTCAAAAATGTGGAATAGATGTTACC
 H  D  N  I  C  S  G  N  S  E  S  T  Q  K  C  G  I  D  V  T
         610                   630                   650
CTGTGTGAGGAGGCATTCTTCAGGTTTGCTGTTCCTACAAAGTTTACGCCTAACTGGCTT
 L  C  E  E  A  F  F  R  F  A  V  P  T  K  F  T  P  N  W  L
         670                   690                   710
AGTGTCTTGGTAGACAATTTGCCTGGCACCAAAGTAAACGCAGAGAGTGTAGAGAGGATA
 S  V  L  V  D  N  L  P  G  T  K  V  N  A  E  S  V  E  R  I
         730                   750                   770
AAACGGCAACACAGCTCACAAGAACAGACTTTCCAGCTGCTGAAGTTATGGAAACATCAA
 K  R  Q  H  S  S  Q  E  Q  T  F  Q  L  L  K  L  W  K  H  Q
         790                   810                   830
AACAAAGACCAAGATATAGTCAAGAAGATCATCCAAGATATTGACCTCTGTGAAAACAGC
 N  K  D  Q  D  I  V  K  K  I  I  Q  D  I  D  L  C  E  N  S
```

FIG.2A

```
                850                  870                  890
GTGCAGCGGCACATTGGACATGCTAACCTCACCTTCGAGCAGCTTCGTAGCTTGATGGAA
 V  Q  R  H  I  G  H  A  N  L  T  F  E  Q  L  R  S  L  M  E
                910                  930                  950
AGCTTACCGGGAAAGAAAGTGGGAGCAGAAGACATTGAAAAAACAATAAAGGCATGCAAA
 S  L  P  G  K  K  V  G  A  E  D  I  E  K  T  I  K  A  C  K
                970                  990                 1010
CCCAGTGACCAGATCCTGAAGCTGCTCAGTTTGTGGCGAATAAAAAATGGCGACCAAGAC
 P  S  D  Q  I  L  K  L  L  S  L  W  R  I  K  N  G  D  Q  D
               1030                 1050                 1070
ACCTTGAAGGGCCTAATGCACGCACTAAAGCACTCAAAGACGTACCACTTTCCCAAAACT
 T  L  K  G  L  M  H  A  L  K  H  S  K  T  Y  H  F  P  K  T
               1090                 1110                 1130
GTCACTCAGAGTCTAAAGAAGACCATCAGGTTCCTTCACAGCTTCACAATGTACAAATTG
 V  T  Q  S  L  K  K  T  I  R  F  L  H  S  F  T  M  Y  K  L
               1150                 1170
```

FIG.2A1

```
TATCAGAAGTTATTTTTAGAAATGATAGGTAATCTAGAAAAGATCTAA
 Y  Q  K  L  F  L  E  M  I  G  N  L  E  K  I
```

FIG.2B

```
  1 .....MNKLLCCALVFLDISIKWTTQETFPP.........KYLHYDEETS  36
            |...|:::. . :..|.|.|         :.| ::|.
  1 MAPVAVWAALAVGLELWAAAHALPAQVAFTPYAPEPGSTCRLREYYDQTA  50

37 HQLLCDKCPPGTYLKQHCTAKWKTVCAPCPDHYYTDSWHTSDECLYCSPV  86
    |: |.||.|| . |  || ...|||..|.| ||: |: .||| |:.
 51 .QMCCSKCSPGQHAKVFCTKTSDTVCDSCEDSTYTQLWNWVPECLSCGSR  99

87 CKELQYVKQECNRTHNRVCECKEGRYLEIE.......FCLKHRSCPPGFGV 130
    |.. |  .|.|.|.:||:|.|:.|:| .:.       :| . |.|.|||||
100 CSSDQVETQACTREQNRICTCRPGWYCALSKQEGCRLCAPLRKCRPGFGV 149

131 VQAGTPERNTVCKRCPDGFFSNETSSKAPCRKHTNCSVFGLLLTQKGNAT 180
    ..:||....:|||.|:.| |||.|||.. ||.| |.|.::   .|||.
150 ARPGTETSDVVCKPCAPGTFSNTTSSTDICRPHQICNVVAI....PGNAS 195

181 HDNIC...................SGNSESTQKCGIDVTLCEEAFF... 207
    |..|                     |..|: ||... | ....|:
196 MDAVCTSTSPTRSMAPGAVHLPQPVSTRSQHTQPTPEPSTAPSTSFLLPM 245

208 ...........RFAVPTKFTPNWLSVLVDNLPGTKVNAESVERIKR.... 242
               ||:|. :... .:: | . ||. :...:|:
246 GPSPPAEGSTGDFALPVGLIVG..VTALGLLIIGVVNCVIMTQVKKKPLC 293

243 .QHSSQEQTFQLLKLWKHQNKDQDIV.....KKIIQDIDLCENSVQRHIG 286
    |:....  :. | : |...|: :    ..   .:: :....::|:.
294 LQREAKVPHLPADKARGTQGPEQQHLLITAPSSSSSSLESSASALDRRAP 343

287 HANLTFEQLRSLMESLPGK...KVGAEDIEKTIKACKPSDQILKLLSLWR 333
        | . | .::.|:|.   ..|.|        .:    ::  .
344 TRNQP..QAPGVEASGAGEARASTGSSDSSPGGHGTQVNVTCIVNVCSSS 391

334 IKNGDQDTLKGLMHALKHSKTYHFPKTVTQSLKKTIRFLHS.....FTMY 378
    ..:: .. :  :  ..|... .||.  ..:.|.  ::|        |:.
392 DHSSQCSSQASSTMGDTDSSPSESPKDEQVPFSKEECAFRSQLETPETLL 441

379 KLYQKLFLEMIGNQVQSVKISCL. 401
         :.  |.: |  . .::|'| |
442 GSTEEKPLPL.GVPDAGMKPS... 461
```

FIG.3

ANTIBODIES TO HUMAN TUMOR NECROSIS FACTOR RECEPTOR-LIKE GENES

CROSS-REFERENCE TO RELATED APPLICATIONS

This application claims the benefit of U.S. Provisional Application No. 60/136,248, filed May 26, 1999 and U.S. Provisional Application No. 60/124,489, filed Mar. 15, 1999. This application is also a continuation-in-part of U.S. patent application Ser. No. 08/718,737, filed Sep. 18, 1996, which was a continuation-in-part of U.S. patent application Ser. No. 08/469,637, filed Jun. 6, 1995, which was a continuation of PCT/US95/03216, filed Mar. 15, 1995. The content of all the aforesaid applications are relied upon and incorporated by reference in their entirety.

BACKGROUND OF THE INVENTION

1. Field of the Invention

The present inventors have discovered novel receptors in the Tumor Necrosis Factor (TNF) receptor family. In particular, receptors having homology to the type 2 TNF receptor (TNF-RII) are provided. Isolated nucleic acid molecules are also provided encoding the novel receptors of the present invention. Receptor polypeptides are further provided, as are vectors, host cells, and recombinant methods for producing the same.

2. Related Art

Human tumor necrosis factors α (TNF-α) and β (TNF-β or lymphotoxin) are related members of a broad class of polypeptide mediators, which includes the interferons, interleukins and growth factors, collectively called cytokines (Beutler, B. and Cerami, A., *Annu. Rev. Immunol.* 7:625–655 (1989)).

Tumor necrosis factor (TNF-α and TNF-β) was originally discovered as a result of its anti-tumor activity, however, now it is recognized as a pleiotropic cytokine playing important roles in a host of biological processes and pathologies. To date, there are ten known members of the TNF-related cytokine family, TNF-α, TNF-β (lymphotoxin-α), LT-β, TRAIL and ligands for the Fas receptor, CD30, CD27, CD40, OX40 and 4-1BB receptors. These proteins have conserved C-terminal sequences and variable N-terminal sequences which are often used as membrane anchors, with the exception of TNF-β. Both TNF-α and TNF-β function as homotrimers when they bind to TNF receptors.

TNF is produced by a number of cell types, including monocytes, fibroblasts, T-cells, natural killer (NK) cells and predominately by activated macrophages. TNF-α has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al., *J. Immunol.* 136:2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

TNF-β has many activities, including induction of an antiviral state and tumor necrosis, activation of polymorphonuclear leukocytes, induction of class I major histocompatibility complex antigens on endothelial cells, induction of adhesion molecules on endothelium and growth hormone stimulation (Ruddle, N. and Homer, R., *Prog. Allergy,* 40:162–182 (1988)).

Recent studies with "knockout" mice have shown that mice deficient in TNF-β production show abnormal development of the peripheral lymphoid organs and morphological changes in spleen architecture (reviewed in Aggarwal et al., *Eur Cytokine Netw,* 7(2):93–124 (1996)). With respect to the lymphoid organs, the popliteal, inguinal, para-aortic, mesenteric, axillary and cervical lymph nodes failed to develop in TNF-β-/-mice. In addition, peripheral blood from TNF-β-/-mice contained a three fold reduction in white blood cells as compared to normal mice. Peripheral blood from TNF-β-/-mice, however, contained four fold more B cells as compared to their normal counterparts. Further, TNF-β, in contrast to TNF-α has been shown to induce proliferation of EBV-infected B cells. These results indicate that TNF-β is involved in lymphocyte development.

The first step in the induction of the various cellular responses mediated by TNF or LT is their binding to specific cell surface or soluble receptors. Two distinct TNF receptors of approximately 55-KDa (TNF-RI) and 75-KDa (TNF-RII) have been identified (Hohman et al., *J. Biol. Chem.,* 264: 14927–14934 (1989)), and human and mouse cDNAs corresponding to both receptor types have been isolated and characterized (Loetscher et al., *Cell,* 61:351 (1990)). Both TNF-Rs share the typical structure of cell surface receptors including extracellular, transmembrane and intracellular regions.

These molecules exist not only in cell bound forms, but also in soluble forms, consisting of the cleaved extra-cellular domains of the intact receptors (Nophar et al., *EMBO. Journal,* 9 (10):3269–76 (1990)) and otherwise intact receptors wherein the transmembrane domain is lacking. The extracellular domains of TNF-RI and TNF-RII share 28% identity and are characterized by four repeated cysteine-rich motifs with significant intersubunit sequence homology. The majority of cell types and tissues appear to express both TNF receptors and both receptors are active in signal transduction, however, they are able to mediate distinct cellular responses. Further, TNF-RII was shown to exclusively mediate human T-cell proliferation by TNF as shown in PCT WO 94/09137.

TNF-RI dependent responses include accumulation of C-FOS, IL-6, and manganese superoxide dismutase mRNA, prostaglandin E2 synthesis, IL-2 receptor and MHC class I and II cell surface antigen expression, growth inhibition, and cytotoxicity. TNF-RI also triggers second messenger systems such as phospholipase $A_2$, protein kinase C, phosphatidylcholine-specific phospholipase C and sphingomyelinase (Pfeffer, K et al., *Cell,* 73:457–467 (1993)).

Several interferons and other agents have been shown to regulate the expression of TNF-Rs. Retinoic acid, for example, has been shown to induce the production of TNF receptors in some cells type while down regulating production in other cells. In addition, TNF-α has been shown affect the localization of both types of receptor. TNF-α induces internalization of TNF-RI and secretion of TNF-RII (reviewed in Aggarwal et al., supra). Thus, the production and localization of both TNF-Rs are regulated by a variety of agents.

The yeast two hybrid system has been used to identify ligands which associate with both types of the TNF-Rs (reviewed in Aggarwal et al., supra). Several proteins have been identified which interact with the cytoplasmic domain of a murine TNF-R. Two of these proteins appear to be related to the baculovirus inhibitor of apoptosis, suggesting a direct role for TNF-R in the regulation of programmed cell death.

SUMMARY OF THE INVENTION

The novel Tumor Necrosis Factor (TNF) family receptors of the present invention are referred to herein as "TR1 receptors." Thus, in accordance with one aspect of the present invention, there are provided isolated nucleic acid molecules encoding the TR1 polypeptides of the present invention, including mRNAs, DNAs, cDNAs, genomic DNA as well as antisense analogs thereof and biologically active and diagnostically or therapeutically useful fragments thereof.

The isolated nucleic acid molecules of the present invention comprise, or alternatively consist of, polynucleotide molecules encoding the native TR1 receptor polypeptide having the amino acid sequence shown in FIG. 1 (SEQ ID NO:2) or the amino acid sequence encoded by the cDNA clone deposited in a bacterial host as ATCC Deposit Number 75899 on Sep. 29, 1994. The nucleotide sequence determined by sequencing the deposited native TR1 receptor clone, which is shown in FIG. 1 (SEQ ID NO: 1), contains an open reading frame encoding a polypeptide of 401 amino acid residues, including an initiation codon at positions 46–48 in FIG. 1, with a leader sequence of about 21 amino acid residues, and a predicted molecular weight of about 46 kDa for the whole protein and about 44 kDa for the non-glycosylated mature protein. The amino acid sequence of the predicted mature native TR1 receptor protein is shown in FIG. 1, amino acid residues about 22 to about 401 (SEQ ID NO:2).

Also included in the present invention are isolated nucleic acid molecules comprising, or alternatively consisting of, a polynucleotide encoding a carboxy terminus modified TR1 receptor polypeptide having the amino acid sequence shown in FIG. 2 (SEQ ID NO:4). The nucleotide sequence encoding a carboxy terminus modified TR1 receptor polypeptide, shown in FIG. 2 (SEQ ID NO:3), contains an open reading frame encoding a polypeptide of 395 amino acid residues, including an initiation codon at positions 1–3 in FIG. 2, with a leader sequence of about 21 amino acid residues, and a predicted molecular weight of about 43 kDa for the non-glycosylated mature protein. The amino acid sequence of the mature carboxy terminus modified TR1 receptor protein is shown in FIG. 2, amino acid residues from about 22 to about 395 (SEQ ID NO:4).

In a further aspect, the invention provides an isolated nucleic acid molecule comprising, or alternatively consisting of, a polynucleotide having a nucleotide sequence selected from the group consisting of: (a) a nucleotide sequence encoding a TR1 receptor polypeptide having the complete amino acid sequence in FIG. 1 (SEQ ID NO:2) or FIG. 2 (SEQ ID NO:4); (b) a nucleotide sequence encoding the predicted mature native TR1 receptor polypeptide having the amino acid sequence at about position 22 to about position 401 in FIG. 1 (SEQ ID NO:2) or the predicted mature carboxy terminus modified TR1 receptor polypeptide having the amino acid sequence at about position 22 to about position 395 in FIG. 2 (SEQ ID NO:4); (c) a nucleotide sequence encoding the native TR1 receptor polypeptide having the complete amino acid sequence encoded by the cDNA clone contained in ATCC Deposit No. 75899; (d) a nucleotide sequence encoding the mature native TR1 receptor polypeptide having the amino acid sequence encoded by the cDNA clone contained in ATCC Deposit No. 75899; and (e) a nucleotide sequence complementary to any of the nucleotide sequences in (a), (b), (c) or (d) above.

Further embodiments of the invention include isolated nucleic acid molecules that comprise, or alternatively consist of, a polynucleotide having a nucleotide sequence at least 80%, 85%, 90%, or 92% identical, and more preferably at least 95%, 96%, 97%, 98% or 99% identical, to any of the nucleotide sequences in (a), (b), (c), (d), or (e), above, or a polynucleotide which hybridizes under stringent hybridization conditions to a polynucleotide in (a), (b), (c), (d), or (e), above. This polynucleotide which hybridizes does not hybridize under stringent hybridization conditions to a polynucleotide having a nucleotide sequence consisting of only A residues or of only T residues.

An additional nucleic acid embodiment of the invention relates to an isolated nucleic acid molecule comprising, or alternatively consisting of, a polynucleotide which encodes the amino acid sequence of an epitope-bearing portion of a TR1 receptor polypeptide having an amino acid sequence in (a), (b), (c), or (d), above.

In accordance with another aspect of the present invention, there are provided novel mature polypeptides which are TR1 receptors, as well as fragments, analogs and derivatives thereof. The polypeptides of the present invention are of human origin and have amino acid sequences selected from the group consisting of: (a) the amino acid sequence of the native TR1 receptor polypeptide having the complete 401 amino acid sequence, including the leader sequence, shown in FIG. 1 (SEQ ID NO:2), or the amino acid sequence of the carboxy terminus modified TR1 receptor polypeptide having the complete 395 amino acid sequence, including the leader sequence, shown in FIG. 2 (SEQ ID NO:4); (b) the amino acid sequence of the predicted mature native TR1 receptor polypeptide (without the leader) having the amino acid sequence at about position 22 to about position 401 in FIG. 1 (SEQ ID NO:2) or the amino acid sequence of the predicted mature carboxy terminus modified TR1 receptor polypeptide (without the leader) having the amino acid sequence at about position 22 to about position 395 in FIG. 2 (SEQ ID NO:4); (c) the amino acid sequence of the native TR1 receptor polypeptide having the complete amino acid sequence, including the leader, encoded by the cDNA clone contained in ATCC Deposit No. 75899; and (d) the amino acid sequence of the mature native TR1 receptor polypeptide having the amino acid sequence encoded by the cDNA clone contained in ATCC Deposit No. 75899. The polypeptides of the present invention also include polypeptides having an amino acid sequence with at least 90% similarity, and more preferably at least 95% similarity to those described in (a), (b), (c) or (d) above, as well as polypeptides having an amino acid sequence at least 80% identical, at least 85% identical, more preferably at least 90% or 92% identical, and still more preferably 95%, 96%, 97%, 98% or 99% identical to those above.

The above-described soluble TR1 receptor polypeptides are believed not to include amino acids comprising a transmembrane domain. Thus, in a further aspect, the present invention provides TR1 receptor polypeptides that include such a transmembrane domain-containing amino acid sequence. Such polypeptides may be native or constructed from the TR1 receptors described herein.

An additional embodiment of this aspect of the invention relates to a peptide or polypeptide which has the amino acid sequence of an epitope-bearing portion of a TR1 receptor polypeptide having an amino acid sequence described in (a), (b), (c) or (d), above. Peptides or polypeptides having the amino acid sequence of an epitope-bearing portion of a TR1 receptor polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention. In another embodiment, the invention provides an isolated antibody that binds specifically to a TR1 receptor polypeptide having an amino acid sequence described in (a), (b), (c), or (d) above.

The invention also provides functional domains of the soluble TR1 receptor polypeptides of the present invention. These domains include amino acid residues from about 22 to about 261 in FIG. 1 (SEQ ID NO:2) and FIG. 2 (SEQ ID NO:4). The inventors have discovered that amino acid residues from about 22 to about 261 in FIGS. 1 and 2 are homologous to the extracellular domain of a publically known TNF-RII (FIG. 3). Further included are amino acid residues from about 262 to about 401 in FIG. 1 (SEQ ID NO:2) and amino acid residues from about 262 to about 395 in FIG. 2 (SEQ ID NO:4), which the present inventors have discovered are homologous to the intracellular domain of the publically known TNF-RII (FIG. 3).

The invention further provides methods for isolating antibodies that bind specifically to a TR1 receptor polypeptide having an amino acid sequence as described herein. Such antibodies are useful diagnostically or therapeutically as described below.

In accordance with yet a further aspect of the present invention, there is provided a process for producing such polypeptides by recombinant techniques which comprises culturing recombinant prokaryotic and/or eukaryotic host cells, containing a nucleic acid sequence encoding a polypeptide of the present invention, under conditions promoting expression of said protein and subsequent recovery of said protein. Thus, the present invention also relates to methods of making such vectors and host cells and for using them for production of TR1 receptor polypeptides or peptides by recombinant techniques.

In accordance with yet a further aspect of the present invention, there is provided a process for utilizing such polypeptides, or polynucleotide encoding such polypeptides to screen for receptor antagonists and/or agonists and/or receptor ligands. Such a screening method for identifying compounds capable of enhancing or inhibiting a cellular response induced by the TR1 receptor involves contacting cells which express the TR1 receptor with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In accordance with yet a further aspect of the present invention, there are provided nucleic acid probes comprising nucleic acid molecules of sufficient length to specifically hybridize to the polypeptide of the present invention.

In another aspect, screening assays for agonists and antagonists are provided which involve determining the effect a candidate compound has on the binding of cellular ligands capable of either eliciting or inhibiting a TR1 receptor mediated response. In particular, the methods involve contacting a TR1 receptor polypeptide with a candidate compound and determining whether TR1 receptor polypeptide binding to the cellular ligand is increased or decreased due to the presence of the candidate compound. Further, if binding to the TR1 receptor by the cellular ligand is altered, the effect on TR1 receptor activity is then determined. In addition, such assays may be used to identify compound which directly elicit a TR1 receptor mediated response.

In accordance with still another aspect of the present invention, there is provided a process of using such agonists for treating conditions related to insufficient TR1 receptor activity, for example, to inhibit tumor growth, to stimulate human cellular proliferation, e.g., T-cell proliferation, to regulate the immune response and antiviral responses, to protect against the effects of ionizing radiation, to protect against chlamydia infection, to regulate growth and to treat immunodeficiencies such as is found in HIV.

In accordance with another aspect of the present invention, there is provided a process of using such antagonists for treating conditions associated with over-expression of the TR1 receptor, for example, for treating T-cell mediated autoimmune diseases such as AIDS, septic shock, cerebral malaria, graft rejection, cytotoxicity, cachexia, apoptosis and inflammation.

The present inventors have discovered that TR1 receptor is expressed in pulmonary tissue, hippocampus, adult heart, kidney, liver, placenta, smooth muscle, thymus, prostate, ovary, small intestine and osteoblastoma and fibroblast cell lines. Further, the inventors have shown that a detectable quantity of TR1 receptor mRNA is not present in fetal brain, synovium, synovial sarcoma, T-cells, endothlial cells, activated macrophages, lymph nodes, thymus, neutrophils, and activated neutrophils. For a number of disorders, it is believed that significantly higher or lower levels of one or both of the TR1 receptor gene expressions can be detected in certain tissues (e.g., cancer, apoptosis, and inflammation) or bodily fluids (e.g., serum, plasma, urine, synovial fluid or spinal fluid) taken from an individual having such a disorder, relative to a "standard" TR1 receptor gene expression level, i.e., the TR1 receptor expression level in tissue or bodily fluids from an individual not having one of the disorders associated with aberrant TR1 receptor function. Thus, the invention provides a diagnostic method useful during diagnosis of a disorder associated with aberrant TR1 receptor function, which involves: (a) assaying TR1 receptor gene expression level in cells or body fluid of an individual; (b) comparing the TR1 receptor gene expression level with a standard TR1 receptor gene expression level, whereby an increase or decrease in the assayed TR1 receptor gene expression level compared to the standard expression level is indicative of a disorder associated with aberrant TR1 receptor function.

BRIEF DESCRIPTION OF THE FIGURES

FIGS. 1(A–B) shows the cDNA sequence (SEQ ID NO: 1) and corresponding deduced amino acid sequence (SEQ ID NO:2) of the native TR1 receptor polypeptide of the present invention which is believed to lack a transmembrane domain. The initial 21 amino acids represent the putative leader sequence and are underlined. The standard one-letter abbreviations for amino acids are used. Sequencing was performed using a 373 automated DNA sequencer (Applied Biosystems, Inc.). Sequencing accuracy is predicted to be greater than 97% accurate.

FIGS. 2(A–B) shows the cDNA sequence (SEQ ID NO:3) and corresponding deduced amino acid sequence (SEQ ID NO:4) of the carboxy terminus modified TR1 receptor polypeptide of the present invention. As above, the initial 21 amino acids represent the putative leader sequence and are underlined. Sequencing and abbreviations are as in FIG. 1.

FIG. 3 illustrates an amino acid sequence alignment of the native TR1 receptor polypeptide of the present invention (upper line) and the publically known human type 2 TNF receptor (human TNF-RII, shown on the lower line).

Figure 4:
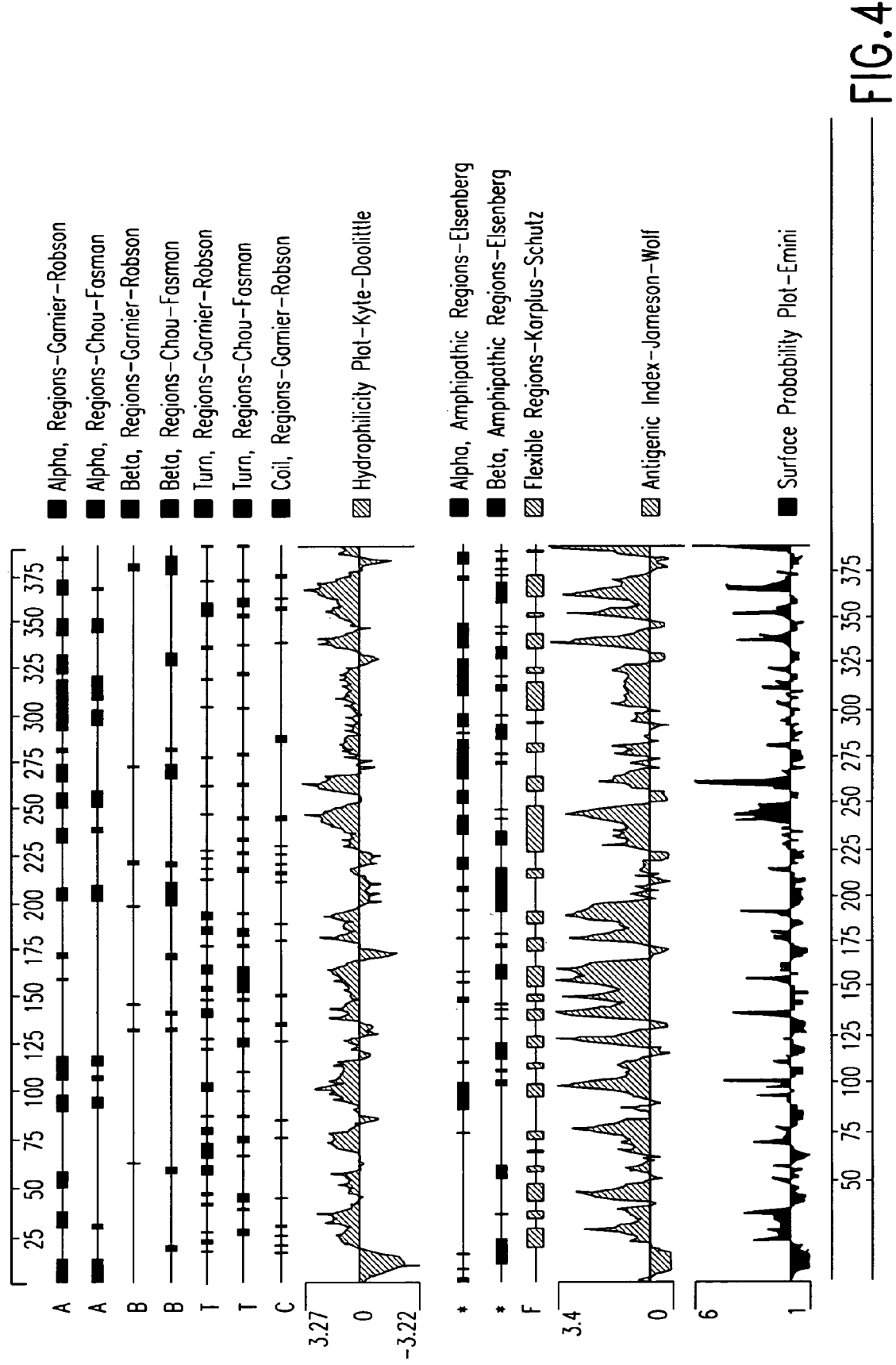

FIG. 4 shows an analysis of the native TR1 receptor amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 20–52, 66–203, 229–279, 297–378 in FIG. 1 correspond to the shown highly antigenic regions of the native TR1 receptor protein.

Figure 5:
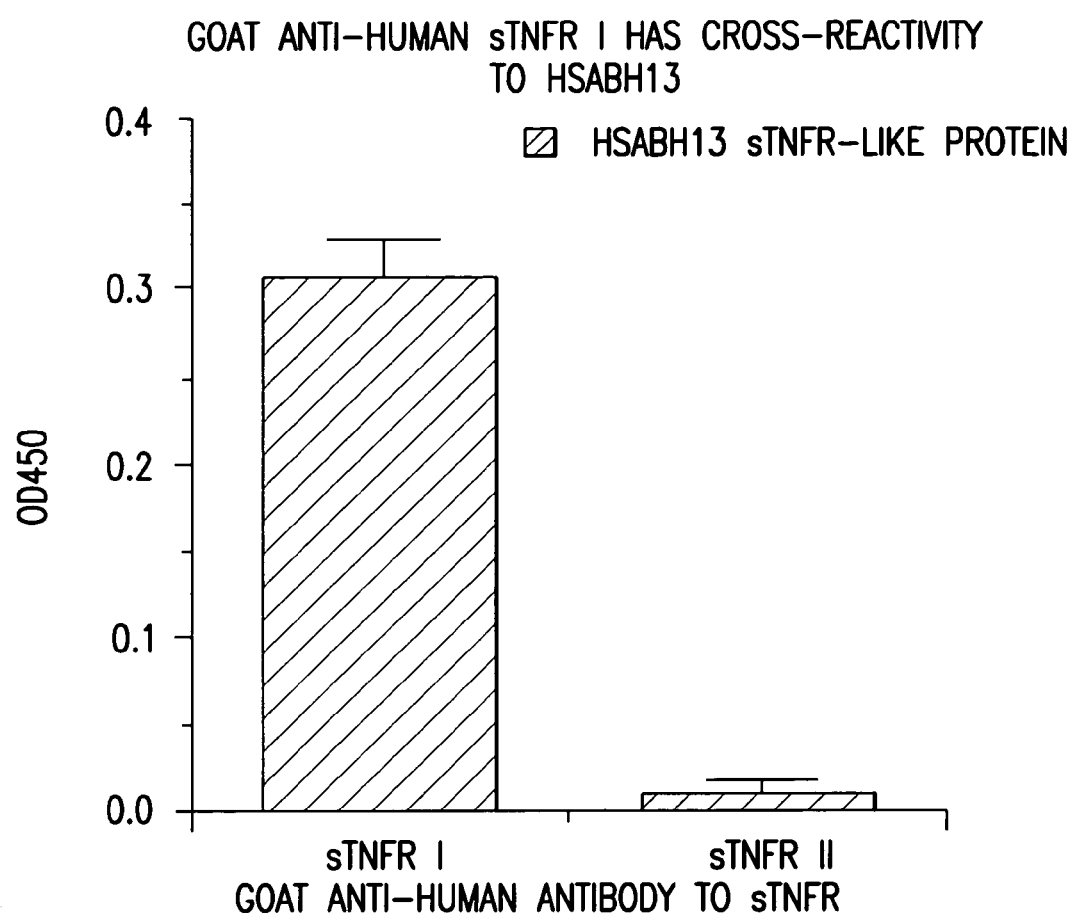

FIG. 5 shows a binding assay of polyclonal antibodies specific for human TNF-RI and TNF-RII and the native TR1 receptor of the present invention. Purified native TR1 receptor (HSABH13 protein) was added to well in a 96-well plate (100 μl/well), and incubated for 2 hours. After incubation, the plate was washed three times and phosphatase-labeled goat polyclonal antibody to human TNF-RI and TNF-RII (200 μl) was added to each well. After a further 2 hour incubation, the receptor-antibody conjugate was washed three times and 200 μl of substrate solution was added to each well. The plate was incubated further for 1 hr. The O.D. of the resulting solution was then measured using a ELISA reader (test wavelength 450 nm, correction wavelength 590 nm). All reagents were from R & D System (Minneapolis, Minn. 55413) and were used according to the manufacturer's instructions.

Figure 6:
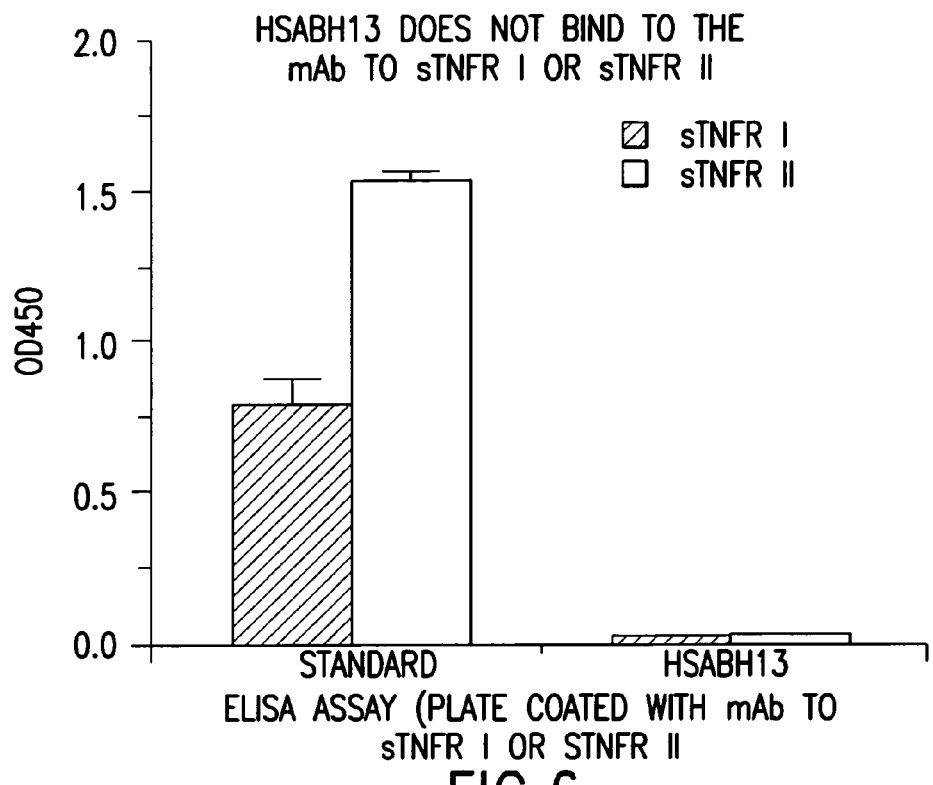

FIG. 6 shows a binding assay of the native TR1 receptor to monoclonal antibodies specific for type I and II TNF receptors. Purified native TR1 receptor (HSABH13 protein) (100 ul/well) was added to a 96-well plate provided by R&D system which was coated with mAbs to sTNFRI or sTNFRII, and incubated for 2 hr. After wasing three times with washing buffer, phosphatase-labeled polyclonal antibody to sTNF RI or sTNF RII (200 ml) was added. After a 2 hour incubation and three times wash, 200 ml of substrate solution was added to each well and the plate was incubated for 1 hr. The OD was measured using a ELISA reader (test wavelength 450 nm, correction wavelength 590 nm). All reagents were from R & D System.

Figure 7:
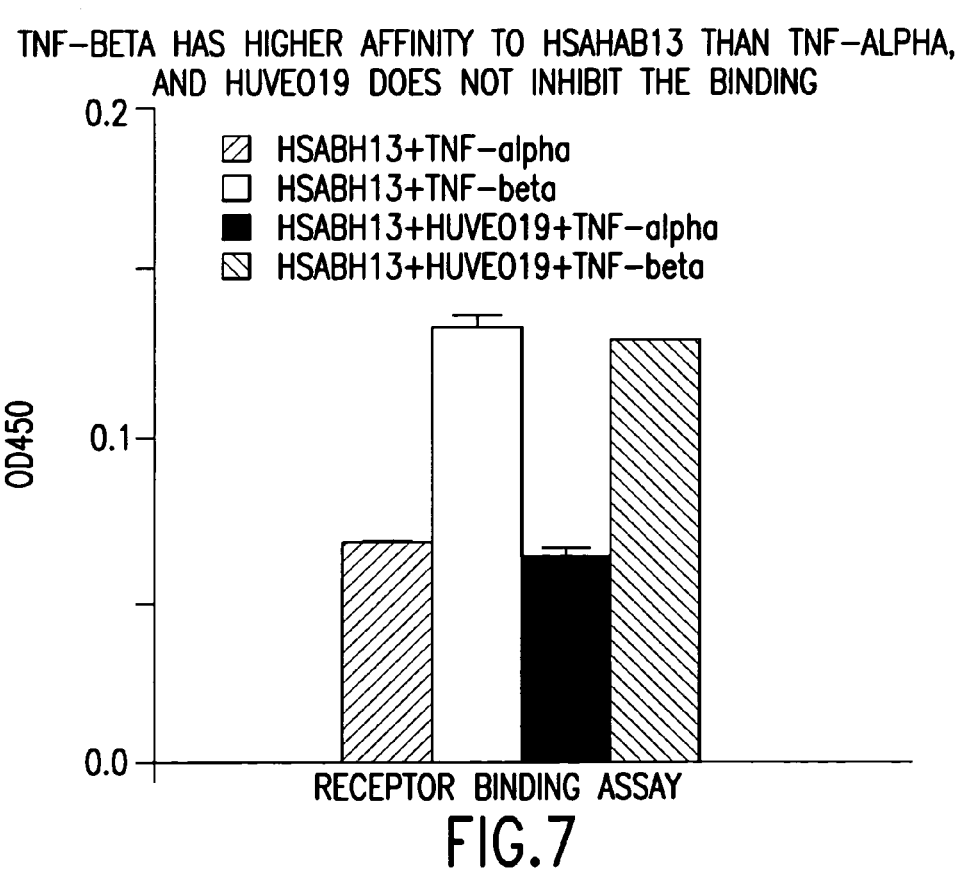

FIG. 7 shows a competitive binding assay between the native TR1 receptor of the present invention and a novel TNF ligand-like protein (HUVEO19) for TNF-α or TNF-β. Purified native TR1 receptor protein (100 μl well) was added to wells of a 96-well plate, and incubated for 2 hours. After incubation, the plate was washed three times, 10 ng of either TNF-α or TNF-β was added to the wells and the plate was incubated for an additional 2 hours followed by an additional three washes. In a duplicate plate, 10 ng of a novel TNF ligand-like protein (HUVEO19) was incubated first with native TR1 receptor and after the initial three washes, 10 ng of either TNF-α or TNF-β was added to the wells for the second incubation. For each plate, the wells were washed three times and phosphatase-labeled polyclonal antibody specific for either TNF-α or TNF-β (200 μl) was added. After a further 2 hour incubation, the wells were washed three times wash times and 200 μl of substrate solution was added to each well. The plates were then incubated for 1 hr and the O.D. was measured using a ELISA reader (test wavelength 450 nm, correction wavelength 590 nm). All reagents were obtained from R & D System, as above.

Figure 8:
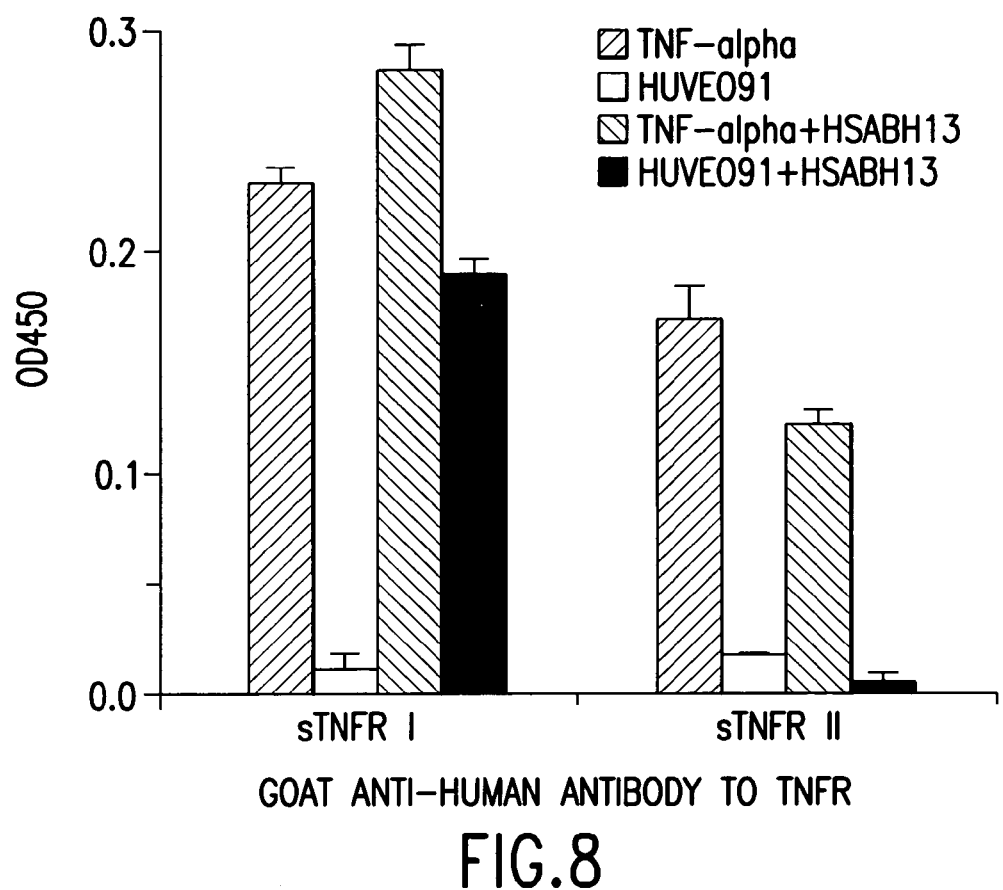

FIG. 8 shows a competitive binding assay between the native TR1 receptor of the present invention and human TNF-RI and TNF-RII for TNF-α and the novel TNF ligand-like protein described above. Purified native TR1 receptor protein (100 μl/well) was added to wells of a 96-well plate which was precoated with TNF-α or novel TNF ligand-like protein (HUVEO19), and incubated for 2 hours. After incubation, the plate was washed three times, 10 ng of either human TNF-RI or TNF-RII was added to the plate. The plate was then incubated for an additional 2 hr. After the 2 hour incubation, the wells were washed three times. In a duplicate plate, native TR1 receptor was omitted and 10 ng of either human TNF-RI or TNF-RII was added. After the second 2 hour incubation the plates were washed three times and phosphatase-labeled polygonal antibody to human TNF-RI or TNF-RII (200 μl) was added to each well. After an additional 2 hour incubation, the plates were washed three times wash, 200 μl of substrate solution was added to each well, and plate was incubated for 1 hour. The O.D. was then measured using a ELISA reader (test wavelength 450 nm, correction wavelength 590 nm). All reagents were obtained from R & D System, as above.

Figure 9A:
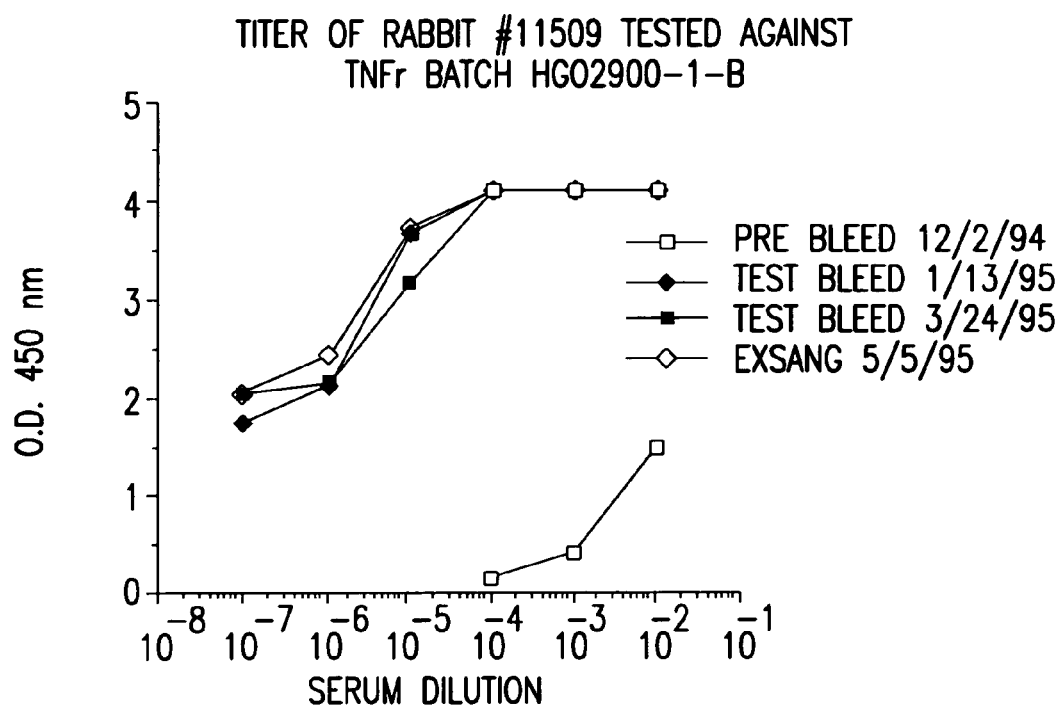
Figure 9B:
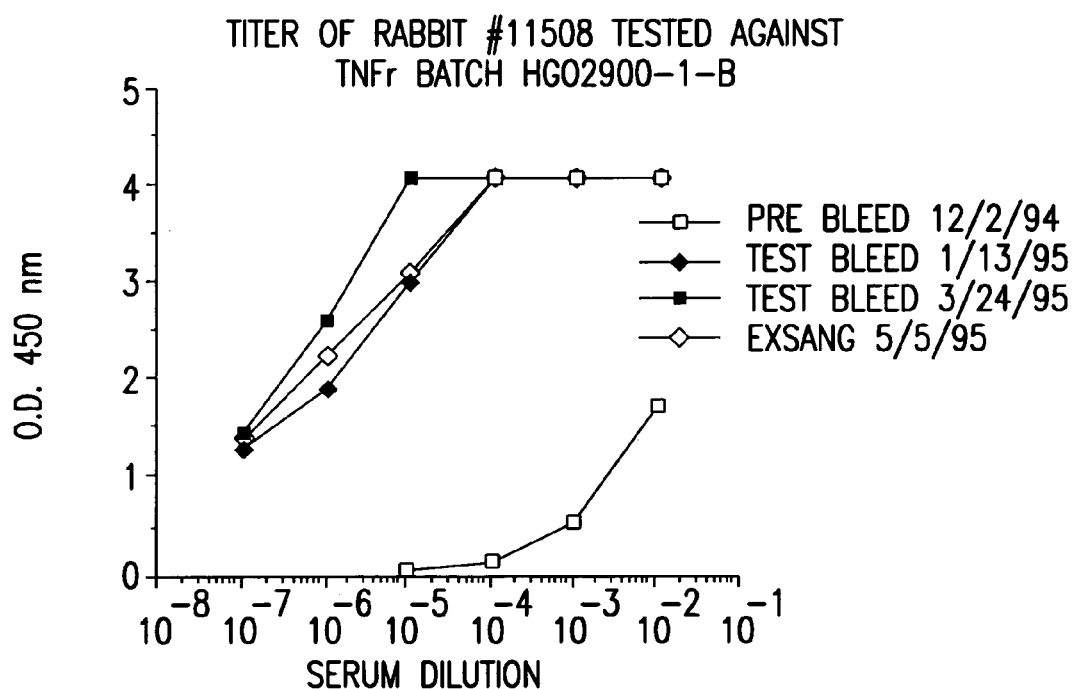

FIGS. 9(A–B) shows a screening assay (ELISA) of polyclonal rabbit anti-TR1 antibodies. Polyclonal rabbit anti-TR1 antibodies were prepared by Pocono Rabbit Farm & Laboratory, Inc. (Canadensis, Pa. 18325) according to standard protocol. The rabbit serum was tested by ELISA. In particular, the plates were coated with TR1 (labeled as TNFr batch HG02900-1-B) for 2 hours at room temperature or overnight at 4° C. After washing with PBS, they were blocked with PBS with 1% BSA and 0.5% sodium azide at 4° C. overnight. The PBS-BSA was flicked out of the well and test supernatants were added and incubated for 1 hour at room temperature. After 3 washes with PBS, 50 ml of anti-rabbit IgG horseradish peroxidase conjugate (1:1000 dilution in PBS with 1% BSA) was added and incubated at room temperature for 0.5–1 hr. After 3 washes with PBS, the substrate solution for IgG horseradish peroxidase was added to the plate and incubated at room temperature for 10–30 minutes. The reaction was stopped by adding 50 ml of 0.1 M EDTA. The absorbance was read at 450 nm.

DETAILED DESCRIPTION OF THE PREFERRED EMBODIMENTS

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

The term "gene" or "cistron" means the segment of DNA involved in producing a polypeptide chain; it includes regions preceding and following the coding region (leader and trailer) as well as intervening sequences (introns) between individual coding segments (exons).

In accordance with an aspect of the present invention, there is provided an isolated nucleic acid molecule comprising, or alternatively consisting of, a polynucleotide encoding the predicted mature native TR1 receptor polypeptide having the deduced amino acid sequence of FIG. 1 (SEQ ID NO:2) or for the mature native TR1 receptor polypeptide encoded by the cDNA of the clone which was deposited on Sep. 29, 1994 at the American Type Culture Collection, Patent Depository, 10801 University Boulevard, Manassas, Va. 20110-2209, and given accession number 75899. The nucleotide sequence shown in FIG. 1 (SEQ ID NO:1) was obtained by sequencing the HSABH13 clone deposited with the ATCC. The deposited clone is contained in the pBluescript SK(−) plasmid (Stratagene, LaJolla, Calif.).

Also provided is an isolated nucleic acid molecule comprising, or alternatively consisting of, a polynucleotide encoding the mature carboxy terminus modified TR1 receptor polypeptide having the deduced amino acid sequence of FIG. 2 (SEQ ID NO:4), which includes a frame shift at a carboxy terminal amino acid residue shown in FIG. 1 (SEQ ID NO:2). Due to the location of this frame shift, the inventors, as one skilled in the art would recognize, predict that a functional TR1 receptor with a modified carboxy terminus is encoded by FIG. 2 (SEQ ID NO:3). This conclusion is based on the fact that the remainder of the sequence remains substantially unaltered.

One skilled in the art would be able to produce such a carboxy terminus modified TR1 receptor as shown in FIG. 2 (SEQ ID NO:4) from the cDNA clone contained in ATCC Deposit No. 75899 or from an isolated naturally occurring polynucleotide using standard recombinant DNA techniques, which are described in numerous sources including in *Molecular Cloning, A Laboratory Manual*, 2nd. edition, Sambrook, J., Fritsch, E. F. and Maniatis, T., eds., Cold Spring Harbor Laboratory Press, Cold Spring Harbor, N.Y. (1989).

Using the information provided herein, such as the nucleotide sequence in FIG. 1 (SEQ ID NO:1) or FIG. 2 (SEQ ID NO:3), a cDNA molecule comprising a polynucleotide encoding a polypeptide of the present invention may be obtained from numerous human tissues, including pulmonary tissue, hippocampus, adult heart, kidney, liver, placenta, smooth muscle, thymus, prostate, ovary, small intestinal tissue and osteoblastoma and fibroblast cell lines. The present inventors have discovered that the native TR1 receptor of the present invention is expressed in each of the above tissues and cell types.

The cDNA contained in ATCC Deposit No. 75899 was isolated from a cDNA library derived from human early passage fibroblasts (HSA 172 cells) and is structurally related to a prior art human TNF-RII receptor. See FIG. 3 (SEQ ID NO:5). The determined nucleotide sequence of the TR1 receptor cDNA of FIG. 1 (SEQ ID NO: 1) contains an initiation codon at positions 46–48 of the nucleotide sequence in FIG. 1 (SEQ ID NO: 1) and contains an open reading frame encoding a protein of 401 amino acid residues of which approximately the first 21 amino acids residues are the putative leader sequence such that the mature protein comprises about 380 amino acids. The protein exhibits the highest degree of homology to human TNF-R2 with about 27% identity and about 43% similarity over the entire length of the proteins. Six conserved cyteines present in modules of 40 residues in all TNF receptors are conserved in this receptor.

As indicated, the present invention also provides the mature form(s) of the TR1 receptor proteins of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature TR1 receptor polypeptides having the amino acid sequence encoded by the cDNA clone contained in the host identified as ATCC Deposit No. 75899 and as shown in FIG. 1 (SEQ ID NO:2) and FIG. 2 (SEQ ID NO:4). By the mature TR1 receptor having the amino acid sequence encoded by the cDNA clone contained in the host identified as ATCC Deposit No. 75899 is meant the mature form(s) of the TR1 receptor protein produced by expression in a mammalian cell (e.g., COS cells, as described below) of the complete open reading frame encoded by the human DNA sequence of the clone contained in the vector in the deposited host. As indicated below, the mature TR1 receptor having the amino acid sequence encoded by the cDNA clone contained in ATCC Deposit No. 75899 may or may not differ from the predicted "mature" TR1 receptor protein shown in FIG. 1 (amino acids from about 22 to about 401) depending on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (*Virus Res.* 3:271–286 (1985)) uses the information from a short N-terminal charged region and a subsequent uncharged region of the complete (uncleaved) protein. The method of von Heinje (*Nucleic Acids Res.* 14:4683–4690 (1986)) uses the information from the residues surrounding the cleavage site, typically residues −13 to +2 where +1 indicates the amino acid terminus of the mature protein. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete TR1 receptor polypeptides of the present invention were analyzed by a computer program ("PSORT"). This program is available from Dr. Kenta Nakai of the Institute for Chemical Research, Kyoto University (see, K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 21 and 22 in FIG. 1 (SEQ ID NO:2) and FIG. 2 (SEQ ID NO:4). Thereafter, the complete amino acid sequences were further analyzed by visual inspection, applying a simple form of the (−1,−3) rule of von Heine. von Heinje, supra. Thus, the leader sequence for the native TR1 receptor protein is predicted to consist of amino acid residues 1–21 in FIG. 1 (SEQ ID NO:2), while the predicted mature native TR1 receptor protein consists of residues 22–401, and the leader sequence for the carboxy terminus modified TR1 receptor protein is predicted to consist of amino acid residues 1–21 in FIG. 2 (SEQ ID NO:4), while the predicted mature native TR1 receptor protein consists of residues 22–395 in FIG. 2 (SEQ ID NO:4).

Thus, in view of above, as one of ordinary skill would appreciate, the actual leader sequence of the TR1 receptor proteins of the present invention are predicted to be about 21 amino acids in length, but may be anywhere in the range of about 16 to about 27 amino acids. The TR1 receptors of the present invention are soluble receptors and are secreted. However, they may also exist as membrane bound receptors having a transmembrane region and intra- and extracellular regions. The polypeptides of the present invention may bind TNF and lymphotoxin ligands or other TNF ligand family members.

In accordance with an aspect of the present invention there are provided polynucleotides which may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1), FIG. 2 (SEQ ID NO:3) or that of the deposited clone or may be a different coding sequence which coding sequence, as a result of the redundancy or degeneracy of the genetic code, encodes the same mature polypeptide as the DNA of FIG. 1 (SEQ ID NO: 1), FIG. 2 (SEQ ID NO:3) or the deposited cDNA.

The polynucleotide which encodes for the mature polypeptide of FIG. 1 (SEQ ID NO:2), FIG. 2 (SEQ ID NO:4) or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to polynucleotides comprising, or alternatively consisting of, variants of the hereinabove described polynucleotides, which encode fragments, analogs and derivatives of the polypeptide having the deduced amino acid sequence of FIG. 1 (SEQ ID NO:2), FIG. 2 (SEQ ID NO:4), or the polypeptide encoded by the cDNA of the deposited clone. The variants of the polynucleotides may be naturally occurring allelic variants of the polynucleotides or non-naturally occurring variants of those polynucleotides.

In one aspect of this embodiment, the present invention is directed to fragments of the isolated nucleic acid molecules described herein. By a fragment of an isolated nucleic acid molecule having the nucleotide sequence of the deposited cDNA or the nucleotide sequence shown in FIG. 1 (SEQ ID NO:1) or FIG. 2 (SEQ ID NO:4) is intended fragments at least about 15 nt, and more preferably at least about 20 nt, still more preferably at least about 30 nt, and even more preferably, at least about 40 nt in length which are useful as diagnostic probes and primers as discussed herein. In this context, "about" includes the particularly recited values and values larger or smaller by several (5, 4, 3, 2, and 1) nucleotides. Of course, larger fragments, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, or 1200 nt in length are also useful according to the present invention as are fragments corresponding to most, if not all, of the nucleotide sequence shown in FIG. 1 (SEQ ID NO: 1), FIG. 2 (SEQ ID NO:3), of the deposited cDNA. By a fragment at least 20 nt in length, for example, is intended fragments which include 20 or more contiguous bases from the nucleotide sequence of the deposited cDNA or the nucleotide sequence as shown in FIG. 1 (SEQ ID NO:1) or FIG. 2 (SEQ ID NO:3).

The present invention is further directed to polynucleotides comprising, or alternatively consisting of, fragments of isolated nucleic acid molecules which encode subportions of TR1 receptor domains. In particular, the invention provides polynucleotides comprising, or alternatively consisting of, the nucleotide sequences of a member selected from the group consisting of nucleotides 46–105, 106–165, 166–225, 226–285, 286–345, 346–405, 406–465, 466–525, 526–585, 586–645, 646–705, 706–765, 766–825, 826–885, 886–945, 946–1005, 1006–1065, 1066–1125, 1126–1185, 1186–1245, or 1186–1248 of SEQ ID NO:1, or the complementary strand thereto.

The invention also provides polynucleotides comprising, or alternatively consisting of, the nucleotide sequences of a member selected from the group consisting of nucleotides 1–60, 11–70, 64–123, 124–183, 184–243, 244–303, 304–363, 364–423, 424–483, 484–543, 544–603, 604–663, 664–723, 724–783, 784–843, 844–903, 904–963, 964–1023, 1024–1083, 1084–1143, or 1129–1188 of SEQ ID NO:3, or the complementary strand thereto.

The present invention is further directed to polynucleotides comprising, or alternatively consisting of, isolated nucleic acid molecules which encode domains of the TR1 receptor. In one aspect, the invention provides polynucleotides comprising, or alternatively consisting of, nucleic acid molecules which encode beta-sheet regions of the TR1 receptor set out in Table 2. Representative examples of such polynucleotides comprise, or alternatively consist of, nucleic acid molecules which encode a polypeptide having an amino acid sequence selected from the group consisting of amino acid residues from about 16 to about 22, amino acid residues from about 57 to about 63, amino acid residues from about 129 to about 134, amino acid residues from about 139 to about 143, amino acid residues from about 167 to about 174, amino acid residues from about 197 to about 203, amino acid residues from about 205 to about 214, amino acid residues from about 220 to about 225, amino acid residues from about 265 to about 275, amino acid residues from about 281 to about 285, amino acid residues from about 325 to about 335, amino acid residues from about 366 to about 401, and amino acid residues from about 396 to about 401 of SEQ ID NO:2. The invention is further directed to isolated polypeptides comprising, or alternatively consisting of, an amino acid sequence selected from the group consisting of amino acid residues from about 16 to about 22, amino acid residues from about 57 to about 63, amino acid residues from about 129 to about 134, amino acid residues from about 139 to about 143, amino acid residues from about 167 to about 174, amino acid residues from about 197 to about 203, amino acid residues from about 205 to about 214, amino acid residues from about 220 to about 225, amino acid residues from about 265 to about 275, amino acid residues from about 281 to about 285, amino acid residues from about 325 to about 335, amino acid residues from about 366 to about 401, and amino acid residues from about 396 to about 401 of SEQ ID NO:2. In this context "about" includes the particularly recited value and values larger or smaller by several (5, 4, 3, 2, or 1) amino acids.

Nucleic acid fragments of the present invention include nucleic acid molecules encoding beta-sheet regions of the the TR1 receptor protein, as well as isolated nucleic acid molecules comprising, or alternatively consisting of, a polynucleotide having a nucleotide sequence at least 80% identical, and more preferably at least 85%, 90%, 92%, 95%, 96%, 97%, 98% or 99% identical to nucleic acid molecules encoding beta-sheet regions of the the TR1 receptor protein. Polynucleotides encoding polypeptides at least 80%, 85%, 90%, 92%, 95%, 96%, 97%, 98%, or 99% identical to beta-sheet regions are also with the scope of the invention, as are the polypeptides encoded by these polynucleotides.

Since the gene has been deposited and the nucleotide sequence shown in FIG. 1 (SEQ ID NO: 1) and FIG. 2 (SEQ ID NO:3) are provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the TR1 receptor protein. In particular, such nucleic acid fragments of the present invention include nucleic acid molecules encoding: a polypeptide comprising, or alternatively consisting of, amino acid residues from about 20 to about 52 in FIG. 1 (SEQ ID NO:2) or FIG. 2 (SEQ ID NO:4); a polypeptide comprising, or alternatively consisting of, amino acid residues from about 66 to about 203 in FIG. 1 (SEQ ID NO:2) or FIG. 2 (SEQ ID NO:4); a polypeptide comprising, or alternatively consisting of, amino acid residues from about 229 to about 279 in FIG. 1 (SEQ ID NO:2) or FIG. 2 (SEQ ID NO:4); and a polypeptide comprising, or alternatively consisting of, amino acid residues from about 297 to about 378 in FIG. 1 (SEQ ID NO:2).

In this context, "about" includes the particularly recited values and values larger or smaller by several (5, 4, 3, 2, and 1) nucleotides. Using the Jameson-Wolf graph shown in FIG. 4, the inventors have determined that the above polypeptide fragments are antigenic regions of the TR1 receptor protein.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO: 1), FIG. 2 (SEQ ID NO:3), or of the coding sequence of the deposited clone. As indicated, one particularly preferred variant is a TR1 receptor containing a transmembrane domain inserted after amino acid residue about 260 or 261 in FIG. 1 or FIG. 2. As known in the art, an allelic variant is an alternate form of a polynucleotide sequence which may have a substitution, deletion or addition of one or more nucleotides, which does not substantially alter the function of the encoded polypeptide. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques, which include, but are not limited to, oligonucleotide mediated mutagenesis, alanine scanning, PCR mutagenesis, site-directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London Ser A* 317:415 (1986)).

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TR1 receptor proteins or portions thereof. Also especially preferred in this regard are conservative substitutions. Most highly preferred are nucleic acid molecules encoding the mature native TR1 receptor protein having the amino acid sequence shown in FIG. 1 (SEQ ID NO:2), the mature native TR1 receptor amino acid sequence encoded by the deposited cDNA clone, or the mature carboxy terminus modified TR1 receptor protein having the amino acid sequence shown in FIG. 2 (SEQ ID NO:4).

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Such isolated molecules, particularly DNA molecules, are useful as probes for gene mapping, by in situ hybridization with chromosomes, and for detecting expression of the TR1 receptor genes in human tissue, for instance, by Northern blot analysis.

Thus, for example, the polynucleotide of the present invention may encode for a mature protein, or for a protein having a prosequence or for a protein having both a prosequence and a presequence (leader sequence).

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread," as in a karyotype), is not "isolated" for the purposes of the invention. As discussed further herein, isolated nucleic acid molecules according to the present invention may be produced naturally, recombinantly, or synthetically.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson et al., *Cell,* 37:767 (1984)). The coding sequence may also be fused to a sequence which codes for a fusion protein such as an IgG Fc fusion protein.

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 80%, preferably at least 90% or 92%, and more preferably at least 95%, 96%, 97%, 98% or 99% identity between the sequences. The present invention particularly relates to polynucleotides which hybridize under stringent conditions to the hereinabove-described polynucleotides, for instance, the cDNA contained in ATCC Deposit 75899. By "stringent hybridization conditions" is intended overnight incubation at 42° C. in a solution comprising: 50% formamide, 5× SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1× SSC at about 65° C.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Of course, polynucleotides hybridizing to a larger portion of the reference polynucleotide (e.g., the deposited cDNA clone), for instance, a portion 50–750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIG. 1 (SEQ ID NO: 1) or FIG. 2 (SEQ ID NO:3). By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO: 1) or FIG. 2 (SEQ ID NO:3)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a TR1 receptor cDNA clone has been deposited and its determined nucleotide sequence is provided in FIG. 1 (SEQ ID NO: 1), generating polynucleotides which hybridize to a portion of the TR1 receptor cDNA molecule would be routine to the skilled artisan. For example, restriction endonuclease cleavage or shearing by sonication of the TR1 receptor cDNA clone could easily be used to generate DNA portions of various sizes which are polynucleotides that hybridize to a portion of the TR1 receptor cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the TR1 receptor cDNA shown in FIG. 1 (SEQ ID NO: 1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated from an oligo-dT primed cDNA library).

Further embodiments of the invention include isolated nucleic acid molecules comprising a polynucleotide having a nucleotide sequence at least 80%, 85%, 90%, or 92% identical, and more preferably at least 95%, 96%, 97%, 98% or 99% identical to (a) a nucleotide sequence encoding the full-length native TR1 receptor polypeptide having the complete amino acid sequence in FIG. 1 (SEQ ID NO:2) or a nucleotide sequence encoding the full-length carboxy terminus modified TR1 receptor polypeptide having the complete amino acid sequence in FIG. 2 (SEQ ID NO:4), including the predicted leader sequences; (b) a nucleotide sequence encoding the mature native TR1 receptor polypeptide (full-length polypeptide with the leader removed) having the amino acid sequence at positions about 22 to about 401 in FIG. 1 (SEQ ID NO:2) or a nucleotide sequence encoding the mature carboxy terminus modified TR1 receptor polypeptide (full-length polypeptide with the leader removed) having the amino acid sequence at positions about 22 to about 395 in FIG. 2 (SEQ ID NO:4); (c) a nucleotide sequence encoding the full-length native TR1 receptor polypeptide having the complete amino acid sequence including the leader encoded by the cDNA clone contained in ATCC Deposit No. 75899; (d) a nucleotide sequence encoding the mature native TR1 receptor polypeptide having the amino acid sequence encoded by the cDNA clone contained in ATCC Deposit No. 75899; or (e) a nucleotide sequence complementary to any of the nucleotide sequences in (a), (b), (c), or (d).

By a polynucleotide having a nucleotide sequence at least, for example, 95% "identical" to a reference nucleotide sequence encoding a TR1 receptor polypeptide is intended that the nucleotide sequence of the polynucleotide is identical to the reference sequence except that the polynucleotide sequence may include up to five point mutations, or mismatches, per each 100 nucleotides of the reference nucleotide sequence encoding the TR1 receptor polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations, or mismatches, of the reference sequence may occur at the 5' or 3' terminal positions of the reference nucleotide sequence or anywhere between those terminal positions, interspersed either individually among nucleotides in the reference sequence or in one or more contiguous groups within the reference sequence.

The reference (query) sequence may be the entire TR1 encoding nucleotide sequence shown in FIG. 1 (SEQ ID NO:2), FIG. 2 (SEQ ID NO:4) or any TR1 polynucleotide fragment as described herein.

As a practical matter, whether any particular nucleic acid molecule is at least 90%, 95%, 96%, 97%, 98% or 99% identical to, for instance, the nucleotide sequence shown in FIG. 1, FIG. 2 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As a practical matter, whether any particular nucleic acid molecule is at least 90%, 95%, 96%, 97%, 98% or 99% identical to, for instance, the encoding nucleotide sequence shown in FIG. 1 (SEQ ID NO:2), FIG. 2 (SEQ ID NO:4) or to the nucleotide sequence of the deposited cDNA clone, can be determined conventionally using known computer programs such as the Bestfit program (Wisconsin Sequence Analysis Package, Version 8 for Unix, Genetics Computer Group, University Research Park, 575 Science Drive, Madison, Wis. 53711) to find the best segment of homology, as described above.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237–245 (1990)). Preferred parameters used in a FASTDB alignment of DNA sequences to calculate percent identity are: Matrix=Unitary, k-tuple=4, Mismatch Penalty=, Joining Penalty=30, Randomization Group Length=0, CutoffScore=1, Gap Penalty=5, Gap Size Penalty 0.05, Window Size=500 or the length of the subject nucleotide sequence, whichever is shorter.

According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment.

Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a match/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%.

In another example, a 90 base subject sequence is compared with a 100 base query sequence. This time the deletions are internal deletions so that there are no bases on the 5' or 3' ends of the subject sequence which are not matched/aligned with the query sequence. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

Preferred, however, are nucleic acid molecules having sequences at least 80%, 85%, 90%, 92%, 95%, 96%, 97%, 98% or 99% identical to the nucleic acid sequence shown in FIG. 1 (SEQ ID NO: 1), FIG. 2 (SEQ ID NO:3) or to the nucleic acid sequence of the deposited cDNA which do, in fact, encode a polypeptide having TR1 receptor protein activity. By "a polypeptide having TR1 receptor activity" is intended polypeptides exhibiting activity similar, but not necessarily identical, to an activity of the TR1 receptor protein of the invention (either the full-length protein or, preferably, the mature protein), as measured in a particular biological assay. For example, TR1 receptor protein activity can be measured using the binding affinity for a TR1-β ligand or other molecule shown to bind to the native TR1 receptor protein. For example, the competitive binding assays shown in FIG. 7 can be used to determine whether a candidate polypeptide has a binding affinity similar to that of the native TR1 receptor described herein.

Thus, "a polypeptide having TR1 receptor protein activity" includes polypeptides that exhibit TR1 receptor binding activity in the above-described assays. Although the degree of binding activity need not be identical to that of the TR1 receptor protein, preferably, "a polypeptide having TR1 receptor protein activity" will exhibit substantially similar activity as compared to the native TR1 receptor protein.

The present application is directed to nucleic acid molecules at least 80%, 85%, 90%, 92%, 95%, 96%, 97%, 98% or 99% identical to the nucleic acid sequences (i.e., polynucleotides) disclosed herein, irrespective of whether they encode a polypeptide having TR1 functional activity. This is because even where a particular nucleic acid molecule does not encode a polypeptide having TR1 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR1 functional activity include, but are not limited to, inter alia, (1) isolating a TR1 gene or allelic or splice variants thereof in a cDNA library; (2) in situ hybridization (e.g., "FISH") to metaphase chromosomal spreads to provide precise chromosomal location of a TR1 gene, as described in Verma et al., *Human Chromosomes: A Manual of Basic Techniques*, Pergamon Press, New York (1988); and (3) Northern Blot analysis for detecting TR1 mRNA expression in specific tissues.

Preferred, however, are nucleic acid molecules having sequences at least 80%, 85%, 90%, 92%, 95%, 96%, 97%, 98% or 99% identical to the nucleic acid sequences disclosed herein, which do, in fact, encode a polypeptide having TR1 functional activity. By "a polypeptide having TR1 functional activity" is intended polypeptides exhibiting activity similar, but not necessarily identical, to an activity of the TR1 receptors of the present invention (either the full-length polypeptide, or the splice variants), as measured, for example, in a particular immunoassay or biological assay. For example, TR1 activity can be measured by determining the ability of a TR1 polypeptide to bind a TR1 ligand (e.g., TRANCE (Anderson et al., *Nature* 390:175–179 (1997); TRAIL (Wiley, S. R., et al., *Immunity* 3:673–682(1995); and OPGL (Kong, Y. Y., et al., *Nature* 397:315–323 (1999)).

Of course, due to the degeneracy of the genetic code, one of ordinary skill in the art will immediately recognize that a large number of the nucleic acid molecules having a sequence at least 90%, 95%, 96%, 97%, 98% or 99% identical to the nucleic acid sequence of the deposited cDNA, the nucleic acid sequence shown in FIG. 1 (SEQ ID NO: 1) or FIG. 2 (SEQ ID NO:3), or fragments thereof, will encode polypeptides "having TR1 functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having TR1 functional activity. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., *Science* 247:1306–1310 (1990) (indicating that proteins are surprisingly tolerant of amino acid substitutions), and the references cited therein.

Preferably, the polynucleotide fragments of the invention encode a polypeptide which demonstrates a TR1 functional activity. By a polypeptide demonstrating "functional activity" is meant, a polypeptide capable of displaying one or more known functional activities associated with a full-length TR1 polypeptide. Such functional activities include, but are not limited to, biological activity (e.g., inhibition of osteoclastogenesis; stimulation of increased bone density; enhancement of B and T cell growth, proliferation and/or differentiation; regulation of dendritic cell function), antigenicity (ability to bind (or to compete with a TR1 polypeptide for binding) to an anti-TR1 antibody), immunogenicity (ability to generate antibody which binds to a TR1 polypeptide), and ability to bind to a receptor or ligand for a TR1 polypeptide (e.g., TRANCE (Anderson et al., *Nature* 390:

175–179 (1997); TRAIL (Wiley, S. R., et al., *Immunity* 3:673–682(1995); and OPGL (Kong, Y. Y., et al., *Nature* 397:315–323 (1999)).

The functional activity of TR1 polypeptides, and fragments, variants derivatives, and analogs thereof, can be assayed by various methods.

For example, in one embodiment where one is assaying for the ability to bind or compete with full-length TR1 polypeptide for binding to anti-TR1 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by a labeled primary antibody. In another embodiment, the primary antibody is detected by binding of a secondary antibody or reagent to the primary antibody. In a further embodiment, the secondary antibody is labeled. Many means are known in the art for detecting binding in an immunoassay and are within the scope of the present invention.

In another embodiment, where a TR1 ligand is identified (e.g., TRANCE (Anderson et al., *Nature* 390:175–179 (1997); TRAIL (Wiley, S. R., et al., *Immunity* 3:673–682 (1995); OPGL (Kong, Y. Y., et al., *Nature* 397:315–323 (1999)), or the ability of a polypeptide fragment, variant or derivative of the invention to multimerize is being evaluated, binding can be assayed by means well-known in the art, such as: reducing and non-reducing gel chromatography, protein affinity chromatography, and affinity blotting, for example. See generally, Phizicky, E., et al., 1995, *Microbiol. Rev.* 59:94–123. In another embodiment, physiological correlates of TR1 binding to its substrates (signal transduction) can be assayed. In addition, assays known in the art may routinely be applied to measure the ability of TR1 polypeptides and fragments, variants derivatives and analogs thereof to elicit TR1 related biological activity in vitro or in vivo (e.g., inhibition of osteoclastogenesis; stimulation of increased bone density; enhancement of B and T cell growth, proliferation and/or differentiation; regulation of dendritic cell function). Other methods will be known to the skilled artisan and are within the scope of the invention.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

TR1 Receptor Polypeptides and Fragments

The present invention further relates to a polypeptide which has the deduced amino acid sequence of FIG. 1 (SEQ ID NO:2), FIG. 2 (SEQ ID NO:4), or which has the amino acid sequence encoded by the deposited cDNA, as well as fragments, analogs and derivatives of such a polypeptide.

The terms "fragment," "derivative" and "analog" when referring to the polypeptide of FIG. 1 (SEQ ID NO:2), FIG. 2 (SEQ ID NO:4), or that encoded by the deposited cDNA, means a polypeptide which retains essentially the same biological function or activity as such a polypeptide. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

It will be recognized in the art that some amino acid sequences of the TR1 receptor polypeptide can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the TR1 receptor polypeptide which show substantial TR1 receptor polypeptide activity or which include regions of TR1 receptor protein such as the protein portions discussed below. Such mutants include deletions, insertions, inversions, repeats, and type substitutions (for example, substituting one hydrophilic residue for another, but not substituting a strongly hydrophilic one for a strongly hydrophobic one as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie et al, supra.

Thus, the fragment, derivative or analog of the polypeptide of FIG. 1 (SEQ ID NO:2), FIG. 2 (SEQ ID NO:4), or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein. Polynucleotides encoding these fragments, derivatives or analogs are also encompassed by the invention.

Of particular interest are substitutions of charged amino acids with another charged amino acid and with neutral or negatively charged amino acids. The latter results in proteins with reduced positive charge to improve the characteristics of the TR1 receptor proteins. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the TR1 receptors of the present invention may include one or more amino acid substitutions, deletions or additions, either from natural mutations or human manipulation.

Changes are preferably of a minor nature, such as conservative amino acid substitutions that do not significantly affect the folding or activity of the protein (see Table 1).

TABLE 1

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TR1 receptors of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224: 899–904 (1992) and de Vos et al., *Science* 255:306–312 (1992)).

The polypeptides and polynucleotides of the present invention are preferably provided in an isolated form, and preferably are purified to homogeneity. A recombinantly produced version of the TR1 receptor polypeptide can be substantially purified by the one-step method described in Smith and Johnson, *Gene* 67:31–40 (1988).

The polypeptides of the present invention include the polypeptide encoded by the deposited cDNA including the leader, the mature polypeptide encoded by the deposited cDNA minus the leader (i.e., the mature protein), the polypeptide of FIG. 1 (SEQ ID NO:2) or FIG. 2 (SEQ ID NO:4) including the leader, the polypeptide of FIG. 1 (SEQ ID NO:2) or FIG. 2 (SEQ ID NO:4) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical or 85% identical, more preferably at least 90% or 92% identical, still more preferably at least 95%, 96%, 97%, 98% or 99% identical to the polypeptide encoded by the deposited cDNA, to the polypeptide of FIG. 1 (SEQ ID NO:2), the polypeptide of FIG. 2 (SEQ ID NO:4), and also include portions of such polypeptides with at least 30 amino acids and more preferably at least 50 amino acids. Such portions may include an additional N-terminal methionine residue.

As known in the art "similarity" between two polypeptides is determined by comparing the amino acid sequence and its conserved amino acid substitutes of one polypeptide to the sequence of a second polypeptide. By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482–489, 1981) to find the best segment of similarity between two sequences.

By a polypeptide having an amino acid sequence at least, for example, 95% "identical" to a reference amino acid sequence of a TR1 receptor polypeptide is intended that the amino acid sequence of the polypeptide is identical to the reference sequence except that the polypeptide sequence may include up to five amino acid alterations per each 100 amino acids of the reference sequence of the TR1 receptor polypeptides of the present invention. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequence shown in FIG. 1 (SEQ ID NO:2), FIG. 2 (SEQ ID NO:4), or the amino acid sequence encoded by deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (*Comp. App. Biosci.* 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment.

Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%.

In another example, a 90 amino acid residue subject sequence is aligned with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention have uses that include, but are not limited to, as sources for generating antibodies that bind the polypeptides of the invention, and as molecular weight markers on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting TR1 receptor protein expression as described below or as agonists and antagonists capable of enhancing or inhibiting TR1 receptor protein function. Further, such polypeptides can be used in the yeast two-hybrid system to "capture" TR1 receptor protein binding proteins which are also candidate agonist and antagonist according to the present invention. The yeast two hybrid system is described in Fields and Song, *Nature* 340:245–246 (1989).

As indicated, the above described TR1 receptor polypeptides are believed not to include a transmembrane domain. Thus, in an additional embodiment, the present invention relates to the TR1 receptor polypeptides of the present invention having an amino acid sequence further comprising a transmembrane domain. Such receptor polypeptides may be native or constructed from the TR1 receptors described herein according to recombinant techniques. Methods for isolating a nucleotide sequence encoding a TR1 receptor that contains a transmembrane domain include hybridizing nucleotide probes constructed from the sequence provided in FIG. 1 (SEQ ID NO: 1) or FIG. 2 (SEQ ID NO:3) with a cDNA library obtained from one or more of the above described tissue sources.

If produced recombinantly or synthetically, suitable sites for the insertion of a transmembrane domain spanning amino acid sequence will be apparent to one skilled in the art. The present inventors have discovered that amino acid residues from about 22 to about 261, shown in FIG. 1 (SEQ ID NO:2), have considerable homology to the extracellular domain of human TR1-RII (FIG. 3; SEQ ID NO:5). Further, amino acid residues from about 262 to about 401, shown in FIG. 1 (SEQ ID NO:2), have considerable homology to the intracellular domain of human TR1-RII (FIG. 3; SEQ ID NO:5). Thus, one skilled in the art would appreciate that between amino acid residues 261 and 262 in either FIG. 1 (SEQ ID NO:2) or FIG. 2 (SEQ ID NO:4) (or a site proximal—within about 1–10 amino acids—thereto) would be a suitable site for the insertion of an amino acid sequence comprising a transmembrane domain. Polynucleotides encoding an amino acid sequence comprising a transmembrane domain may be isolated from (or constructed from the nucleotide sequence of) other TR1 receptor genes and inserted into an appropriate site of the deposited clone by recombinant techniques. Further, such domains may be synthetically constructed and inserted into the soluble TR1 receptors of the present invention. Insertion of such amino acid residues comprising a transmembrane domain into a TR1 receptor of the present invention would likely result in a non-soluble receptor that would integrate into membranes. A specific example of a transmembrane domain useful according to the present invention is the TNF-R2 transmembrane domain shown at amino acid residues from about 258 to about 287 in FIG. 3 (bottom sequence) (SEQ ID NO:5). Other such TR1 receptor transmembrane domains will be apparent to the those skilled in the art.

Epitopic Polypeptide Fragments

The present invention also encompasses polypeptides comprising, or alternatively consisting of, an epitope of the polypeptide having an amino acid sequence of SEQ ID NO:2 or SEQ ID NO:4, or an epitope of the polypeptide sequence encoded by a polynucleotide sequence contained in deposited clone identified as ATCC Accession No. 75899, or encoded by a polynucleotide that hybridizes to the complement of the sequence of SEQ ID NO: 1 or SEQ ID NO:3 or contained in the deposited clone identified as ATCC Accession No. 75899 under stringent hybridization conditions or lower stringency hybridization conditions as defined supra. The present invention further encompasses polynucleotide sequences encoding an epitope of a polypeptide sequence of the invention (such as, for e.g., the sequence disclosed in SEQ ID NOS:1 and 3), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., *Proc. Natl Acad. Sci. USA* 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments that function as epitopes may be produced by any conventional means known in the art (See, e.g., Houghten, *Proc. Natl Acad. Sci. USA* 82:5131–5135 (1985), and further description in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. See, for instance, Wilson et al., *Cell* 37:767–778 (1984); Sutcliffe et al., *Science* 219:660–666 (1983).

Similarly, immunogenic epitopes can be used, for example, to induce antibodies according to methods well known in the art. (See, for instance, Sutcliffe et al., supra; Wilson et al., supra; Chow et al., *Proc. Natl Acad. Sci. USA* 82:910–914 (1985); and Bittle et al., *J. Gen. Virol.* 66:2347–2354 (1985)). A preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.*, 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature,* 331:84–86 (1988). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., *J. Biochem.,* 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht, R. et al., *Proc. Natl. Acad. Sci. USA* 88:8972–8976 (1991). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Pattent et al., Curr. Opinion Biotechnol. 8:724–733 (1997); Harayama, Trends Biotechnol. 16:76–82 (1998); Hansson et al., J. Mol. Biol. 287:265–276 (1999); and Lorenzo and Blasco, Biotechniques 24:308–313 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

Non-limiting examples of antigenic polypeptides or peptides that can be used to generate TR1 receptor-specific antibodies include: a polypeptide comprising amino acid residues from about 20 to about 52 in FIG. 1 (SEQ ID NO:2) or FIG. 2 (SEQ ID NO:4); a polypeptide comprising amino acid residues from about 66 to about 203 in FIG. 1 (SEQ ID NO:2) or FIG. 2 (SEQ ID NO:4); a polypeptide comprising amino acid residues from about 229 to about 279 in FIG. 1 (SEQ ID NO:2) or FIG. 2 (SEQ ID NO:4); a polypeptide comprising amino acid residues from about 297 to about 378 in FIG. 1 (SEQ ID NO:2). As indicated above, the inventors have determined that the above polypeptide fragments are antigenic regions of the TR1 receptor protein.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention is further directed to isolated polypeptides comprising, or alternatively consisting of, fragments of TR1. In particular, the invention provides isolated polypeptides comprising, or alternatively consisting of, the amino acid sequences of a member selected from the group consisting of amino acids 1–60, 11–70, 21–80, 31–90, 41–100, 51–110, 61–120, 71–130, 81–140, 91–150, 101–160, 111–170, 121–180, 131–190, 141–200, 151–210, 161–220, 171–230, 181–240, 191–250, 201–260, 211–270, 221–280, 231–290, 241–300, 251–310, 261–320, 271–330, 281–340, 291–350, 301–360, 311–370, 321–380, 331–390, 341–400, and 351–401 of SEQ ID NO:2 or SEQ ID NO:4, as well as isolated polynucleotides which encode these polypeptides.

Among the especially preferred fragments of the invention are fragments characterized by structural or functional attributes of TR1. Such fragments include amino acid residues that comprise, or alternatively consist of, one, two, three, four, or more of the following functional domains: alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of full-length TR1 (SEQ ID NO:2). Certain preferred regions are those set out in FIG. 4 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou- Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

The data representing the structural or functional attributes of TR1 set forth in FIG. 4 and/or Table 2, as described above, was generated using the various identified modules and algorithms of the DNA*STAR set on default parameters. In a preferred embodiment, the data presented in columns VIII, IX, XIII, and XIV of Table 2 can be used to determine regions of TR1 which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 4, but may, as shown in Table 2, respectively, be represented or identified by using tabular representations of the data presented in FIG. 4. The DNA*STAR computer algorithm used to generate FIG. 4 (set on the original default parameters) was used to present the data in FIG. 4 in a tabular format (See Table 2). The tabular format of the data in FIG. 4 may be used to easily determine specific boundaries of a preferred region.

The above-mentioned preferred regions set out in FIG. 4 and in Table 2 include, but are not limited to, regions of the aforementioned types identified by analysis of the amino acid sequence set out in FIG. 1. As set out in FIG. 4 and in Table 2, such preferred regions include Garnier-Robson alpha-regions, beta-regions, turn-regions, and coil-regions; Chou-Fasman alpha-regions, beta-regions, and coil-regions; Kyte-Doolittle hydrophilic regions and hydrophobic regions; Eisenberg alpha- and beta-amphipathic regions; Karplus-Schulz flexible regions; Emini surface-forming regions; and Jameson-Wolf regions of high antigenic index.

The above-mentioned preferred regions set out in FIG. 4 and in Table 2 include, but are not limited to, regions of the aforementioned types identified by analysis of the amino acid sequence set out in FIG. 1. As set out in FIG. 4 and in Table 2, such preferred regions include Garnier-Robson alpha-regions, beta-regions, turn-regions, and coil-regions (columns I, III, V, and VII in Table 2), Chou-Fasman alpha-regions, beta-regions, and turn-regions (columns I, II, IV, and VI in Table 2), Kyte-Doolittle hydrophilic regions (column VIII in Table 2), Hopp-Woods hydrophobic regions (column IX in Table 2), Eisenberg alpha- and beta-amphipathic regions (columns X and XI in Table 2), Karplus-Schulz flexible regions (column XII in Table 2), Jameson-Wolf regions of high antigenic index (column XIII in Table 2), and Emini surface-forming regions (column XIV in Table 2).

The polypeptides of the present invention have uses that include, but are not limited to: use as a molecular weight marker on SDS-PAGE gels or on molecular sieve gel filtration columns using methods well-known to those of skill in the art.

As mentioned above, even if deletion of one or more amino acids from the N-terminus of a protein results in modification or loss of one or more biological functions of the protein, other biological activities may still be retained.

Thus, the ability of shortened TR1 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an TR1 mutein with a large number of deleted N-terminal amino acid residues may retain some biological or immunogenic activities. In fact, peptides composed of as few as six TR1 amino acid residues may often evoke an immune response.

Accordingly, the present invention further provides polypeptides having one or more residues deleted from the amino terminus of the TR1 amino acid sequence shown in FIGS. 1 and 2 (i.e., SEQ ID NO:2 and 4, respectively), up to the valine residue at position number 396 and polynucleotides encoding such polypeptides. In particular, the present invention provides polypeptides comprising the amino acid sequence of residues n-401 of FIG. 1 (SEQ ID NO:2), where n is an integer in the range of 2 to 396. The polypeptides having N-terminal deletions may also include an N-terminal methionine residue. Polynucleotides encoding these polypeptides are also encompassed by the invention.

More in particular, the invention provides polynucleotides encoding polypeptides comprising, or alternatively consisting of, the amino acid sequence of a member selected from the group consisting of, residues of N-2 to L-401; K-3 to L-401; L-4 to L-401; L-5 to L-401; C-6 to L-401; C-7 to L-401; A-8 to L-401; L-9 to L-401; V-10 to L-401; F-11 to L-401; L-12 to L-401; D-13 to L-401; L-14 to L-401; S-15 to L-401; L-16 to L-401; K-17 to L-401; W-18 to L-401; T-19 to L-401; T-20 to L-401; Q-21 to L-401; E-22 to L-401; T-23 to L-401; F-24 to L-401; P-25 to L-401; P-26 to L-401; K-27 to L-401; Y-28 to L-401; L-29 to L-401; H-30 to L-401; Y-31 to L-401; D-32 to L-401; E-33 to L-401; E-34 to L-401; T-35 to L-401; S-36 to L-401; H-37 to L-401; Q-38 to L-401; L-39 to L-401; L-40 to L-401; C-41 to L-401; D-42 to L-401; K-43 to L-401; C-44 to L-401; P-45 to L-401; P-46 to L-401; G-47 to L-401; T-48 to L-401; Y-49 to L-401; L-50 to L-401; K-51 to L-401; Q-52 to L-401; H-53 to L-401; C-54 to L-401; T-55 to L-401; A-56 to L-401; K-57 to L-401; W-58 to L-401; K-59 to L-401; T-60 to L-401; V-61 to L-401; C-62 to L-401; A-63 to L-401; P-64 to L-401; C-65 to L-401; P-66 to L-401; D-67 to L-401; H-68 to L-401; Y-69 to L-401; Y-70 to L-401; T-71 to L-401; D-72 to L-401; S-73 to L-401; W-74 to L-401; H-75 to L-401; T-76 to L-401; S-77 to L-401; D-78 to L-401; E-79 to L-401; C-80 to L-401; L-81 to L-401; Y-82 to L-401; C-83 to L-401; S-84 to L-401; P-85 to L-401; V-86 to L-401; C-87 to L-401; K-88 to L-401; E-89 to L-401; L-90 to L-401; Q-91 to L-401; Y-92 to L-401; V-93 to L-401; K-94 to L-401; Q-95 to L-401; E-96 to L-401; C-97 to L-401; N-98 to L-401; R-99 to L-401; T-100 to L-401; H-101 to L-401; N-102 to L-401; R-103 to L-401; V-104 to L-401; C-105 to L-401; E-106 to L-401; C-107 to L-401; K-108 to L-401; E-109 to L-401; G-110 to L-401; R-111 to L-401; Y-112 to L-401; L-113 to L-401; E-114 to L-401; I-115 to L-401; E-116 to L-401; F-117 to L-401; C-118 to L-401; L-119 to L-401; K-120 to L-401; H-121 to L-401; R-122 to L-401; S-123 to L-401; C-124 to L-401; P-125 to L-401; P-126 to L-401; G-127 to L-401; F-128 to L-401; G-129 to L-401; V-130 to L-401; V-131 to L-401; Q-132 to L-401; A-133 to L-401; G-134 to L-401; T-135 to L-401; P-136 to L-401; E-137 to L-401; R-138 to L-401; N-139 to L-401; T-140 to L-401; V-141 to L-401; C-142 to L-401; K-143 to L-401; R-144 to L-401; C-145 to L-401; P-146 to L-401; D-147 to L-401; G-148 to L-401; F-149 to L-401; F-150 to L-401; S-151 to L-401; N-152 to L-401; E-153 to L-401; T-154 to L-401; S-155 to L-401; S-156 to L-401; K-157 to L-401; A-158 to L-401; P-159 to L-401; C-160 to L-401; R-161 to L-401; K-162 to L-401; H-163 to L-401; T-164 to L-401; N-165 to L-401; C-166 to L-401; S-167 to L-401; V-168 to L-401; F-169 to L-401; G-170 to L-401; L-171 to L-401; L-172 to L-401; L-173 to L-401; T-174 to L-401; Q-175 to L-401; K-176 to L-401; G-177 to L-401; N-178 to L-401; A-179 to L-401; T-180 to L-401; H-181 to L-401; D-182 to L-401; N-183 to L-401; I-184 to L-401; C-185 to L-401; S-186 to L-401; G-187 to L-401; N-188 to L-401; S-189 to L-401; E-190 to L-401; S-191 to L-401; T-192 to L-401; Q-193 to L-401; K-194 to L-401; C-195 to L-401; G-196 to L-401; L-197 to L-401; D-198 to L-401; V-199 to L-401; T-200 to L-401; L-201 to L-401; C-202 to L-401; E-203 to L-401; E-204 to L-401; A-205 to L-401; F-206 to L-401; F-207 to L-401; R-208 to L-401; F-209 to L-401; A-210 to L-401; V-211 to L-401; P-212 to L-401; T-213 to L-401; K-214 to L-401; F-215 to L-401; T-216 to L-401; P-217 to L-401; N-218 to L-401; W-219 to L-401; L-220 to L-401; S-221 to L-401; V-222 to L-401; L-223 to L-401; V-224 to L-401; D-225 to L-401; N-226 to L-401; L-227 to L-401; P-228 to L-401; G-229 to L-401; T-230 to L-401; K-231 to L-401; V-232 to L-401; N-233 to L-401; A-234 to L-401; E-235 to L-401; S-236 to L-401; V-237 to L-401; E-238 to L-401; R-239 to L-401; L-240 to L-401; K-241 to L-401; R-242 to L-401; Q-243 to L-401; H-244 to L-401; S-245 to L-401; S-246 to L-401; Q-247 to L-401; E-248 to L-401; Q-249 to L-401; T-250 to L-401; F-251 to L-401; Q-252 to L-401; L-253 to L-401; L-254 to L-401; K-255 to L-401; L-256 to L-401; W-257 to L-401; K-258 to L-401; H-259 to L-401; Q-260 to L-401; N-261 to L-401; K-262 to L-401; D-263 to L-401; Q-264 to L-401; D-265 to L-401; L-266 to L-401; V-267 to L-401; K-268 to L-401; K-269 to L-401; L-270 to L-401; L-271 to L-401; Q-272 to L-401; D-273 to L-401; L-274 to L-401; D-275 to L-401; L-276 to L-401; C-277 to L-401; E-278 to L-401; N-279 to L-401; S-280 to L-401; V-281 to L-401; Q-282 to L-401; R-283 to L-401; H-284 to L-401; L-285 to L-401; G-286 to L-401; H-287 to L-401; A-288 to L-401; N-289 to L-401; L-290 to L-401; T-291 to L-401; F-292 to L-401; E-293 to L-401; Q-294 to L-401; L-295 to L-401; R-296 to L-401; S-297 to L-401; L-298 to L-401; M-299 to L-401; E-300 to L-401; S-301 to L-401; L-302 to L-401; P-303 to L-401; G-304 to L-401; K-305 to L-401; K-306 to L-401; V-307 to L-401; G-308 to L-401; A-309 to L-401; E-310 to L-401; D-311 to L-401; L-312 to L-401; E-313 to L-401; K-314 to L-401; T-315 to L-401; I-316 to L-401; K-317 to L-401; A-318 to L-401; C-319 to L-401; K-320 to L-401; P-321 to L-401; S-322 to L-401; D-323 to L-401; Q-324 to L-401; L-325 to L-401; L-326 to L-401; K-327 to L-401; L-328 to L-401; L-329 to L-401; S-330 to L-401; L-331 to L-401; W-332 to L-401; R-333 to L-401; L-334 to L-401; K-335 to L-401; N-336 to L-401; G-337 to L-401; D-338 to L-401; Q-339 to L-401; D-340 to L-401; T-341 to L-401; L-342 to L-401; K-343 to L-401; G-344 to L-401; L-345 to L-401; M-346 to L-401; H-347 to L-401; A-348 to L-401; L-349 to L-401; K-350 to L-401; H-351 to L-401; S-352 to L-401; K-353 to L-401; T-354 to L-401; Y-355 to L-401; H-356 to L-401; F-357 to L-401; P-358 to L-401; K-359 to L-401; T-360 to L-401; V-361 to L-401; T-362 to L-401; Q-363 to L-401; S-364 to L-401; L-365 to L-401; K-366 to L-401; K-367 to L-401; T-368 to L-401; L-369 to L-401; R-370 to L-401; F-371 to L-401; L-372 to L-401; H-373 to L-401; S-374 to L-401; F-375 to L-401; T-376 to L-401; M-377 to L-401; Y-378 to L-401; K-379 to L-401; L-380 to L-401; Y-381 to L-401; Q-382 to L-401; K-383 to L-401; L-384 to L-401; F-385 to L-401; L-386 to L-401; E-387 to L-401; M-388 to L-401; L-389 to L-401; G-390 to L-401; N-391 to L-401; Q-392 to L-401; V-393 to L-401; Q-394 to L-401; S-395 to L-401; and V-396 to L-401 of the TR1 sequence shown in FIG. 1 (which is identical to the sequence shown as SEQ ID NO:2, with the exception that the amino acid residues in FIG. 1 are numbered consecutively from 1 through 401 from the N-terminus to the C-terminus, while the amino acid residues in SEQ ID NO:2 are numbered consecutively from −21 through 380 to reflect the position of the predicted signal peptide). The polypeptides having N-terminal deletions may also include an N-terminal methionine residue.

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

In a preferred embodiment, polypeptides of the invention include TR1 polypeptides having a deletion of amino acids M-1 to Q-21 in FIG. 1. In other words, polypeptides of the invention include fragments having the amino acid sequence of E-22 to m, where m is an an integer in the range of 28 to 401. Fragments beginning at E-22 may also include an N-terminal methionine, thus having the sequence METF-PPK- to 401.

Also as mentioned above, even if deletion of one or more amino acids from the C-terminus of a protein results in modification or loss of one or more biological functions of the protein, other biological activities may still be retained. Thus, the ability of the shortened TR1 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an TR1 mutein with a large number of deleted C-terminal amino acid residues may retain some biological or immunogenic activities. In fact, peptides composed of as few as six TR1 amino acid residues may often evoke an immune response.

Accordingly, the present invention further provides polypeptides having one or more residues deleted from the carboxy terminus of the amino acid sequence of the TR1 polypeptide shown in FIG. 1 (SEQ ID NO:2), up to the cysteine residue at position number 6, and polynucleotides encoding such polypeptides. In particular, the present invention provides polypeptides comprising the amino acid sequence of residues 1-m of FIG. 1 (i.e., SEQ ID NO:2), where m is an integer in the range of 6 to 400.

More in particular, the invention provides polynucleotides encoding polypeptides comprising, or alternatively consisting of, the amino acid sequence of a member selected from the group consisting of residues M-1 to C-400; M-1 to S-399; M-1 to I-398; M-1 to K-397; M-1 to V-396; M-1 to S-395; M-1 to Q-394; M-1 to V-393; M-1 to Q-392; M-1 to N-391; M-1 to G-390; M-1 to I-389; M-1 to M-388; M-1 to E-387; M-1 to L-386; M-1 to F-385; M-1 to L-384; M-1 to K-383; M-1 to Q-382; M-1 to Y-381; M-1 to L-380; M-1 to K-379; M-1 to Y-378; M-1 to M-377; M-1 to T-376; M-1 to F-375; M-1 to S-374; M-1 to H-373; M-1 to L-372; M-1 to F-371; M-1 to R-370; M-1 to I-369; M-1 to T-368; M-1 to K-367; M-1 to K-366; M-1 to L-365; M-1 to S-364; M-1 to Q-363; M-1 to T-362; M-1 to V-361; M-1 to T-360; M-1 to K-359; M-1 to P-358; M-1 to F-357; M-1 to H-356; M-1 to Y-355; M-1 to T-354; M-1 to K-353; M-1 to S-352; M-1 to H-351; M-1 to K-350; M-1 to L-349; M-1 to A-348; M-1 to H-347; M-1 to M-346; M-1 to L-345; M-1 to G-344; M-1 to K-343; M-1 to L-342; M-1 to T-341; M-1 to D-340; M-1 to Q-339; M-1 to D-338; M-1 to G-337; M-1 to N-336; M-1 to K-335; M-1 to I-334; M-1 to R-333; M-1 to W-332; M-1 to L-331; M-1 to S-330; M-1 to L-329; M-1 to L-328; M-1 to K-327; M-1 to L-326; M-1 to I-325; M-1 to Q-324; M-1 to D-323; M-1 to S-322; M-1 to P-321; M-1 to K-320; M-1 to C-319; M-1 to A-318; M-1 to K-317; M-1 to I-316; M-1 to T-315; M-1 to K-314; M-1 to E-313; M-1 to I-312; M-1 to D-311; M-1 to E-310; M-1 to A-309; M-1 to G-308; M-1 to V-307; M-1 to K-306; M-1 to K-305; M-1 to G-304; M-1 to P-303; M-1 to L-302; M-1 to S-301; M-1 to E-300; M-1 to M-299; M-1 to L-298; M-1 to S-297; M-1 to R-296; M-1 to L-295; M-1 to Q-294; M-1 to E-293; M-1 to F-292; M-1 to T-291; M-1 to L-290; M-1 to N-289; M-1 to A-288; M-1 to H-287; M-1 to G-286; M-1 to I-285; M-1 to H-284; M-1 to R-283; M-1 to Q-282; M-1 to V-281; M-1 to S-280; M-1 to N-279; M-1 to E-278; M-1 to C-277; M-1 to L-276; M-1 to D-275; M-1 to I-274; M-1 to D-273; M-1 to Q-272; M-1 to I-271; M-1 to I-270; M-1 to K-269; M-1 to K-268; M-1 to V-267; M-1 to I-266; M-1 to D-265; M-1 to Q-264; M-1 to D-263; M-1 to K-262; M-1 to N-261; M-1 to Q-260; M-1 to H-259; M-1 to K-258; M-1 to W-257; M-1 to L-256; M-1 to K-255; M-1 to L-254; M-1 to L-253; M-1 to Q-252; M-1 to F-251; M-1 to T-250; M-1 to Q-249; M-1 to E-248; M-1 to Q-247; M-1 to S-246; M-1 to S-245; M-1 to H-244; M-1 to Q-243; M-1 to R-242; M-1 to K-241; M-1 to I-240; M-1 to R-239; M-1 to E-238; M-1 to V-237; M-1 to S-236; M-1 to E-235; M-1 to A-234; M-1 to N-233; M-1 to V-232; M-1 to K-231; M-1 to T-230; M-1 to G-229; M-1 to P-228; M-1 to L-227; M-1 to N-226; M-1 to D-225; M-1 to V-224; M-1 to L-223; M-1 to V-222; M-1 to S-221; M-1 to L-220; M-1 to W-219; M-1 to N-218; M-1 to P-217; M-1 to T-216; M-1 to F-215; M-1 to K-214; M-1 to T-213; M-1 to P-212; M-1 to V-211; M-1 to A-210; M-1 to F-209; M-1 to R-208; M-1 to F-207; M-1 to F-206; M-1 to A-205; M-1 to E-204; M-1 to E-203; M-1 to C-202; M-1 to L-201; M-1 to T-200; M-1 to V-199; M-1 to D-198; M-1 to I-197; M-1 to G-196; M-1 to C-195; M-1 to K-194; M-1 to Q-193; M-1 to T-192; M-1 to S-[91; M-1 to E-190; M-1 to S-189; M-1 to N-188; M-1 to G-187; M-1 to S-186; M-1 to C-185; M-1 to I-184; M-1 to N-183; M-1 to D-182; M-1 to H-181; M-1 to T-180; M-1 to A-179; M-1 to N-178; M-1 to G-177; M-1 to K-176; M-1 to Q-175; M-1 to T-174; M-1 to L-173; M-1 to L-172; M-1 to L-171; M-1 to G-170; M-1 to F-169; M-1 to V-168; M-1 to S-167; M-1 to C-166; M-1 to N-165; M-1 to T-164; M-1 to H-163; M-1 to K-162; M-1 to R-161; M-1 to C-160; M-1 to P-159; M-1 to A-158; M-1 to K-157; M-1 to S-156; M-1 to S-155; M-1 to T-154; M-1 to E-153; M-1 to N-152; M-1 to S-151; M-1 to F-150; M-1 to F-149; M-1 to G-]48; M-1 to D-147; M-1 to P-146; M-1 to C-145; M-1 to R-144; M-1 to K-143; M-1 to C-142; M-1 to V-141; M-1 to T-140; M-1 to N-139; M-1 to R-138; M-1 to E-137; M-1 to P-136; M-1 to T-135; M-1 to G-134; M-1 to A-133; M-1 to Q-132; M-1 to V-131; M-1 to V-130; M-1 to G-129; M-1 to F-128; M-1 to G-127; M-1 to P-126; M-1 to P-125; M-1 to C-124; M-1 to S-123; M-1 to R-122; M-1 to H-121; M-1 to K-120; M-1 to L-119; M-1 to C-118; M-1 to F-117; M-1 to E-116; M-1 to I-115; M-1 to E-114; M-1 to L-113; M-1 to Y-112; M-1 to R-111; M-1 to G-110; M-1 to E-109; M-1 to K-108; M-1 to C-107; M-1 to E-106; M-1 to C-105; M-1 to V-104; M-1 to R-103; M-1 to N-102; M-1 to H-101; M-1 to T-100; M-1 to R-99; M-1 to N-98; M-1 to C-97; M-1 to E-96; M-1 to Q-95; M-1 to K-94; M-1 to V-93; M-1 to Y-92; M-1 to Q-91; M-1 to L-90; M-1 to E-89; M-1 to K-88; M-1 to C-87; M-1 to V-86; M-1 to P-85; M-1 to S-84; M-1 to C-83; M-1 to Y-82; M-1 to L-81; M-1 to C-80; M-1 to E-79; M-1 to D-78; M-1 to S-77; M-1 to T-76; M-1 to H-75; M-1 to W-74; M-1 to S-73; M-1 to D-72; M-1 to T-71; M-1 to Y-70; M-1 to Y-69; M-1 to H-68; M-1 to D-67; M-1 to P-66; M-1 to C-65; M-1 to P-64; M-1 to A-63; M-1 to C-62; M-1 to V-61; M-1 to T-60; M-1 to K-59; M-1 to W-58; M-1 to K-57; M-1 to A-56; M-1 to T-55; M-1 to C-54; M-1 to H-53; M-1 to Q-52; M-1 to K-51; M-1 to L-50; M-1 to Y-49; M-1 to T-48; M-1 to G-47; M-1 to P-46; M-1 to P-45; M-1 to C-44; M-1 to K-43; M-1 to D-42; M-1 to C-41; M-1 to L-40; M-1 to L-39; M-1 to Q-38; M-1 to H-37; M-1 to S-36; M-1 to T-35; M-1 to E-34; M-1 to E-33; M-1 to D-32; M-1 to Y-31; M-1 to H-30; M-1 to L-29; M-1 to Y-28; M-1 to K-27; M-1 to P-26; M-1 to P-25; M-1 to F-24; M-1 to T-23; M-1 to E-22; M-1 to Q-21; M-1 to T-20; M-1 to T-19; M-1 to W-18; M-1 to K-17; M-1 to I-16; M-1 to S-15; M-1 to I-14; M-1 to D-13; M-1 to L-12; M-1 to F-11; M-1 to V-10; M-1 to L-9; M-1 to A-8; M-1 to C-7; and M-1 to C-6 of the sequence of the TR1 sequence shown in FIG. 1 (which is identical to the sequence shown as SEQ ID NO:2, with the exception that the amino acid residues in FIG. 1 are numbered consecutively from 1 through 401 from the N-terminus to the C-terminus, while the amino acid residues in SEQ ID NO:2 are numbered consecutively from −21 through 380 to reflect the position of the predicted signal peptide).

The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of an TR1 polypeptide, which may be described generally as having residues n-m of FIG. 1 (i.e., SEQ ID NO:2), where n and m are integers as described above. The polypeptides having N- and C-terminal deletions may also include an N-terminal methionine residue.

In certain preferred embodiments, TR1 polypeptides of the invention comprise fusion proteins as described above wherein the TR1 polypeptides are those described as n-m herein. In preferred embodiments, the application is directed to nucleic acid molecules at least 90%, 95%, 96%, 97%, 98% or 99% identical to the nucleic acid sequences encoding polypeptides having the amino acid sequence of the specific N- and C-terminal deletions recited herein. Polynucleotides encoding these polypeptides are also encompassed by the invention.

The TR1 polypeptides of the invention may be in monomers or multimers (i.e., dimers, trimers, tetramers and higher multimers). Accordingly, the present invention relates to monomers and multimers of the TR1 polypeptides of the invention, their preparation, and compositions (preferably pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only TR1 polypeptides of the invention (including TR1 fragments, variants, and fusion proteins, as described herein). These homomers may contain TR1 polypeptides having identical or different amino acid sequences. In a specific embodiment, a homomer of the invention is a multimer containing only TR1 polypeptides having an identical amino acid sequence. In another specific embodiment, a homomer of the invention is a multimer containing TR1 polypeptides having different amino acid sequences. In specific embodiments, the multimer of the invention is a homodimer (e.g., containing TR1 polypeptides having identical or different amino acid sequences) or a homotrimer (e.g., containing TR1 polypeptides having identical or different amino acid sequences). In additional embodiments, the homomeric multimer of the invention is at least a homodimer, at least a homotrimer, or at least a homotetramer.

As used herein, the term heteromer refers to a multimer containing heterologous polypeptides (i.e., polypeptides of a different protein) in addition to the TR1 polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, for example, by liposome formation. Thus, in one embodiment, multimers of the invention such as, for example, homodimers or homotrimers, are formed when polypeptides of the invention contact one another in solution. In another embodiment, heteromultimers of the invention such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the TR1 polypeptides of the invention. Such covalent associations may involve one or more amino acid residues contained in the polypeptide sequence (e.g., that recited in SEQ If) NO:2 or SEQ ID NO:4, or that encoded by the deposited clone). In one instance, the covalent associations are cross-links between cysteine residues which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR1 fusion protein. In one example, covalent associations are between the heterologous sequence contained in a fusion protein of the invention (see, e.g., U.S. Pat. No. 5,478,925). In a specific example, the covalent associations are between the heterologous sequence contained in a TR1-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., International Publication No. WO 98/49305, the contents of which are herein incorporated by reference in its entirety).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In addition, polypeptides of the invention can be chemically synthesized using techniques known in the art (e.g., see, Creighton, 1983, *Proteins: Structures and Molecular Principles*, W.H. Freeman & Co., N.Y.; and Hunkapiller, M., et al., 1984, *Nature* 310:105–111). For example, a peptide corresponding to a fragment of the TR1 polypeptides of the invention can be synthesized by use of a peptide synthesizer. Furthermore, if desired, nonclassical amino acids or chemical amino acid analogs can be introduced as a substitution or addition into the TR1 polynucleotide sequence. Non-classical amino acids include, but are not limited to, the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses TR1 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, N-linked or O-linked carbohydrate chains, processing of N- or C-termini, attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label, to allow for detection and isolation of the protein.

Also provided by the invention are chemically modified derivatives of TR1 which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000,12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art. See, e.g., EP 0 401 384, (coupling PEG to G-CSF) (herein incorporated by reference); Malik et al., *Exp. Hematol.* 20:1028–1035 (1992) (reporting pegylation of GM-CSF using tresyl chloride). For example, polyethylene glycol may be covalently bound to amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching polyethylene glycol molecules. Preferred for therapeutic purposes is attachment at an amino group, such as attachment at the N-terminus or at a lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecule types (by molecular weight, branching, etc.), a range of proportions of polyethylene glycol molecules to protein (or peptide) molecules in the reaction mix, types of pegylation reactions, and methods of obtaining the desired N-terminally pegylated protein. The method of obtaining the N-terminally pegylated preparation (i.e., separating this moiety from other monopegylated moieties if necessary) may be by purification of the N-terminally pegylated material from a population of pegylated protein molecules. N-terminal modification may be accomplished by reductive alkylation which exploits differential reactivity of different types of primary amino groups (on lysine versus at the N-terminus) available for derivatization in a particular protein. Under the appropriate reaction conditions, substantially selective derivatization at the N-terminus with a carbonyl group-containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., Crit. Rev. Thera. Drug Carrier Sys. 9:249–304 (1992).

The entire disclosure of each document cited in this section on "TR1 Receptor Polypeptides and Fragments" is hereby incorporated herein by reference.

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the nucleic acid sequences of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pHE4, pBS, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, Bennett et al., *Journal of Molecular Recognition,* 8:52–58 (1995) and Johanson et al., *The Journal of Biological Chemistry,* 270: 9459–9471 (1995).

The TR1 receptor protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TR1 coding sequence), and/or to include genetic material (e.g., heterologous polynucleotide sequences) that is operably associated with TR1 polynucleotides of the invention, and which activates, alters, and/or amplifies endogenous TR1 polynucleotides. For example, techniques known in the art may be used to operably associate heterologous control regions (e.g., promoter and/or enhancer) and endogenous TR1 polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

TR1 Receptor: Use for Detection of Disease States

The inventors have shown that the TR1 receptor of the present invention binds both TNF-α and TNF-β but has a higher affinity for TNF-β. See FIG. 7. TNF-β, a potent ligand of the TNF receptor proteins, is known to be involved in a number of biological processes including lymphocyte development, tumor necrosis, induction of an antiviral state, activation of polymorphonuclear leukocytes, induction of class I major histocompatibility complex antigens on endothelial cells, induction of adhesion molecules on endothelium and growth hormone stimulation (Ruddle and Homer, *Prog. Allergy,* 40:162–182 (1988)). TNF-α, also a ligand of the TR1 receptors of the present invention, has been reported to have a role in the rapid necrosis of tumors, immunostimulation, autoimmune disease, graft rejection, producing an anti-viral response, septic shock, cerebral malaria, cytotoxicity, protection against deleterious effects of ionizing radiation produced during a course of chemotherapy, such as denaturation of enzymes, lipid peroxidation and DNA damage (Nata et al., *J. Immunol.* 136(7):2483 (1987)), growth regulation, vascular endothelium effects and metabolic effects. TNF-α also triggers endothelial cells to secrete various factors, including PAI-1, IL-1, GM-CSF and IL-6 to promote cell proliferation. In addition, TNF-α up-regulates various cell adhesion molecules such as E-Selectin, ICAM-1 and VCAM-1. TNF-α and the Fas ligand have also been shown to induce programmed cell death.

It is believed that certain tissues in mammals with specific cancers express significantly altered levels of the TR1 receptor protein and mRNA encoding the TR1 receptor protein when compared to a corresponding "standard" mammal, i.e., a mammal of the same species not having the cancer. For example, the inventors have found that osteosarcoma, ovarian carcinoma, monocyte leukemia, and lung emphysemia cells express the TR1 receptor protein of the present invention. Further, since this protein is secreted, it is believed that enhanced levels of the TR1 receptor protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis and possibly other disease states, which involves assaying the expression level of the gene encoding the TR1 receptor protein in mammalian cells or body fluid and comparing the gene expression level with a standard TR1 receptor gene expression level, whereby an increase or decrease in the gene expression level over the standard is indicative of certain tumors.

Where a tumor diagnosis has already been made according to conventional methods, the present invention is useful as a prognostic indicator, whereby patients exhibiting significantly enhanced TR1 receptor gene expression will experience a worse clinical outcome relative to patients expressing the gene at a lower level.

By "assaying the expression level of the gene encoding the TR1 receptor protein" is intended qualitatively or quantitatively measuring or estimating the level of the TR1 receptor protein or the level of the mRNA encoding the TR1 receptor protein in a first biological sample either directly (e.g., by determining or estimating absolute protein level or mRNA level) or relatively (e.g., by comparing to the TR1 receptor protein level or mRNA level in a second biological sample).

Preferably, the TR1 receptor protein level or mRNA level in the first biological sample is measured or estimated and compared to a standard TR1 receptor protein level or mRNA level, the standard being taken from a second biological sample obtained from an individual not having the cancer. As will be appreciated in the art, once a standard TR1 receptor protein level or mRNA level is known, it can be used repeatedly as a standard for comparison.

By "biological sample" is intended any biological sample obtained from an individual, cell line, tissue culture, or other source which contains TR1 receptor protein or mRNA. Biological samples include mammalian body fluids (such as sera, plasma, urine, synovial fluid and spinal fluid) which contain secreted mature TR1 receptor protein, and thymus, prostate, heart, placenta, muscle, liver, spleen, lung, kidney and umbilical tissue. Methods for obtaining tissue biopsies and body fluids from mammals are well known in the art. Where the biological sample is to include mRNA, a tissue biopsy is the preferred source.

The present invention is useful for detecting cancer and other disease states in mammals. In particular the invention is useful during diagnosis of cancer resulting from the proliferation of osteoblastoma cells. As described in Example 7, Northern blot analysis has shown that osteoblastoma cells, in addition to a number of normal tissues, have been found to express the TR1 receptor of the present invention. This result, when coupled with the fact that synovial sarcoma cells do not produce detectable levels of TR1 receptor mRNA, indicates that the molecules provided by the present invention may be useful for both detecting certain disease states as well as providing a treatment for such states. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, Anal. Biochem. 162: 156–159 (1987). Levels of mRNA encoding the TR1 receptor protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Example 7 below and in Harada et al., Cell 63:303–312 (1990). Briefly, total RNA is prepared from a biological sample as described above. For the Northern blot, the RNA is denatured in an appropriate buffer (such as, glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. TR1 receptor protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., Cell 49:357–367 (1987). To prepare probe DNA for use in S1 mapping, the sense strand of above-described cDNA is used as a template to synthesize labeled anti sense DNA. The antisense DNA can then be digested using an appropriate restriction endonuclease to generate further DNA probes of a desired length. Such antisense probes are useful for visualizing protected bands corresponding to the target mRNA (i.e., mRNA encoding the TR1 receptor protein). Northern blot analysis can be performed as described above.

Preferably, levels of mRNA encoding the TR1 receptor protein are assayed using the RT-PCR method described in Makino et al., Technique 2:295–301 (1990). By this method, the radio activities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the TR1 receptor protein)) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying TR1 receptor protein levels in a biological sample can occur using any art-known method. Preferred for assaying TR1 receptor protein levels in a biological sample are antibody-based techniques. For example, TR1 receptor protein expression in tissues can be studied with classical immunohistological methods. In these, the specific recognition is provided by the primary antibody (polygonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of TR1 receptor protein for Western-blot or dot/slot assay (Jalkanen., et al., J. Cell. Biol. 101:976–985 (1985); Jalkanen, et al., J. Cell. Biol. 105:3087–3096 (1987)). In this technique, which is based on the use of cationic solid phases, quantitation of TR1 receptor protein can be accomplished using isolated TR1 receptor protein as a standard. This technique can also be applied to body fluids. With these samples, a molar concentration of TR1 receptor protein will aid to set standard values of TR1 receptor protein content for different body fluids, like serum, plasma, urine, spinal fluid, etc. The normal appearance of TR1 receptor protein amounts can then be set using values from healthy individuals, which can be compared to those obtained from a test subject.

Thus, from the above, the present invention further relates to a diagnostic assay which detects an altered level of a soluble form of the polypeptide of the present invention where an elevated level in a sample derived from a host is indicative of certain diseases.

Assays available to detect levels of soluble receptors are well known to those of skill in the art, for example, radioimmunoassays, competitive-binding assays, Western blot analysis, and preferably an ELISA assay may be employed.

An ELISA assay initially comprises preparing an antibody specific to an antigen to the polypeptide of the present invention, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g., a polystyrene dish, that binds the proteins in the sample. Any free protein binding sites on the dish are then covered by incubating with a non-specific protein such as bovine serum albumen. Next, the monoclonal antibody is incubated in the dish during which time the monoclonal antibodies attach to any proteins of the present invention which are attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the protein of interest present in a given volume of patient sample when compared against a standard curve.

A competition assay may be employed wherein antibodies specific to the polypeptides of the present invention are attached to a solid support. Labeled TR1 receptor polypeptides, and a sample derived from the host are passed over the solid support and the amount of label detected attached to the solid support can be correlated to a quantity in the sample. The soluble form of the receptor may also be employed to identify agonists and antagonists.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying TR1 receptor protein levels in a biological sample obtained from an individual, TR1 receptor protein can also be detected in vivo by imaging. Antibody labels or markers for in vivo imaging of TR1 receptor protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TR1 receptor protein-specific antibody or antibody fragment which has been labeled with an appropriate detectable imaging moiety, such as a radioisotope (for example, $^{131}$I, $^{112}$I, $^{99m}$Tc), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TR1 receptor protein. In vivo tumor imaging is described in S. W. Burchiel et al., "Immunopharmacokinetics of Radiolabelled Antibodies and Their Fragments" (Chapter 13 in *Tumor Imaging. The Radiochemical Defection of Cancer*, S. W. Burchiel and B. A. Rhodes, eds., Masson Publishing Inc. (1982)).

TR1 receptor-protein specific antibodies for use in the present invention can be raised against the intact TR1 receptor protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to TR1 receptor protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the TR1 receptor protein or an antigenic fragment thereof can be administered to an animal in order to induce the production of sera containing polyclonal antibodies. In a preferred method, a preparation of TR1 receptor protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or TR1 receptor protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563–681). In general, such procedures involve immunizing an animal (preferably a mouse) with a TR1 receptor protein antigen or, more preferably, with a TR1 receptor protein-expressing cell. Suitable cells can be recognized by their capacity to bind anti-TR1 receptor protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Manassas, Va. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the TR1 receptor protein antigen.

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

Alternatively, additional antibodies capable of binding to the TR1 receptor protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, TR1 receptor-protein specific antibodies are used to immunize an animal, preferably a mouse. The splenocytes of such an animal are then used to produce hybridoma cells, and the hybridoma cells are screened to identify clones which produce an antibody whose ability to bind to the TR1 receptor protein-specific antibody can be blocked by the TR1 receptor protein antigen. Such antibodies comprise anti-idiotypic antibodies to the TR1 receptor protein-specific antibody and can be used to immunize an animal to induce formation of further TR1 receptor protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, TR1 receptor protein-binding fragments can be produced through the application of recombinant DNA technology or through synthetic chemistry.

Where in vivo imaging is used to detect enhanced levels of TR1 receptor protein for tumor diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229.1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Bouilanne et al., *Nature* 312:643 (1984); Neuberger et al., *Nature* 314:268 (1985).

Further suitable labels for the TR1 receptor protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$SC, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl Med.* 10:296–301 (1985); Carasquillo et al., *J. Nucl. Med.* 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med* 28:861–870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

TR1 Receptor Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. Thus, the invention further relates to antibodies which act as agonists or antagonists of the polypeptides of the present invention. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161(4):1786–1794 (1998); Zhu et al., Cancer Res. 58(15):3209–3214 (1998); Yoon et al., J. Immunol 160(7):3170–3179 (1998); Prat et al., J. Cell. Sci. 111(Pt2):237–247 (1998); Pitard et al., J. Immunol. Methods 205(2): 177–190 (1997); Liautard et al., Cytokine 9(4): 233–241 (1997); Carlson et al., J. Biol. Chem. 272(17): 11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Methods for producing and screening for specific antibodies using hybridoma technology are routine and well-known in the art and are discussed in detail in Example 8. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., *J. Immunol. Methods* 184: 177–186 (1995); Kettleborough et al., *Eur. J. Immunol* 24:952–958 (1994); Persic et al., *Gene* 187:9–18 (1997); Burton et al., *Advances in Immunology* 57: 191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864–869 (1992); and Sawai et al., *AJRI* 34:26–34 (1995); and Better et al, Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., (1989) *J. Immunol Methods* 125:191–202; U.S. Pat. Nos. 5,807,715; 4,816,567; and 4,816,397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5): 489–498 (1991); Studnicka et al., Protein Engineering 7(6): 805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437–444 (1989) and Nissinoff, *J. Immunol.* 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

A. Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 or SEQ ID NO:4.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851–855; Neuberger et al., 1984, Nature 312:604–608; Takeda et al., 1985, Nature 314:452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423–42; Huston et al., 1988, Proc. Natl. Acad. Sci. USA 85:5879–5883; and Ward et al, 1989, Nature 334:544–54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, Science 242:1038–1041).

B. Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al, 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 24:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153 51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al, 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIB TECH 11(5):155–215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, *Nature* 322:52 (1986); Kohler, *Proc. Natl. Acad. Sci. USA* 77:2197 (1980). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

C. Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.* 39:91–99 (1994); U.S. Pat. No. 5,474,981; Gillies et al., *PNAS* 89:1428–1432 (1992); Fell et al., *J. Immunol.* 146:2446–2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.* 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5 receptor, have been fused with Fc portions for the purpose of high-throughput screening assays to identify antagonists of hIL-5. (See, D. Bennett et al., *J. Molecular Recognition* 8:52–58 (1995); K. Johanson et al., *J. Biol. Chem.* 270:9459–9471 (1995).

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

D. Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer; blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

TR1 Receptor: Therapeutic Uses

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," *Symp. Quant. Biol.* 51:597–609 (1986), Cold Spring Harbor; Beutler, B., and Cerami, A., *Annu. Rev. Biochem.* 57:505–518 (1988); Old, L. J., *Sci. Am.* 258:59–75 (1988); Fiers, W., *FEBS Lett.* 285:199–224 (1991)). The TNF-family ligands induce such various cellular responses by binding to TNF-family receptors.

TR1 receptor polynucleotides, polypeptides, agonists or antagonists of the invention may be used in developing treatments for any disorder mediated (directly or indirectly) by defective, or insufficient amounts of TR1 receptor. TR1 receptor polypeptides, agonists or antagonists may be administered to a patient (e.g., mammal, preferably human) afflicted with such a disorder. Alternatively, a gene therapy approach may be applied to treat such disorders. Disclosure herein of TR1 receptor nucleotide sequences permits the detection of defective TR1 receptor genes, and the replacement thereof with normal TR1 receptor-encoding genes. Defective genes may be detected in in vitro diagnostic assays, and by comparison of the TR1 receptor nucleotide sequence disclosed herein with that of a TR1 receptor gene derived from a patient suspected of harboring a defect in this gene.

In another embodiment, the polypeptides of the present invention are used as a research tool for studying the biological effects that result from inhibiting OPGL/TR1 receptor and/or TRAIL/TR1 receptor interactions on different cell types. TR1 receptor polypeptides also may be employed in in vitro assays for detecting TRAIL, OPGL or TR1 receptor or the interactions thereof.

In another embodiment, a purified TR1 receptor polypeptide or antagonist is used to inhibit binding of detecting TRAIL or OPGL to endogenous cell surface detecting TRAIL and/or OPGL receptors. Certain ligands of the TNF family (of which detecting TRAIL and OPGL are members) have been reported to bind to more than one distinct cell surface receptor protein. TRAIL likewise has been shown to bind multiple cell surface proteins. By binding TRAIL and/or OPGL, soluble TR1 receptor polypeptides of the present invention may be employed to inhibit the binding of TRAIL and/or OPGL not only to cell surface TR1 receptor, but also to TRAIL and/or OPGL receptor proteins that are distinct from TR1 receptor. Thus, in another embodiment, TR1 receptor polynucleotides, polypeptides, agonists or antagonists is used to inhibit a biological activity of TRAIL and/or OPGL, in in vitro or in vivo procedures. By inhibiting binding TRAIL and/or OPGL to cell surface receptors, TR1 receptor polynucleotides, polypeptides, agonists or antagonists also inhibit biological effects that result from the binding of TRAIL and/or OPGL to endogenous receptors. Various forms of TR1 receptor may be employed, including, for example, the above-described TR1 receptor fragments, derivatives, and variants that are capable of binding TRAIL and/or OPGL. In one preferred embodiment, a soluble TR1 receptor polypeptide is employed to inhibit a biological activity of TRAIL, e.g., to inhibit TRAIL-mediated apoptosis of cells susceptible to such apoptosis. In another preferred embodiment, a soluble TR1 receptor polypeptide is employed to inhibit a biological activity of OPGL (e.g., stimulation of osteoclast differentiation, and lymphocyte activation).

In a further embodiment, a TR1 receptor polynucleotide, polypeptide, agonist or antagonist is administered to a mammal (e.g., a human) to treat a TRAIL-mediated and/or OPGL mediated disorder. Such TRAIL-mediated and/or OPGL mediated disorders include conditions caused (directly or indirectly) or exacerbated by TRAIL and/or OPGL.

Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. In preferred embodiments, TR1 receptor polynucleotides, polypeptides, agonists, or antagonists of the invention are used to inhibit growth, progression, and/or metastasis of cancers, in particular those listed above or in the paragraph that follows.

Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Grave's disease Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis) myelodysplastic syndromes (such as aplastic anemia), graft vs. host disease (acute and/or chronic), ischemic injury (such as that caused by myocardial infarction, stroke and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia and anorexia. In preferred embodiments, TR1 receptor polynucleotides, polypeptides, agonists, and/or antagonists are used to treat the diseases and disorders listed above.

HIV

Many of the pathologies associated with HIV are mediated by apoptosis, including HIV-induced nephropathy and HIV encephalitis. Thus, in additional preferred embodiments, TR1 receptor polynucleotides, polypeptides, agonists, or antagonists of the invention are used to treat AIDS and pathologies associated with AIDS.

Another embodiment of the present invention is directed to the use of TR1 receptor polynucleotides, polypeptides, agonists or antagonists to reduce TRAIL-mediated death of T cells in HIV-infected patients. The role of T cell apoptosis in the development of AIDS has been the subject of a number of studies (see, for example, Meyaard et al., *Science* 257:217–219 (1992); Groux et al., *J. Exp. Med.*, 175:331 (1992); and Oyaizu et al., in *Cell Activation and Apoptosis in HIV infection*, Andrieu and Lu, Eds., Plenum Press, New York (1995), pp. 101–114). Fas-mediated apoptosis has been implicated in the loss of T cells in HIV individuals (Katsikis et al., *J. Exp. Med* 181:2029–2036, 1995). It is also likely that T cell apoptosis occurs through multiple mechanisms. For example, at least some of the T cell death seen in HIV patients is likely to be mediated by TRAIL.

Activated human T cells are induced to undergo programmed cell death (apoptosis) upon triggering through the CD3/T cell receptor complex, a process termed activated-induced cell death (AICD). AICD of CD4 T cells isolated from HIV-Infected asymptomatic individuals has been reported (Groux et al., supra). Thus, AICD may play a role in the depletion of CD4+ T cells and the progression to AIDS in HIV-infected individuals. Thus, the present invention provides a method of inhibiting TRAIL-mediated T cell death in HIV patients, comprising administering a TR1 receptor polynucleotides, polypeptides, agonists or antagonists of the invention (preferably, a soluble TR1 receptor polypeptide) to the patients. In one embodiment, the patient is asymptomatic when treatment with TR1 receptor polynucleotides, polypeptides, agonists or antagonists commences. If desired, prior to treatment, peripheral blood T cells may be extracted from an HIV patient, and tested for susceptibility to TRAIL-mediated cell death by procedures known in the art. In one embodiment, a patient's blood or plasma is contacted with TR1 receptor polypeptides of the invention ex vivo. The TR1 receptor polypeptides may be bound to a suitable chromatography matrix by procedures known in the art. The patient's blood or plasma flows through a chromatography column containing TR1 receptor polypeptide bound to the matrix, before being returned to the patient. The immobilized TR1 receptor polypeptide binds TRAIL, thus removing TRAIL protein from the patient's blood.

In additional embodiments a TR1 receptor polynucleotide, polypeptide, agonist or antagonist of the invention is administered in combination with other inhibitors of T cell apoptosis. For example, as discussed above, Fas-mediated apoptosis also has been implicated in loss of T cells in HIV individuals (Katsikis et al., *J. Exp. Med.* 181:2029–2036 (1995)). Thus, a patient susceptible to both Fas ligand mediated and TRAIL mediated T cell death may be treated with both an agent that blocks TRAIL/TRAIL receptor interactions and an agent that blocks Fas-ligand/Fas interactions. Suitable agents for blocking binding of Fas-ligand to Fas include, but are not limited to, soluble Fas polypeptides; mulitmeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in International application publication number WO 95/10540, hereby incorporated by reference.

In another example, agents, which block binding of TRAIL to a TRAIL receptor, are administered with the TR1 receptor polynucleotides, polypeptides, agonists, or antagonists of the invention. Such agents include, but are not limited to, soluble TRAIL receptor polypeptides (e.g., DR4 (International application publication number WO 98/32856); TR5 (International application publication number WO 98/30693); DR5 (International application publication number WO 98/41629); and TR10 (International application publication number WO 98/54202)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

Cardiovascular Disorders

TR1 receptor polynucleotides, polypeptides, agonists, or antagonists of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, post-pericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In one embodiment, a TR1 receptor polynucleotide, polypeptide, agonist, or antagonist of the invention is used to treat thrombotic microangiopathies. One such disorder is thrombotic thrombocytopenic purpura (TTP) (Kwaan, H. C., *Semin. Hematol* 24:71 (1987); Thompson et al., *Blood* 80:1890 (1992)). Increasing TTP-associated mortality rates have been reported by the U.S. Centers for Disease Control (Torok et al., *Am. J. Hematol.* 50:84 (1995)). Plasma from patients afflicted with TTP (including HIV+ and HIV− patients) induces apoptosis of human endothelial cells of dermal microvascular origin, but not large vessel origin (Laurence et al., *Blood* 87:3245 (1996)). Plasma of TTP patients thus is thought to contain one or more factors that directly or indirectly induce apoptosis. Another thrombotic microangiopathy is hemolytic-uremic syndrome (HUS) (Moake, J. L., *Lancet*, 343:393, 1994; Melnyk et al., (*Arch. Intern. Med*, 155:2077, 1995; Thompson et al., supra). Thus, in one embodiment, the invention is directed to use of TR1 receptor to treat the condition that is often referred to as "adult HUS" (even though it can strike children as well). A disorder known as childhood/diarrhea-associated HUS differs in etiology from adult HUS. In another embodiment, conditions characterized by clotting of small blood vessels may be treated using TR1 receptor. Such conditions include, but are not limited to, those described herein. For example, cardiac problems seen in about 5–10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated. In one embodiment, a patient's blood or plasma is contacted with TR1 receptor polypeptides of the invention ex vivo. The TR1 receptor polypeptides of the invention may be bound to a suitable chromatography matrix by procedures known in the art. According to this embodiment, the patient's blood or plasma flows through a chromatography column containing TR1 receptor polynucleotides and/or polypeptides of the invention bound to the matrix, before being returned to the patient. The immobilized TR1 receptor binds TRAIL, thus removing TRAIL protein from the patient's blood. Alternatively, TR1 receptor polynucleotides, polypeptides, agonists or antagonists of the invention may be administered in vivo to a patient afflicted with a thrombotic microangiopathy. In one embodiment, a soluble form of TR1 receptor polypeptide of the invention is administered to the patient. Thus, the present invention provides a method for treating a thrombotic microangiopathy, involving use of an effective amount of TR1 receptor polynucleotide, polypeptide, agoniss or antagonist. A TR1 receptor polypeptide may be employed in in vivo or ex vivo procedures, to inhibit TRAIL-mediated damage to (e.g., apoptosis of) microvascular endothelial cells.

TR1 receptor polynucleotides, polypeptides, agonists or antagonists of the invention may be employed in combination with other agents useful in treating a particular disorder. For example, in an in vitro study reported by Laurence et al. (*Blood* 87:3245 (1996)), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated with a polynucleotide and/or polypeptide of the invention in combination with an agent that inhibits Fas-ligand-mediated apoptosis of endothelial cells, such as, for example, an agent described above. In one embodiment, a TR1 receptor polynucleotide, polypeptide, agonist or antagonist, and an anti-FAS blocking antibody are both administered to a patient afflicted with a disorder characterized by thrombotic microanglopathy, such as TTP or HUS. Examples of blocking monoclonal antibodies directed against Fas antigen (CD95) are described in International patent application publication number WO 95/10540, hereby incorporated by reference.

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.*, 333:1757–1763 (1995); Auerbach et al., *J. Microvasc. Res.* 29:401–411 (1985); Folkman, *Advances in Cancer Research*, eds. Klein and Weinhouse, Academic Press, New York, pp. 175–203 (1985); Patz, *Am. J. Opthalmol.* 94:715–743 (1982); and Folkman et al, *Science*

221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the TR1 receptor polynucleotides and/or polypeptides of the invention (including TR1 receptor agonists and/or antagonists). Malignant and metastatic conditions which can be treated with the polynucleotides and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)).

Additionally, ocular disorders associated with neovascularization which can be treated with the TR1 receptor polynucleotides and polypeptides of the present invention (including TR1 receptor agonists and TR1 receptor antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Additionally, disorders which can be treated with the TR1 receptor polynucleotides and polypeptides of the present invention (including TR1 receptor agonists and TR1 receptor antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

TR1 receptor: Use in Diagnosis, Prognosis, Treatment, or Prevention

Polynucleotides and/or polypeptides of the invention, and/or agonists and/or antagonists thereof, are useful in the diagnosis, prognosis, treatment or prevention of a wide range of diseases and/or conditions. Such diseases and conditions include, but are not limited to, cancer (e.g., immune cell related cancers, breast cancer, prostate cancer, ovarian cancer, follicular lymphoma, glioblastoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy and lymphomas (e.g., EBVinduced lymphoproliferations and Hodgkin's disease), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, myasthenia gravis, rheumatoid arthritis, systemic lupus erythematosus, immune complex glomerulonephritis, autoimmune diabetes, autoimmune thrombocytopenic purpura, Grave's disease, Hashimoto's thyroiditis, inflammatory autoimmune diseases, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures), and regulating bone formation and treating osteoporosis.

Polynucleotides and/or polypeptides of the invention and/or agonists and/or antagonists thereof are also useful as an adjuvant to enhance immune responsiveness to specific antigen and/or anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders or in the prevention of transplant rejection. In specific embodiments, polynucleotides and/or polypeptides of the invention are used to treat or prevent chronic inflammatory, allergic or autoimmune conditions, such as those described herein or are otherwise known in the art.

TR1 Receptor: Use for Screening for Agonists and Antagonists of TR1 Receptor Function In one aspect, the present invention is directed to a method for enhancing an activity (e.g., cell proliferation, hematopoietic development, apoptosis) of a TR1 receptor of the present invention, which involves administering to a cell which expresses a TR1 receptor polypeptide an effective amount of an agonist capable of increasing TR1 receptor mediated signaling. Preferably, TR1 receptor mediated signaling is increased to treat a disease.

In a further aspect, the present invention is directed to a method for inhibiting an activity of a TR1 receptor of the present invention, which involves administering to a cell which expresses the TR1 receptor polypeptide an effective amount of an antagonist capable of decreasing TR1 receptor mediated signaling. Preferably, TR1 receptor mediated signaling is decreased to also treat a disease.

By "agonist" is intended naturally occurring and synthetic compounds capable of enhancing or potentiating an activity of a TR1 receptor of the present invention. By "antagonist" is intended naturally occurring and synthetic compounds capable of inhibiting an activity of a TR1 receptor. Whether any candidate "agonist" or "antagonist" of the present invention can enhance or inhibit an activity can be determined using art-known TR1-family ligand/receptor cellular response assays, including those described in more detail below.

Another method involves screening for compounds which inhibit activation of the receptor polypeptide of the present invention by determining inhibition of binding of labeled ligand to cells which have the receptor on the surface thereof. Such a method would be especially useful for a TR1 receptor of the present invention which includes a transmembrane spanning amino acid sequence and involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia and Goeddel, *J. Biol. Chem.* 267:4304–4307(1992)).

Thus, in a further aspect, a screening method is provided for determining whether a candidate agonist or antagonist is capable of enhancing or inhibiting a cellular response to a TR1 receptor ligand. The method involves contacting cells which express the TR1 receptor polypeptide with a candidate compound and a ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TR1 receptor ligand (e.g., determining or estimating an increase or decrease in T-cell proliferation or tritiated thymidine labeling). By the invention, a cell expressing the TR1 receptor polypeptide can be contacted with either an endogenous or exogenously administered receptor ligand.

Agonists according to the present invention include naturally occurring and synthetic compounds such as, for example, TNF family ligand peptide fragments, transforming growth factor β, neurotransmitters (such as glutamate, dopamine, N-methyl-D-aspartate), tumor suppressors (p53), cytolytic T-cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and β-amyloid peptide (*Science* 267:1457–1458 (1995)). Further preferred agonists include polygonal and monoclonal antibodies raised against the TR1 receptor polypeptide, or a fragment thereof. Such agonist antibodies raised against a TNF-family receptors are disclosed in Tartaglia et al., *Proc. Natl. Acad. Sci. USA* 88:9292–9296 (1991); and Tartaglia and Goeddel, *J. Biol. Chem.* 267(7): 4304–4307(1992) See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus E1B, Baculovirus p35 and IAP, Cowpox virus crmA, Epstein-Barr virus BHRF1, LMP-1, African swine fever virus LMW5-HL, and Herpesvirus γ1 34.5), calpain inhibitors, cysteine protease inhibitors, and tumor promoters (such as PMA, Phenobarbital, and α-Hexachlorocyclohexane). Other antagonists include polyclonal and monoclonal antagonist antibodies raised against the TR1 receptor polypeptides or a fragment thereof. Such antagonist antibodies raised against a TNF-family receptor are described in Tartaglia and Goeddel, *J. Biol. Chem.* 267(7):4304–4307(1992)); and Tartaglia et al., *Cell* 73:213–216 (1993). See, also, PCT Application WO 94/09137.

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

In specific embodiments, antagonists according to the present invention are nucleic acids corresponding to the sequences contained in TR1, or the complementary strand thereof, and/or to nucleotide sequences contained in the deposited clone. In one embodiment, antisense sequence is generated internally by the organism, in another embodiment, the antisense sequence is separately administered (see, for example, O'Connor, J., *Neurochem.* 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, *J. Neurochem.* 56:560 (1991), "Oligodeoxynucleotides as Antisense Inhibitors of Gene Expression," CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the TR1 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR1 antisense nucleic acid. Such a vector can remain episomal or become chromosomally integrated, as long as it can be transcribed to produce the desired antisense RNA. Such vectors can be constructed by standard recombinant DNA technology methods. Vectors can be plasmid, viral, or others known in the art, which used for replication and expression in vertebrate cells. Expression of the sequence encoding TR1, or fragments thereof, can be by any promoter known to act in vertebrate, preferably human cells. Such promoters can be inducible or constitutive. Such promoters include, but are not limited to, the SV40 early promoter region (Bernoist and Chambon, *Nature* 29:304–310 (1981), the promoter contained in the 3' long terminal repeat of Rous sarcoma virus (Yamamoto et al., *Cell* 22:787–797 (1980), the herpes thymidine kinase promoter (Wagner et. al., *Proc. Natl. Acad. Sci. U.S.A.* 78:1 441–1445 (1981), the regulatory sequences of the metallothionein gene (Brinster, et al., *Nature* 296:39–42 (1982)), etc.

The antisense nucleic acids of the invention comprise a sequence complementary to at least a portion of an RNA transcript of a TR1 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR1 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a TR1 RNA it may contain and still form a stable duplex (or triplex as the case may be). One skilled in the art can ascertain a tolerable degree of mismatch by determining the melting point of the hybridized complex using standard procedures.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, *Nature* 372:333–335. Thus, oligonucleotides complementary to either the 5'- or 3'-untranslated regions of the TR1 shown in FIG. 1 (SEQ ID NO:2) or FIG. 2 (SEQ ID NO:4) could be used in an antisense approach to inhibit translation of endogenous TR1 mRNA. Oligonucleotides complementary to the 5' untranslated region of the mRNA should include the complement of the AUG start codon. Antisense oligonucleotides complementary to protein coding regions are less efficient inhibitors of translation but could be used in accordance with the invention. Whether designed to hybridize to the 5'-, 3'- or protein coding region of TR1 mRNA, antisense nucleic acids should be at least six nucleotides in length, and preferably range from 6 to about 50 nucleotides in length. In specific aspects the oligonucleotide is at least 10 nucleotides, at least 17 nucleotides, at least 25 nucleotides or at least 50 nucleotides long.

The polynucleotides of the invention can be DNA, RNA or chimeric mixtures, or derivatives or modified versions thereof, and can be single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo); agents facilitating transport across the cell membrane (see, e.g., Letsinger et al., 1989, *Proc. Natl. Acad. Sci. U.S.A.* 86:6553–6556; Lemaitre et al, 1987, *Proc. Natl. Acad. Sci.* 84:648–652; PCT Publication No. WO88/09810, published Dec. 15, 1988) or the blood-brain barrier (see, e.g., PCT Publication No. WO89/10134, published Apr. 25, 1988); hybridization-triggered cleavage agents (see, e.g., Krol et al., 1988, *BioTechniques* 6:958–976); or intercalating agents (see, e.g., Zon, 1988, *Pharm. Res.* 5:539–549). To this end, the oligonucleotide may be conjugated to another molecule, (e.g., a peptide, hybridization triggered cross-linking agent, transport agent, hybridization-triggered cleavage agent, etc.).

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641 (1987)). The oligonucleotide is a 2'-O-methylribonucleotide (Inoue et al., *Nucl. Acids Res.* 15:6131–6148 (1987)), or a chimeric RNA-DNA analogue (Inoue et al., *FEBS Lett.* 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)), etc.

While antisense nucleotides complementary to the TR1 coding region sequence could be used, those complementary to the transcribed untranslated region are most preferred.

Potential antagonists according to the invention also include catalytic RNA or a ribozyme (See, e.g., PCT International Publication WO 90/11364, published Oct. 4, 1990; Sarver et al., *Science* 247:1222–1225 (1990)). While ribozymes that cleave mRNA at site specific recognition sequences can be used to destroy TR1 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of TR1 (FIG. 1 and FIG. 2). Preferably, the ribozyme is engineered so that the cleavage recognition site is located near the 5' end of the TR1 mRNA; i.e., to increase efficiency and minimize the intracellular accumulation of non-functional mRNA transcripts.

As in the antisense approach, the ribozymes of the invention can be composed of modified oligonucleotides (e.g., for improved stability, targeting, etc.) and should be delivered to cells which express TR1 in vivo. DNA constructs encoding the ribozyme may be introduced into the cell in the same manner as described above for the introduction of antisense encoding DNA. A preferred method of delivery involves using a DNA construct encoding the ribozyme under the control of a strong constitutive promoter, (for example, pol III or pol II promoter), so that transfected cells will produce sufficient quantities of the ribozyme to destroy endogenous TR1 messages and inhibit translation. Since ribozymes, unlike antisense molecules, are catalytic, a lower intracellular concentration is required for efficiency.

Endogenous gene expression can also be reduced by inactivating or "knocking out" the TR1 gene and/or its promoter using targeted homologous recombination. (see, e.g., Smithies et al., *Nature* 317:230–234 (1985); Thomas & Capecchi, *Cell* 51:503–512(1987); Thompson et al., *Cell* 5:313–321 (1989), each of which is incorporated by reference herein in its entirety). For example, a mutant, non-functional polynucleotide of the invention (or a completely unrelated DNA sequence) flanked by DNA homologous to the endogenous TR1 polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agriculture where modifications to embryonic stem cells can be used to generate animal offspring with an inactive targeted gene (see, e.g., Thomas & Capecchi 1987 and Thompson 1989, supra). However this approach can be routinely adapted for use in humans provided the recombinant DNA constructs are targeted to the required site in vivo using appropriate viral vectors as will be apparent to those of skill in the art. The contents of each of the documents recited in this paragraph is herein incorporated by reference in its entirety.

In other embodiments, antagonists according to the present invention include soluble forms of TR1 (e.g., fragments of the TR1 shown in FIGS. 1 and 2 that include the ligand binding domain of TR1). Such soluble forms of TR1, which may be naturally occurring or synthetic, antagonize TR1 mediated signaling by competing with the cell surface forms of the TR1 receptor for binding to TNF-family ligands. Antagonists of the present invention also include antibodies specific for TNF-family ligands and TR1-Fc fusion proteins.

By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF).

Further antagonist according to the present invention include soluble TR1 receptor fragments, e.g., TR1 receptor fragments that include the ligand binding domain from the extracellular region of the full length receptor. Such soluble forms of the receptor, which may be naturally occurring or synthetic, antagonize TR1 receptor mediated signaling by competing with the cell surface forms of the TR1 receptor for binding to TNF-family ligands. Thus, such antagonists include soluble forms of the receptor that contain the ligand binding domains of the polypeptides of the present invention.

The invention further relates to antibodies which act as agonists or antagonists of the polypeptides of the present invention. For example, the present invention includes antibodies which disrupt receptor/ligand interactions of the polypeptides of the invention either partially or fully. Included are both receptor-specific antibodies and ligand-specific antibodies. Included are receptor-specific antibodies which do not prevent ligand binding but which prevent receptor activation. Receptor activation (i.e., signaling) may be determined by techniques described herein or otherwise known in the art. Also included are receptor-specific antibodies which prevent both ligand binding and receptor activation. Likewise included are neutralizing antibodies which bind the ligand and prevent ligand-receptor binding, as well as antibodies which bind the ligand and thereby prevent receptor activation, but which do not prevent ligand-receptor binding. Further included are antibodies which activate the receptor. These antibodies may act as agonists for either all or fewer than all of the biological activities affected by ligand-mediated receptor activation. The antibodies may be specified as agonists or antagonists for biological activities comprising specific activities disclosed herein. The above antibody agonists can be made using methods known in the art. See, e.g., WO 96/40281; U.S. Pat. No. 5,811,097; Deng, B. et al., *Blood* 92:1981–1988 (1998); Chen, Z. et al., *Cancer Res.* 58:3668–3678 (1998); Harrop, J. A. et al., *J. Immunol.* 161:1786–1794 (1998); Zhu, Z. et al., *Cancer Rev.* 58:3209–3214 (1998); Yoon, D. Y. et al., *J. Immunol* 160:3170–3179 (1998); Prat, M. et al., *J. Cell. Sci.* 111(Pt2):237–247 (1998); Pitard, V. et al., *J. Immunol Methods* 205:177–190(1997); Liautard, J. et al., *Cytokine* 9(4): 233–241 (1997); Carlson, N. G. et al., *J. Biol. Chem.* 272:11295–11301 (1997); Taryman, R. E. et al., *Neuron* 14:755–762 (1995); Muller, Y. A. et al., *Structure*

6:1153–1167 (1998); Bartunek, P. et al., *Cytokine* 8:14–20 (1996)(said references incorporated by reference in their entireties).

Antibodies according to the present invention may be prepared by any of a variety of standard methods using TR1 receptor immunogens of the present invention. Such TR1 receptor immunogens include the TR1 receptor protein shown in FIG. 1 (SEQ ID NO:2) and FIG. 2 (SEQ ID NO:4) (which may or may not include a leader sequence) and polypeptide fragments of the receptor comprising the ligand binding domain.

Polyclonal and monoclonal antibody agonists or antagonists according to the present invention can be raised according to the methods disclosed herein and and/or known in the art, such as, for example, those methods described in Tartaglia and Goeddel, *J. Biol. Chem.* 267:4304–4307(1992)); Tartaglia et al., *Cell* 73:213–216 (1993)), and PCT Application WO 94/09137 (the contents of each of these three applications are herein incorporated by reference in their entireties), and are preferably specific to polypeptides of the invention having the amino acid sequence of SEQ ID NOS: 2 and/or 4.

As indicated polyclonal and monoclonal antibody agonists or antagonists according to the present invention can be raised according to the methods disclosed in Tartaglia and Goeddel, *J. Biol. Chem.* 267:4304–4307(1992)); Tartaglia et al., *Cell* 73:213–216 (1993)), and PCT Application WO 94/09137. The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)).

Antibodies according to the present invention may be prepared by any of a variety of methods using TR1 receptor immunogens of the present invention. As indicated, such TR1 receptor immunogens include the full length TR1 receptor polypeptide (which may or may not include the leader sequence) and TR1 receptor polypeptide fragments such as the ligand binding domain, the extracellular domain and the intracellular domain.

In a preferred method, antibodies according to the present invention are mAbs. Such mAbs can be prepared using hybridoma technology (Kohler and Millstein, *Nature* 256: 495–497 (1975) and U.S. Pat. No. 4,376,110; Harlow et al., *Antibodies*: A Laboratory Manual, Cold Spring Harbor Laboratory Press, Cold Spring Harbor, N.Y., 1988; *Monoclonal Antibodies and hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Thymocytes, which have been shown to express the TR1 receptor of the present invention, can be used in a proliferation assay to identify both ligands and potential agonists and antagonists to the polypeptide of the present invention. For example, thymus cells are disaggregated from tissue and grown in culture medium. Incorporation of DNA precursors such as $^3$H-thymidine or 5-bromo-2'-deoxyuridine (BrdU) is monitored as a parameter for DNA synthesis and cellular proliferation. Cells which have incorporated BrdU into DNA can be detected using a monoclonal antibody against BrdU and measured by an enzyme or fluorochrome-conjugated second antibody. The reaction is quantitated by fluorimetry or by spectrophotometry. Two control wells and an experimental well are set up. TNF-β is added to all wells, while soluble receptors of the present invention are added to the experimental well. Also added to the experimental well is a compound to be screened. The ability of the compound to be screened to inhibit the interaction of TNF-β with the receptor polypeptides of the present invention may then be quantified. In the case of the agonists, the ability of the compound to enhance this interaction is quantified.

A determination may be made whether a ligand not known to be capable of binding to the polypeptide of the present invention can bind thereto comprising contacting a mammalian cell comprising an isolated molecule encoding a polypeptide of the present invention with a ligand under conditions permitting binding of ligands known to bind thereto, detecting the presence of any bound ligand, and thereby determining whether such ligands bind to a polypeptide of the present invention. Also, a soluble form of the receptor may utilized in the above assay where it is secreted in to the extra-cellular medium and contacted with ligands to determine which will bind to the soluble form of the receptor.

Other agonist and antagonist screening procedures involve providing appropriate cells which express the receptor on the surface thereof. In particular, a polynucleotide encoding a polypeptide of the present invention is employed to transfect cells to thereby express the polypeptide. Such transfection may be accomplished by procedures as hereinabove described.

Thus, for example, such assay may be employed for screening for a receptor antagonist by contacting the cells which encode the polypeptide of the present invention with both the receptor ligand and a compound to be screened. Inhibition of the signal generated by the ligand indicates that a compound is a potential antagonist for the receptor, i.e., inhibits activation of the receptor.

Proteins and other compounds which bind the TR1 receptor domains are also candidate agonist and antagonist according to the present invention. Such binding compounds can be "captured" using the yeast two-hybrid system (Fields and Song, *Nature* 340:245–246 (1989). A modified version of the yeast two-hybrid system has been described by Roger Brent and his colleagues (Gyuris, et al., *Cell* 75:791–803 (1993), Zervos, et al., *Cell* 72:223–232 (1993)). Briefly, a domain of the TR1 receptor polypeptide is used as bait for binding compounds. Positives are then selected by their ability to grow on plates lacking leucine, and then further tested for their ability to turn blue on plates with X-gal, as previously described in great detail (Gyuris, et al., supra). Preferably, the yeast two-hybrid system is used according to the present invention to capture compounds which bind to either the TR1 receptor ligand binding domain or to the TR1 receptor intracellular domain. Such compounds are good candidate agonist and antagonist of the present invention. This system has been used previously to isolate proteins which bind to the intracellular domain of the p55 and p75 TNF receptors (WO 95/31544). Once amino acid sequences are identified which bind to the TR1 receptor, these sequences can be screened for agonist or antagonist activity using, for example, the thymocyte proliferation assay described above.

Another assay which can be performed to identify agonists and antagonists of the TR1 receptors of the present invention involves the use of combinatorial chemistry to produce random peptides which then can be screened for both binding affinity the TR1 receptors and agonistic or antagonistic effects. One such assay has recently been performed using random peptides expressed on the surface of a bacteriophage. Wu, *Nature Biotechnology* 14:429–431. In this instance, a phage display library was produced which displayed a vast array of peptides on the surface of the phage. The phage of this library were then injected into mice and phage expressing peptides which bound to various organs were then identified. The DNA contained in the phage bound to the organs was then sequenced to identify peptide motifs which are capable of interacting with the surfaces of cells in each organ. One skilled in the art would recognize that such a random peptide library could also be screened for motifs which bind to the surface of the TR1 receptors of the present invention. After such motifs are identified, these peptides can then be screened for agonistic or antagonistic activity using the assays described herein.

Other screening techniques include the use of cells which express the polypeptide of the present invention (for example, transfected CHO cells) in a system which measures extracellular pH changes caused by receptor activation, for example, as described in *Science*, 246:181–296 (1989). In another example, potential agonists or antagonists may be contacted with a cell which expresses the polypeptide of the present invention and a second messenger response, e.g., signal transduction may be measured to determine whether the potential antagonist or agonist is effective.

TR1 receptor antagonists also include a small molecule which binds to and occupies the TR1 receptor thereby making the receptor inaccessible to ligands which bind thereto such that normal biological activity is prevented. Examples of small molecules include but are not limited to small peptides or peptide-like molecules.

The TR1 receptor agonists may be employed to stimulate ligand activities, such as inhibition of tumor growth and necrosis of certain transplantable tumors. The agonists may also be employed to stimulate cellular differentiation, for example, T-cell, fibroblasts and haemopoietic cell differentiation. Agonists to the TR1 receptor may also augment TR1's role in the host's defense against microorganisms and prevent related diseases (infections such as that from *L. monocytogenes*) and Chlamidiae. The agonists may also be employed to protect against the deleterious effects of ionizing radiation produced during a course of radiotherapy, such as denaturation of enzymes, lipid peroxidation, and DNA damage.

The agonists may also be employed to mediate an antiviral response, to regulate growth, to mediate the immune response and to treat immunodeficiencies related to diseases such as HIV.

Antagonists to the TR1 receptor may be employed to treat autoimmune diseases, for example, graft versus host rejection and allograft rejection, and T-cell mediated autoimmune diseases. It has been shown that T-cell proliferation is stimulated via a type 2 TNF receptor. Accordingly, antagonizing the receptor may prevent the proliferation of T-cells and treat T-cell mediated autoimmune diseases.

The antagonists may also be employed to prevent apoptosis, which is the basis for diseases such as viral infection, rheumatoid arthritis, systemic lupus erythematosus, insulin-dependent diabetes mellitus, and graft rejection. Similarly, the antagonists may be employed to prevent cytotoxicity.

The antagonists to the TR1 receptor may also be employed to treat B cell cancers which are stimulated by TR1.

Antagonists to the TR1 receptor may also be employed to treat and/or prevent septic shock, which remains a critical clinical condition. Septic shock results from an exaggerated host response, mediated by protein factors such as TNF and IL-1, rather than from a pathogen directly. For example, lipopolysaccharides have been shown to elicit the release of TNF leading to a strong and transient increase of its serum concentration. TNF causes shock and tissue injury when administered in excessive amounts. Accordingly, it is believed that antagonists to the TR1 receptor will block the actions of TNF and treat/prevent septic shock. These antagonists may also be employed to treat meningococcemia in children which correlates with high serum levels of TNF.

Among other disorders which may be treated by the antagonists to TR1 receptors, there are included, inflammation which is mediated by TNF receptor ligands, and the bacterial infections cachexia and cerebral malaria. The TR1 receptor antagonists may also be employed to treat inflammation mediated by ligands to the receptor such as TNF. In addition, TR1 receptors may also be useful for providing treatment for AIDS in that TNF-β is involved in the development of lymphocytes.

Therapeutics: Modes of Administration

The soluble TR1 receptor and agonists and antagonists may be employed in combination with a suitable pharmaceutical carrier. Such compositions comprise a therapeutically effective amount of the soluble receptor or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the soluble form of the receptor and agonists and antagonists of the present invention may also be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/kg body weight per day. In most cases, the dosage is from about 10 µg/kg to about 1 mg/kg body weight daily, taking into account the routes of administration, symptoms, etc.

The TR1 receptor polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman. et al., *Biopolymers* 22:547–556 (1983)), poly (2-hydroxyethyl methacrylate) (Langer et al., *J. Biomed. Mater. Res.* 15:167–277 (1981), and Langer, *Chem. Tech.* 12:98–105 (1982)), ethylene vinyl acetate (Langer et al., *Id.*) or poly-D-(-)-3-hydroxybutyric acid (EP 133,988). Sustained-release TR1 receptor polypeptide compositions also include liposomally entrapped TR1 receptor polypeptide. Liposomes containing TR1 receptor polypeptide are prepared by methods known per se: DE 3,218,121; Epstein et al., *Proc. Natl Acad. Sci.* (*USA*) 82:3688–3692 (1985); Hwang et al., *Proc. Natl Acad. Sci.* (*USA*) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal TR1 receptor polypeptide therapy.

For parenteral administration, in one embodiment, the TR1 receptor polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the TR1 receptor polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The TR1 receptor polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of TR1 receptor polypeptide salts.

TR1 receptor polypeptide to be used for therapeutic administration must be sterile. Sterility is readily accomplished by filtration through sterile filtration membranes (e.g., 0.2 micron membranes). Therapeutic TR1 receptor polypeptide compositions generally are placed into a container having a sterile access port, for example, an intravenous solution bag or vial having a stopper pierceable by a hypodermic injection needle.

TR1 receptor polypeptide ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous TR1 receptor polypeptide solution, and the resulting mixture is lyophilized. The infusion solution is prepared by reconstituting the lyophilized TR1 receptor polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The TR1 receptor and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques,* 7:980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+en-vAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include nucleic acid sequences encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The polypeptides of the invention can also be expressed in transgenic animals. Animals of any species, including but not limited to, mice, rats, rabbits, hamsters, guinea pigs, pigs, micro-pigs, goats, sheep, cows and non-human primates (e.g., baboons, monkeys and chimpanzees) may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol Biotechnol.* 40:691–698 (1994); Carver et al., *Biotechnology* (NY) 11:1263–1270 (1993); Wright et al., *Biotechnology* (NY) 9:830–834 (1991); and Hoppe et al, U.S. Pat. No. 4,873,191 (1989)); retrovirus mediated gene transfer into germ lines (Van der Putten et al., *Proc. Natl. Acad. Sci. USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, transfer into enucleated oocytes of nuclei from cultured embryonic, fetal, or adult cells induced to quiescence (Campell et al., *Nature* 380:64–66 (1996)); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies, such as concatamers, e.g., head-to-head tandems or head-to-tail tandems. The transgene may also be selectively introduced into and activated in a particular cell type using, for example, the teaching of Lasko et al (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed to integrate into and disrupt, via homologous recombination with chromosomal sequences, the function of the endogenous gene. The transgene may also be introduced selectively into a particular cell type, thus inactivating the endogenous gene in only that cell type, using, for example, the teaching of Gu et al. (Gu et al., *Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening of animal tissues may be accomplished by Southern blot analysis or PCR techniques to verify that integration of the transgene has taken place. The level of mRNA expression of the transgene in the tissues of the transgenic animals may also be assessed using techniques which include, but are not limited to, Northern blot analysis of tissue samples, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals having more than one integration site in order to establish separate lines; inbreeding of separate lines to produce compound transgenics that express the transgene at higher levels because of the additive effect of expression of multiple transgenes; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for a particular experimental model.

Transgenic and "knock-out" animals of the invention have uses as model systems for, including but not limited to, elaborating the biological function of TR1 polypeptides, studying conditions and/or disorders associated with aberrant TR1 expression, and screening for compounds effective in ameliorating such conditions and/or disorders.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive promoter or inducible promoter or a promoter/enhancer to achieve expression, and preferably secretion, of the polypeptides of the invention. The engineered cells which express and preferably secrete the polypeptides of the invention can be introduced into the patient systemically (e.g., in the circulation), or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well-known techniques which prevent the development of a host immune response against the introduced cells. For example, the cells may be introduced in an encapsulated form, which allows for an exchange of components with the immediate extracellular environment, but does not allow the introduced cells to be recognized by the host immune system.

Therapeutics: Combinatorial Formulations

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an agent that regulates bone and/or tissue growth. Bone growth and/or tissue growth regulators that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

Certain BMPs which are known to be osteogenic can also induce neuronal cell differentiation. Embryonic mouse cells treated with BMP-2 or OP-1 (BMP-7) differentiate into astrocyte-like (glial) cells, and peripheral nerve regeneration using BMP-2 has been recently reported (Wang et al., WO 95/05846). In addition, BMP-4, BMP-5 and OP-1 (BMP-7) are expressed in epidermal edtoderm flanking the neural plate. Ectopic recombinant BMP-4 and OP-1 (BMP-7) proteins are capable of inducing neural plate cells to initiate dorsal neural cell fate differentiation (Liem et al., *Cell* 82: 969–979 (1995)). At the spinal cord level, OP-1 and other BMPs, which should include the BMPs of the present invention, can induce neural crest cell differentiation. It is suggested that OP-1 and these BMPs can induce many or all dorsal neural cell types, including roof plate cells, neural crest cells, and commissural neurons, depending on localized positional cues. Therefore, additionally, morphogenic devices of this invention may also be implanted in or surrounding a joint for use in cartilage and soft tissue repair, or in or surrounding nervous system-associated tissue for use in neural regeneration and repair.

The tissue specificity of the particular morphogenic protein—or combination of morphogenic proteins with other biological factors—will determine the cell types or tissues that will be amenable to such treatments and can be selected by one skilled in the art. The ability to enhance other morphogenic protein-induced tissue regeneration by co-administering a BMP according to the present invention is thus not believed to be limited to any particular cell-type or tissue. It is envisioned that the invention as disclosed herein can be practiced to enhance the activities of new morphogenic proteins and to enhance new tissue inductive functions as they are discovered in the future.

The BMP compositions and devices comprising BMP will permit the physician to obtain predictable bone and/or cartilage formation. The BMP compositions and devices of this invention may be used to treat more efficiently and/or effectively all of the injuries, anomalies and disorders that have been described in the prior art of osteogenic devices. These include, for example, forming local bone in fractures, non-union fractures, fusions and bony voids such as those created in tumor resections or those resulting from cysts; treating acquired and congenital craniofacial and other skeletal or dental anomalies (see e.g., Glowacki et al., Lancet 1:959–963 (1981)); performing dental and periodontal reconstructions where lost bone replacement or bone augmentation is required such as in a jaw bone; and supplementing alveolar bone loss resulting from periodontal disease to delay or prevent tooth loss (see e.g., Sigurdsson et al., J. Periodontol., 66:511–521 (1995)).

An osteogenic device of this invention which comprises a matrix comprising allogenic bone and a BMP may also be implanted at a site in need of bone replacement to accelerate allograft repair and incorporation in a mammal. Another potential clinical application of the improved osteogenic devices of this invention is in cartilage repair, for example, following joint injury or in the treatment of osteoarthritis. The ability to enhance the cartilage-inducing activity of other morphogenic proteins by co-administering a BMP may permit faster or more extensive tissue repair and replacement using the same or lower levels of morphogenic proteins.

The BMP compositions and devices of this invention will be useful in treating certain congenital diseases and developmental abnormalities of cartilage, bone and other tissues. For example, homozygous OP-1 (BMP-7)-deficient mice die within 24 hours after birth due to kidney failure (Luo et al., J. Bone Min. Res. 10 (Supp. 1):S163 (1995)). Kidney failure in these mice is associated with the failure to form renal glomeruli due to lack of mesenchymal tissue condensation. OP-1-deficient mice also have various skeletal abnormalities associated with their hindlimbs, rib cage and skull, are polydactyl, and exhibit aberrant retinal development. These results, in combination with those discussed above concerning the ability of OP-1 to induce differentiation into dorsal neural cell fates, indicate that OP-1 plays an important role in epithelialmesenchymal interactions during development. It is anticipated that the compositions, devices and methods of this invention may be useful in the future for ameliorating these and other developmental abnormalities.

Developmental abnormalities of the bone may affect isolated or multiple regions of the skeleton or of a particular supportive or connective tissue type. These abnormalities often require complicated bone transplantation procedures and orthopedic devices. The tissue repair and regeneration required after such procedures may occur more quickly and completely with the use of the BMPs of the present invention or the use of other morphogenic proteins used in combination with the BMPs of the present invention.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor α-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: A Manual of Basic Techniques, Pergamon Press, New York (1988).

For example, the present inventors have mapped the native TR1 gene at the chromosomal region 8q23–24.1.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments. Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in the method of Graham and Van der, *Virology*, 52:456–457 (1973).

EXAMPLE 1

Bacterial Expression and Purification of TR1 Receptor

The DNA sequence encoding TR1 receptor, ATCC Accession No. 75899, is initially amplified using PCR oligonucleotide primers corresponding to the 5' and 3' end sequences of the processed TR1 receptor nucleic acid sequence (minus the signal peptide sequence). Additional nucleotides corresponding to TR1 receptor gene are added to the 5' and 3' end sequences respectively. The 5' oligonucleotide primer has the sequence 5' GCCAGAGGATCCGAAACGTTTCCTC-CAAAGTAC 3' (SEQ ID NO:6) and contains a BamHI restriction enzyme site (bold). The 3' sequence 5' CGGCT-TCTAGAATTACCTATCATTTCTAAAAAT 3' (SEQ ID NO:7) contains complementary sequences to a Hind III site (bold) and is followed by 18 nucleotides of TR1 receptor (FIG. 2). The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform *E. coli* strain M15/rep 4 (Qiagen, Inc.) by the procedure described in Sambrook et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 µg/ml) and Kan (25 µg/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 molar Guanidine HCl. After clarification, solubilized TR1 receptor is purified from this solution by chromatography on a Nickel-Chelate column under conditions that allow for tight binding by proteins containing the 6-His tag (Hochuli et al., *J. Chromatography* 411:177–184 (1984)). TR1 receptor (90% pure) is eluted from the column in 6 molar guanidine HCl pH 5.0 and for the purpose of renaturation adjusted to 3 molar guanidine HCl, 100 mM sodium phosphate, 10 mM glutathione (reduced) and 2 mM glutathione (oxidized). After incubation in this solution for 12 hours the protein is dialyzed to 10 mmolar sodium phosphate.

In addition to the above expression vector, the present invention further includes an expression vector, pHE4a (ATCC Accession Number 209645, deposited Feb. 25, 1998.), comprising phage operator and promoter elements. This vector contains: 1) a neomycin phosphotransferase gene as a selectable marker, 2) an *E. coli* origin of replication, 3) a T5 phage promoter sequence, 4) two lac operator sequences, 5) a Shine-Delgarno sequence, and 6) the lactose operon repressor gene (lacI$^q$). The origin of replication (oriC) is derived from pUC19 (LT1, Gaithersburg, Md.). The promoter sequence and operator sequences are made synthetically.

Useful restriction sites in pHE4a include NdeI and KpnI, BamHI, XhoI, or Asp718. The DNA insert is generated according to the PCR protocol described in Example 1, using PCR primers having restriction sites for NdeI (5' primer) and XbaI, BamHI, XhoI, or Asp718 (3' primer).

EXAMPLE 2

Cloning and Expression of the Native and the Carboxy Terminal Modified TR1 Receptor Using the Baculovirus Expression System The DNA sequence encoding the full-length native TR1 receptor protein, ATCC Accession No. 75899, is amplified using PCR oligonucleotide primers corresponding to the 5' and 3' sequences of the gene. The 5' primer has the sequence 5' CGC GGA TCC GCCATC ATGAACAAGTTGCTGTG 3' (SEQ ID NO: 8) and contains a BamHI restriction site followed by the first 17 base pairs of the native TR1 receptor coding sequence in FIG. 1.

The 3' primer has the sequence 5' CGC GGT ACC CAATTGTGAGGAAACAG3' (SEQ ID NO:9) and contains a Asp718 restriction site and, in reverse orientation, a sequence complementary to nucleotides 1270 to 1286 in FIG. 1.

For the carboxy terminal modified TR1 receptor, the 5' primer has the sequence 5' GCGCGGATCC ATGAACAAGTTGCTGTGCTGC 3' (SEQ ID NO: 10) and contains a BamHI restriction enzyme site (in bold) and which is just behind the first 21 nucleotides of the modified TR1 receptor gene (the initiation codon for translation "ATG" is underlined) shown in FIG. 2.

The 3' primer has the sequence 5' GCGCTCTAGATTAC-CTATCATTTCTAAAAATAAC 3' (SEQ ID NO:11) and contains the cleavage site for the restriction endonuclease XbaI and 21 nucleotides complementary to the 3' sequence of the modified TR1 receptor gene shown in FIG. 2.

The amplified modified TR1 receptor sequences were isolated from a 1% agarose gel using a commercially available kit ("Geneclean", BIO 101 Inc., La Jolla, Calif.). The fragments were then digested with the endonucleases BamHI and XbaI and then purified again on a 1% agarose gel. This fragment is designated F2.

The vector pRG1 (modification of pVL941 vector, discussed below) was used for the expression of the TR1 receptor proteins using the baculovirus expression system (for review see: Summers and Smith, A Manual of Methods for Baculovirus Vectors and Insect Cell Culture Procedures, Texas Agricultural Experimental Station Bulletin No. 1555 (1987)). This expression vector contains the strong polyhedrin promoter of the *Autographa californica* nuclear polyhedrosis virus (AcMNPV) followed by the recognition sites for the restriction endonucleases BamHI and XbaI. The polyadenylation site of the simian virus (SV40) was used for efficient polyadenylation. For an easy selection of recombinant viruses the beta-galactosidase gene from *E. coli* was inserted in the same orientation as the polyhedrin promoter followed by the polyadenylation signal of the polyhedrin gene. The polyhedrin sequences were flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow and Summers, *Virology* 170:31–39).

The plasmid was digested with the restriction enzymes BamHI and XbaI. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E. coli* HB101 cells were then transformed and cells identified that contained the plasmid (pBac TR1 receptor) with the TR1 receptor genes using the enzymes BamHI and XbaI. The sequence of the cloned fragment was confirmed by DNA sequencing.

5 μg of the plasmid pBac TR1 receptor was cotransfected with 1.0 μg of a commercially available linearized baculovirus ("BaculoGold™ baculovirus DNA", Pharmingen, San Diego, Calif.) using the lipofection method (Felgner et al., *Proc. Natl. Acad. Sci. USA,* 84:7413–7417 (1987)).

One μg of BaculoGold™ virus DNA and 5 μg of the plasmid pBac TR1 receptors were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg, Md.) was used which allows an easy isolation of blue stained plaques. (A detailed description of a "plaque assay" can also be found in the user's guide for insect cell culture and baculovirology distributed by Life Technologies Inc., Gaithersburg, Md., page 9–10).

Four days after the serial dilution, the viruses were added to the cells and blue stained plaques were picked with the tip of an Eppendorf pipette. The agar containing the recombinant viruses were then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-TR1 receptor at a multiplicity of infection (MOI) of 2. Six hours later the medium was removed and replaced with SF900 II medium minus methionine and cysteine (Life Technologies Inc., Gaithersburg). Forty-two hours later 5 μCi of $^{35}$S-methionine and 5 μCi $^{35}$S cysteine (Amersham) were added. The cells are further incubated for 16 hours before they are harvested by centrifugation and the labelled proteins visualized by SDS-PAGE and autoradiography.

EXAMPLE 3

Cloning and Expression in Mammalian Cells

Most of the vectors used for the transient expression of the TR1 receptor protein gene sequences in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of trancription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkart cells, mouse NIH3T3 and C127 cells, Cos 1, Cos 7 and CV1, African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J.* 22 7:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology,* 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 3(a)

Expression of Recombinant Native TR1 Receptor in COS Cells

The expression of plasmid, TR1 receptor HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire TR1 receptor precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (Wilson et al., Cell 37:767 (1984)). The infusion of HA tag to the target protein allows easy detection of the recombinant protein with an antibody that recognizes the HA epitope.

For the native TR1 receptor (FIG. 1), the plasmid construction strategy is described as follows:

The DNA sequence encoding native TR1 receptor, ATCC Accesion No. 75899, is constructed by PCR using two primers: The 5' primer has the sequence 5'CGCGGATCCGCCATC ATGAACAAGTTGCTGTG 3' (SEQ ID NO:8) and contains a BamHI restriction site followed by the first 17 base pairs of the native TR1 receptor coding sequence in FIG. 1.

The 3' primer has the sequence 5' CGCGGTACCCAAT-TGTGAGGAAACAG 3' (SEQ ID NO:9) and contains a Asp718 restriction site and, in reverse orientation, a sequence complementary to nucleotides 1270 to 1286 in FIG. 1.

Therefore, the PCR product contains a BamHI site, a TR1 receptor coding sequence followed by HA tag fused in frame, a translation termination stop codon next to the HA tag, and an Asp718 site. The PCR amplified DNA fragment and the vector, pcDNAI/Amp, are digested with BamHI and Asp718 restriction enzymes and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant TR1 receptors, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the TR1 receptor HA protein is detected by radiolabelling and immunoprecipitation method (Harlow and Lane, Antibodies: A Laboratory Manual, Cold Spring Harbor Laboratory Press, (1988)). Cells are labeled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5) (Wilson et al., supra). Both cell lysate and culture media are precipitated with a HA specific monoclonal antibody. Proteins precipitated are analyzed on 15% SDS-PAGE gels.

EXAMPLE 3(b)

Cloning and Expression of the Native Receptor in CHO Cells

The vector pC1 is used for the expression of native TR1 receptor protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A., *Biotechnology* 9:64–68 (1991)). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., *Molecular and Cellular Biology*, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding the native TR1 receptor, ATCC 75899, is amplified using PCR oligonucleotide primers corresponding to the 5' and 3' sequences of the gene:

The 5' primer has the sequence 5' CGCGGATCCGC-CATC ATGAACAAGTTGCTGTG 3' (SEQ ID NO:8) and contains a BamHI restriction site followed by the first 17 base pairs of the native TR1 receptor coding sequence in FIG. 1.

The 3' primer has the sequence 5' CGCGGTACC CAAT-TGTGAGGAAACAG 3' (SEQ ID NO: 9) and contains a Asp718 restriction site and, in reverse orientation, a sequence complementary to nucleotides 1270 to 1286 in FIG. 1.

Inserted into an expression vector, as described below, the 5' end of the amplified fragment encoding human TR1 receptor provides an efficient signal peptide. An efficient signal for initiation of translation in eukaryotic cells, as described by Kozak, *Mol. Biol.* 196:947–950 (1987) is appropriately located in the vector portion of the construct.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-cells

Chinese hamster ovary cells lacking an active DHFR enzyme are used for transfection. 5 µg of the expression plasmid C1 are cotransfected with 0.5 µg of the plasmid pSV-neo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 µM, 2 µM, 5 µM). The same procedure is repeated until clones grow at a concentration of 100 µM.

The expression of the desired gene product is analyzed by Western blot analysis and SDS-PAGE.

EXAMPLE 4

Purification of Soluble Native TR1 Receptor

Analysis of the amino acid sequence of native TR1 receptor shows a relatively high theoretical pI. A chromatography procedure was developed based on this feature to capture this protein to cation exchange column (poros 50 HS) at pH 7.0 at which most of other proteins do not bind to the column. This single-step purification yields 80–90% pure protein from recombinant baculovirus infected Sf-9 cell supernatant. The purified protein was confirmed to be the TNF-receptor homolog by N-terminus amino acid sequence analysis. The TR1-receptor can be further purified to >95% purity through heparin binding chromatography.

Seventeen mg of purified soluble TR1-receptor was prepared from 2 liters of baculovirus supernatant. Two mg of protein was used for antibody production. See, FIGS. 5–8.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier et al., *DNA*, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform *E. coli* strain HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product. Numerous modifications and variations of the present invention are possible in light of the above teachings and, therefore, within the scope of the appended claims, the invention may be practiced otherwise than as particularly described.

EXAMPLE 6

Osteogenic Cell Proliferation Assay for TR1 Receptor Activity

An assay for proliferatory effect of candidate agonists and antagonists of TR1 receptor function was performed using osteobast cell line HG63 as follows: A two-fold serial dilution of purified native TR1 receptor protein starting from 1000 ng/ml was made in RPMI 1640 medium with 0.5 to 10% FBS. Adherent target cells were prepared from confluent cultures by trypsinization in PBS, and non-adherent target cells were harvested from stationary cultures and washed once with fresh medium. Target cells were suspended at $1 \times 10^5$ cells/ml in medium containing 0.5% FBS and 0.1 ml aliquots were dispensed into 96-well flat-bottomed microtiter plates containing 0.1 ml serially diluted test samples. Incubation was continued for 70 hr. The activity was quantified using an MTS [3(4,5-dimethyl-thiazoyl-2-yl) 5 (3-carboxymethoxyphenyl)-2-(4-sulfophenyl)-2H-tetrazolium)] Assay or any other assay for cell numbers and/or activity. The MTS assay was performed by the addition of 20 µl of MTS and phenazine methosulfate (PMS) solution to 96 well plates (Stock solution was prepared as described by Promega Technical Bulletin No. 169). During a 3 hour incubation, living cells convert the MTS into a the aqueous soluble formazan product. Wells with medium only (no cells) were processed in exactly the same manner as the rest of the wells and were used for blank controls. Wells with medium and cells were used as baseline controls. The absorbence at 490 nm was recorded using an ELISA reader and is proportional to the number of viable cells in the wells. Cell growth promotion (positive percentage) or inhibition (negative percentage), as a percentage compared to baseline control wells (variation between three baseline control well is less than 5%), calculated for each sample concentration, by the formula: O.D. experimental/O.D. baseline control X 100—100. All determinations were made in triplicate. Mean and SD were calculated by Microsoft Excel.

EXAMPLE 7

Northern Blot Analysis

Northern blot analysis is carried out to examine TR1 receptor gene expression in human tissues. A cDNA probe containing the sequence shown in FIG. 1 was labeled with $^{32}P$ using the rediprime DNA labelling system from Amersham Life Science, according to manufacturer's instructions. Unincorporated nucleotide was removed from labled probe using CHROMA SPIN-100 (Clontech). Two human Multiple Tissue Northern (MTN) blots (one labaled as H for human tissue, the other labaled as $H_2$ for human immune system) containing approximately 2 mg of poly (A)+ RNA per lane from various human tissues were purchased from Clontech. Also used were two Cellline blots containing 20 ng total RNA from different cell lines. Northern blotting was performed with the Expresshyb Hybridization Solution (PT 1190-1) from Clontech according to the manufacture's manual.

Gene expression was detected in heart, placenta, lung, liver, and kidney tissue. Lower levels of the mRNA was detected in thymus, prostate, testis, ovary, and small intestine. Expression was also detected in osteoblastoma, smooth muscle, fibroblasts, ovarian cancer, venous endothelial cells, monocyte lukemia cells, liver cells, and lung emphysemia cells. Expression can also be detected in the following cell types: human hippocampus, kidney medulla, macrophage, osteoblasts, human pancreas tumor, fetal cochlea, and adult pulmonary.

EXAMPLE 8

Isolation of Antibody Fragments Directed Against Polypeptides of the Present Invention From a Library of scFvs Naturally occuring V-genes isolated from human PBLs are constructed into a large library of antibody fragments which contain reactivities against polypeptides of the present invention to which the donor may or may not have been exposed (see, e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ E. coli harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2 \times 10^8$ TU of delta gene 3 helper phage (M13 delta gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 ug/ml ampicillin and 50 ug/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately 1013 transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. Coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO92/01047) and then by sequencing.

EXAMPLE 9

Method of Determining Alterations in the TR1 Receptor Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO: 1. Suggested PCR conditions consist of 35 cycles at 95° C. for 30 seconds; 60–120 seconds at 52–58° C.; and 60–120 seconds at 70° C., using buffer solutions described in Sidransky, D., et al., *Science* 252:706 (1991).

PCR products are then sequenced using primers labeled at their 5' end with T4 polynucleotide kinase, employing SequiTherm Polymerase. (Epicentre Technologies). The intron-exon borders of selected exons of TR1 receptor are also determined and genomic PCR products analyzed to confirm the results. PCR products harboring suspected mutations in TR1 receptor are then cloned and sequenced to validate the results of the direct sequencing.

PCR products of the TR1 receptor are cloned into T-tailed vectors as described in Holton, T. A. and Graham, M. W., *Nucleic Acids Research,* 19:1156 (1991) and sequenced with T7 polymerase (United States Biochemical). Affected individuals are identified by mutations in TR1 receptor not present in unaffected individuals.

Genomic rearrangements are also observed as a method of determining alterations in the TR1 receptor gene. Genomic clones isolated using techniques known in the art are nick-translated with digoxigenindeoxy-uridine 5'-triphosphate (Boehringer Manheim), and FISH performed as described in Johnson, Cg. et al., *Methods Cell Biol.* 35:73–99 (1991). Hybridization with the labeled probe is carried out using a vast excess of human cot-1 DNA for specific hybridization to the TR1 receptor genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., *Genet. Anal. Tech. Appl.,* 8:75 (1991).) Image collection, analysis and chromosomal fractional length measurements are performed using the ISee Graphical Program System. (Inovision Corporation, Durham, N.C.) Chromosome alterations of the genomic region of TR1 receptor (hybridized by the probe) are identified as insertions, deletions, and translocations. These TR1 receptor alterations are used as a diagnostic marker for an associated disease.

EXAMPLE 10

Method of Detecting Abnormal Levels of TR1 receptor in a Biological Sample

TR1 receptor polypeptides can be detected in a biological sample, and if an increased or decreased level of TR1 receptor is detected, this polypeptide is a marker for a particular phenotype. Methods of detection are numerous, and thus, it is understood that one skilled in the art can modify the following assay to fit their particular needs.

For example, antibody-sandwich ELISAs are used to detect TR1 receptor in a sample, preferably a biological sample. Wells of a microtiter plate are coated with specific antibodies to TR1 receptor, at a final concentration of 0.2 to 10 µg/ml. The antibodies are either monoclonal or polyclonal and are produced using technique known in the art. The wells are blocked so that non-specific binding of TR1 receptor to the well is reduced.

The coated wells are then incubated for >2 hours at room temperature with a sample containing TR1 receptor. Preferably, serial dilutions of the sample should be used to validate results. The plates are then washed three times with deionized or distilled water to remove unbounded TR1 receptor.

Next, 50 µl of specific antibody-alkaline phosphatase conjugate, at a concentration of 25–400 ng, is added and incubated for 2 hours at room temperature. The plates are again washed three times with deionized or distilled water to remove unbounded conjugate.

75 µl of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is prepared using the experimental results from serial dilutions of a control sample with the sample concentration plotted on the X-axis (log scale) and fluorescence or absorbance on the Y-axis (linear scale). The TR1 receptor polypeptide concentration in a sample is then interpolated using the standard curve based on the measured flourescence of that sample.

EXAMPLE 11

Method of Treating Decreased Levels of TR1 Receptor

The present invention relates to a method for treating an individual in need of a decreased level of TR1 receptor biological activity in the body comprising, administering to such an individual a composition comprising a therapeutically effective amount of TR1 receptor antagonist. Preferred antagonists for use in the present invention are TR1 receptor-specific antibodies.

Moreover, it will be appreciated that conditions caused by a decrease in the standard or normal expression level of the TR1 receptor in an individual can be treated by administering TR1 receptor, preferably in a soluble and/or secreted form. Thus, the invention also provides a method of treatment of an individual in need of an increased level of TR1 receptor polypeptide comprising administering to such an individual a pharmaceutical composition comprising an amount of TR1 receptor to increase the biological activity level of TR1 receptor in such an individual.

For example, a patient with decreased levels of TR1 receptor polypeptide receives a daily dose 0.1–100 µg/kg of the polypeptide for six consecutive days. Preferably, the polypeptide is in a soluble and/or secreted form.

EXAMPLE 12

Method of Treating Increased Levels of TR1 Receptor

The present invention also relates to a method for treating an individual in need of an increased level of TR1 receptor biological activity in the body comprising administering to such an individual a composition comprising a therapeutically effective amount of TR1 receptor or an agonist thereof.

Antisense technology is used to inhibit production of TR1 receptor. This technology is one example of a method of decreasing levels of TR1 receptor polypeptide, preferably a soluble and/or secreted form, due to a variety of etiologies, such as cancer.

For example, a patient diagnosed with abnormally increased levels of TR1 receptor is administered intravenously antisense polynucleotides at 0.5, 1.0, 1.5, 2.0 and 3.0 mg/kg day for 21 days. This treatment is repeated after a 7-day rest period if the is determined to be well tolerated.

EXAMPLE 13

Method of Treatment Using Gene Therapy—Ex Vivo

One method of gene therapy transplants fibroblasts, which are capable of expressing soluble and/or mature TR1 receptor polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA*, 7:219–225 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding the TR1 receptor can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform *E. coli* HB101, which are then plated onto agar containing kanamycin for the purpose of confirming that the vector contains properly inserted TR1 receptor.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TR1 receptor gene is then added to the media and the packaging cells transduced with the vector. The packaging cells now produce infectious viral particles containing the TR1 receptor gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TR1 receptor protein is produced.

The engineered fibroblasts are then transplanted onto the host, either alone or after having been grown to confluence on cytodex 3 microcarrier beads.

EXAMPLE 14

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TR1 receptor sequences into an animal to increase or decrease the expression of the TR1 receptor polypeptide. The TR1 receptor polynucleotide may be operatively linked to a promoter or any other genetic elements necessary for the expression of the TR1 receptor polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35:470–479 (1997); Chao J. et al., *Pharmacol Res.* 35:517–522 (1997); Wolff J. A. *Neuromuscul. Disord.* 7:314–318 (1997); Schwartz B. et al., *Gene Ther.* 3:405–411 (1996); Tsurumi Y. et al., *Circulation* 94:3281–3290 (1996) (incorporated herein by reference).

The TR1 receptor polynucleotide constructs may be delivered by any method that delivers injectable materials to the cells of an animal, such as, injection into the interstitial space of tissues (heart, muscle, skin, lung, liver, intestine and the like). The TR1 receptor polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TR1 receptor polynucleotides may also be delivered in liposome formulations (such as those taught in Felgner P. L. et al. *Ann. NY Acad. Sci.* 772:126–139 (1995), and Abdallah B. et al. *Biol. Cell* 85:1–7 (1995)) which can be prepared by methods well known to those skilled in the art.

The TR1 receptor polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TR1 receptor polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TR1 receptor polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TR1 receptor polynucleotide constructs can be delivered to arteries during angioplasty by the catheter used in the procedure.

The dose response effects of injected TR1 receptor polynucleotide in muscle in vivo are determined as follows. Suitable TR1 receptor template DNA for production of mRNA coding for TR1 receptor polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TR1 receptor template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 μm cross-section of the individual quadriceps muscles is histochemically stained for TR1 receptor protein expression. A time course for TR1 receptor protein expression may be done in a similar fashion except that quadriceps from different mice are harvested at different times. Persistence of TR1 receptor DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using TR1 receptor naked DNA.

EXAMPLE 15

Gene Therapy Using the Endogenous TR1 Receptor Gene

Another method of gene therapy according to the present invention involves operably associating the endogenous TR1 receptor sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., *Proc. Natl. Acad. Sci. USA* 86:8932–8935 (1989); and Zijlstra et al., *Nature* 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TR1 receptor, flanking the promoter. The targeting sequence will be sufficiently near the 5' end of TR1 receptor so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TR1 receptor sequence. This results in the expression of TR1 receptor in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2

HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the TR1 receptor locus, plasmid pUC18 (MBI Fermentas, Amherst, N.Y.) is digested with HindIII. The CMV promoter is amplified by PCR with an XbaI site on the 5' end and a BamfHI site on the 3' end. Two TR1 receptor non-coding sequences are amplified via PCR: one TR1 receptor non-coding sequence (TR1 receptor fragment 1) is amplified with a HindIII site at the 5' end and an Xba site at the 3'end; the other TR1 receptor non-coding sequence (TR1 receptor fragment 2) is amplified with a BamHI site at the 5' end and a HindIII site at the 3' end. The CMV promoter and TR1 receptor fragments are digested with the appropriate enzymes (CMV promoter—XbaI and BamHI; TR1 receptor fragment 1-XbaI; TR1 receptor fragment 2-BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to of the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 minutes, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

The entire disclosure of all publications cited herein are hereby incorporated by reference.

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −0.23 | −0.01 | * | . | . | 0.30 | 0.98 |
| Asn | 2 | A | A | . | . | . | . | . | −0.51 | 0.24 | * | . | . | −0.30 | 0.63 |
| Lys | 3 | A | A | . | . | . | . | . | −0.79 | 0.39 | * | . | . | −0.30 | 0.27 |
| Leu | 4 | A | A | . | . | . | . | . | −0.99 | 0.53 | * | . | . | −0.60 | 0.14 |
| Leu | 5 | A | A | . | . | . | . | . | −1.41 | 0.41 | . | . | . | −0.60 | 0.09 |
| Cys | 6 | A | A | . | . | . | . | . | −1.67 | 0.70 | * | . | . | −0.60 | 0.04 |
| Cys | 7 | A | A | . | . | . | . | . | −2.37 | 1.34 | * | . | . | −0.60 | 0.03 |
| Ala | 8 | A | A | . | . | . | . | . | −3.22 | 1.44 | * | . | . | −0.60 | 0.04 |
| Leu | 9 | A | A | . | . | . | . | . | −2.41 | 1.44 | . | . | . | −0.60 | 0.05 |
| Val | 10 | A | A | . | . | . | . | . | −2.49 | 0.87 | . | * | . | −0.60 | 0.17 |
| Phe | 11 | A | A | . | . | . | . | . | −2.12 | 0.99 | . | * | . | −0.60 | 0.12 |
| Leu | 12 | A | A | . | . | . | . | . | −2.34 | 0.87 | . | * | . | −0.60 | 0.19 |
| Asp | 13 | A | A | . | . | . | . | . | −1.71 | 0.87 | . | * | . | −0.60 | 0.18 |
| Ile | 14 | A | A | . | . | . | . | . | −1.19 | 0.23 | . | * | . | −0.30 | 0.42 |
| Ser | 15 | A | A | . | . | . | . | . | −0.64 | 0.36 | . | * | . | −0.30 | 0.53 |
| Ile | 16 | . | . | . | B | . | . | C | −0.26 | 0.16 | * | * | . | −0.10 | 0.46 |
| Lys | 17 | . | . | . | B | T | . | . | 0.56 | 0.64 | . | * | F | −0.05 | 0.94 |
| Trp | 18 | . | . | . | B | . | . | C | 0.56 | 0.36 | . | * | F | 0.20 | 1.22 |
| Thr | 19 | . | . | . | B | . | . | C | 1.13 | −0.03 | . | * | F | 0.80 | 3.01 |
| Thr | 20 | . | . | . | B | . | . | C | 0.73 | −0.23 | . | * | F | 0.80 | 2.17 |
| Gln | 21 | . | . | . | B | T | . | . | 1.41 | 0.56 | . | * | F | 0.34 | 1.79 |
| Glu | 22 | . | . | . | B | T | . | . | 1.16 | 0.07 | . | * | F | 0.88 | 1.92 |
| Thr | 23 | . | . | . | . | T | . | . | 1.49 | 0.01 | . | * | F | 1.32 | 2.05 |
| Phe | 24 | . | . | . | . | . | . | C | 1.56 | −0.47 | . | . | F | 1.96 | 2.37 |
| Pro | 25 | . | . | . | . | . | T | C | 1.06 | −0.11 | . | . | F | 2.40 | 2.15 |
| Pro | 26 | . | . | . | . | T | T | . | 1.02 | 0.57 | . | . | F | 1.46 | 1.23 |
| Lys | 27 | . | . | . | . | T | T | . | 0.78 | 0.59 | . | . | F | 1.22 | 1.93 |
| Tyr | 28 | . | . | . | . | . | T | C | 1.09 | 0.56 | . | . | . | 0.63 | 1.95 |
| Leu | 29 | . | A | . | . | . | . | C | 1.79 | 0.13 | . | . | . | 0.29 | 2.11 |
| His | 30 | . | A | . | . | . | . | C | 2.00 | −0.30 | . | . | . | 0.65 | 1.83 |
| Tyr | 31 | A | A | . | . | . | . | . | 1.90 | −0.30 | . | . | . | 0.45 | 2.02 |
| Asp | 32 | A | A | . | . | . | . | . | 1.56 | −0.57 | . | . | F | 0.90 | 3.53 |
| Glu | 33 | A | A | . | . | . | . | . | 1.77 | −0.87 | . | . | F | 0.90 | 3.48 |
| Glu | 34 | A | A | . | . | . | . | . | 2.58 | −0.87 | . | * | F | 0.90 | 3.02 |
| Thr | 35 | A | . | . | . | . | T | . | 1.80 | −1.23 | . | . | F | 1.30 | 3.13 |
| Ser | 36 | A | . | . | . | . | T | . | 1.23 | −0.54 | . | . | F | 1.30 | 1.49 |
| His | 37 | A | . | . | . | . | T | . | 0.57 | 0.14 | . | . | . | 0.10 | 0.71 |
| Gln | 38 | A | . | . | . | . | T | . | 0.57 | 0.71 | . | . | . | −0.20 | 0.26 |
| Leu | 39 | A | . | . | . | . | . | . | 0.61 | 0.23 | . | . | . | −0.10 | 0.33 |
| Leu | 40 | . | . | . | . | T | . | . | 0.26 | −0.16 | . | . | . | 1.17 | 0.48 |
| Cys | 41 | . | . | . | . | T | T | . | 0.34 | −0.09 | . | . | . | 1.64 | 0.15 |
| Asp | 42 | . | . | . | . | T | T | . | 0.17 | −0.06 | . | . | F | 2.06 | 0.28 |
| Lys | 43 | . | . | . | . | T | T | . | −0.18 | −0.31 | . | . | F | 2.33 | 0.53 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Cys | 44 | . | . | . | . | . | T | C | 0.32 | −0.57 | . | . | F | 2.70 | 0.97 |
| Pro | 45 | . | . | . | . | . | T | C | 0.89 | −0.66 | . | . | F | 2.43 | 0.84 |
| Pro | 46 | . | . | . | . | T | T | . | 0.74 | 0.10 | . | . | F | 1.46 | 0.66 |
| Gly | 47 | . | . | . | . | T | T | . | 0.79 | 0.79 | . | . | F | 1.04 | 1.01 |
| Thr | 48 | . | . | . | . | T | T | . | 0.74 | 0.21 | . | . | F | 1.07 | 1.31 |
| Tyr | 49 | A | . | . | . | . | . | . | 1.38 | 0.19 | . | . | F | 0.20 | 1.47 |
| Leu | 50 | A | . | . | . | . | . | . | 0.92 | 0.26 | . | . | F | 0.20 | 2.01 |
| Lys | 51 | A | . | . | . | . | . | . | 0.82 | 0.40 | . | . | . | −0.40 | 0.75 |
| Gln | 52 | A | . | . | . | . | . | . | 0.58 | 0.40 | . | * | . | −0.40 | 0.69 |
| His | 53 | A | . | . | . | . | . | . | 0.93 | 0.14 | . | * | . | −0.10 | 0.84 |
| Cys | 54 | A | . | . | . | . | . | . | 0.89 | −0.54 | . | * | . | 0.80 | 0.84 |
| Thr | 55 | A | . | . | . | . | . | . | 1.74 | 0.37 | . | * | . | −0.10 | 0.51 |
| Ala | 56 | A | . | . | . | . | . | . | 1.39 | −0.03 | . | * | . | 0.50 | 0.75 |
| Lys | 57 | . | . | . | B | T | . | . | 0.53 | −0.04 | . | * | F | 1.00 | 2.03 |
| Trp | 58 | . | . | . | B | T | . | . | −0.10 | 0.03 | . | * | F | 0.40 | 1.04 |
| Lys | 59 | . | . | . | B | T | . | . | −0.02 | 0.11 | . | * | F | 0.25 | 0.55 |
| Thr | 60 | . | . | . | B | T | . | . | 0.08 | 0.11 | . | * | . | 0.10 | 0.28 |
| Val | 61 | . | . | . | B | T | . | . | −0.00 | 0.54 | . | * | . | −0.10 | 0.41 |
| Cys | 62 | . | . | . | B | T | . | . | −0.26 | 0.20 | . | * | . | 0.30 | 0.11 |
| Ala | 63 | . | . | B | B | . | . | . | 0.03 | 0.63 | . | . | . | −0.30 | 0.12 |
| Pro | 64 | . | . | . | . | T | . | . | −0.04 | 0.14 | . | . | . | 0.70 | 0.27 |
| Cys | 65 | . | . | . | . | T | T | . | 0.02 | 0.00 | . | . | . | 1.00 | 0.67 |
| Pro | 66 | . | . | . | . | T | T | . | 0.63 | 0.19 | . | . | F | 1.20 | 1.05 |
| Asp | 67 | . | . | . | . | T | T | . | 0.99 | 0.44 | . | . | . | 0.65 | 1.06 |
| His | 68 | . | . | . | . | T | T | . | 1.58 | 0.50 | . | . | . | 0.55 | 2.85 |
| Tyr | 69 | . | . | . | . | T | . | . | 1.49 | −0.07 | . | . | . | 1.15 | 3.08 |
| Tyr | 70 | . | . | . | . | T | . | . | 1.87 | −0.11 | . | . | . | 1.05 | 2.47 |
| Thr | 71 | . | . | . | . | T | T | . | 2.04 | 0.80 | . | . | . | 0.35 | 1.91 |
| Asp | 72 | . | . | . | . | T | T | . | 1.73 | 0.80 | . | . | . | 0.63 | 1.66 |
| Ser | 73 | . | . | . | . | T | T | . | 1.47 | 0.53 | . | . | F | 1.06 | 1.53 |
| Trp | 74 | . | . | . | . | T | T | . | 1.71 | 0.16 | . | . | F | 1.64 | 1.42 |
| His | 75 | . | . | . | . | . | T | C | 1.96 | −0.33 | . | . | F | 2.32 | 1.42 |
| Thr | 76 | . | . | . | . | . | T | T | 1.60 | −0.33 | * | . | F | 2.80 | 1.83 |
| Ser | 77 | . | . | . | . | . | T | T | 0.79 | −0.14 | . | . | F | 2.37 | 0.94 |
| Asp | 78 | . | . | . | . | . | T | T | 0.84 | −0.37 | . | . | F | 2.09 | 0.57 |
| Glu | 79 | . | . | . | . | . | T | . | 0.47 | −0.11 | . | . | . | 1.46 | 0.62 |
| Cys | 80 | . | . | . | . | . | T | . | 0.20 | −0.03 | . | . | . | 1.18 | 0.25 |
| Leu | 81 | . | . | . | . | . | T | . | 0.30 | −0.03 | . | . | . | 0.90 | 0.20 |
| Tyr | 82 | . | . | . | . | . | T | . | −0.26 | 0.40 | . | . | . | 0.00 | 0.18 |
| Cys | 83 | . | . | . | . | . | T | . | −0.92 | 1.04 | . | . | . | 0.00 | 0.24 |
| Ser | 84 | . | . | . | . | . | T | C | −0.88 | 1.04 | . | . | . | 0.00 | 0.16 |
| Pro | 85 | . | . | . | . | . | T | T | −0.21 | 0.36 | . | . | . | 0.50 | 0.20 |
| Val | 86 | . | . | . | . | . | T | T | −0.21 | −0.40 | * | . | . | 1.10 | 0.65 |
| Cys | 87 | A | . | . | . | . | . | T | 0.03 | −0.29 | * | . | . | 0.70 | 0.40 |
| Lys | 88 | A | A | . | . | . | . | . | 0.46 | −0.27 | * | . | . | 0.30 | 0.45 |
| Glu | 89 | A | A | . | . | . | . | . | −0.10 | 0.06 | * | . | . | −0.30 | 0.95 |
| Leu | 90 | A | A | . | . | . | . | . | 0.16 | 0.06 | * | . | . | −0.15 | 1.32 |
| Gln | 91 | A | A | . | . | . | . | . | 1.01 | −0.51 | * | . | . | 0.75 | 1.32 |
| Tyr | 92 | A | A | . | . | . | . | . | 1.68 | −0.11 | * | . | . | 0.45 | 1.32 |
| Val | 93 | A | A | . | . | . | . | . | 0.97 | −0.11 | * | . | . | 0.45 | 2.77 |
| Lys | 94 | A | A | . | . | . | . | . | 0.97 | −0.23 | * | . | F | 0.79 | 0.86 |
| Gln | 95 | A | A | . | . | . | . | . | 1.89 | −0.23 | * | . | F | 1.13 | 0.88 |
| Glu | 96 | A | A | . | . | . | . | . | 1.58 | −0.99 | * | . | F | 1.92 | 2.32 |
| Cys | 97 | . | . | . | . | T | T | . | 1.79 | −1.14 | * | . | F | 3.06 | 1.68 |
| Asn | 98 | . | . | . | . | T | T | . | 2.64 | −0.64 | * | * | F | 3.40 | 1.32 |
| Arg | 99 | . | . | . | . | T | T | . | 2.71 | −0.64 | * | * | F | 3.06 | 1.22 |
| Thr | 100 | . | . | . | . | T | T | . | 1.86 | −0.64 | * | * | F | 2.72 | 4.47 |
| His | 101 | . | . | . | . | T | . | . | 1.19 | −0.57 | * | * | F | 2.18 | 2.06 |
| Asn | 102 | . | . | . | . | T | . | . | 1.86 | −0.40 | * | * | . | 1.24 | 0.56 |
| Arg | 103 | . | A | . | . | T | . | . | 1.19 | −0.40 | * | * | . | 0.70 | 0.68 |
| Val | 104 | A | A | . | . | . | . | . | 1.12 | −0.31 | * | * | . | 0.30 | 0.27 |
| Cys | 105 | . | A | . | . | T | . | . | 1.43 | −0.81 | . | . | . | 1.00 | 0.33 |
| Glu | 106 | A | A | . | . | . | . | . | 1.12 | −1.21 | . | * | . | 0.60 | 0.29 |
| Cys | 107 | A | . | . | . | . | T | . | 1.23 | −0.79 | . | * | . | 1.00 | 0.39 |
| Lys | 108 | A | . | . | . | . | T | . | 0.88 | −1.43 | . | * | F | 1.30 | 1.43 |
| Glu | 109 | A | . | . | . | . | T | . | 0.92 | −1.24 | . | . | F | 1.30 | 1.29 |
| Gly | 110 | A | . | . | . | . | T | . | 1.59 | −0.56 | . | . | F | 1.30 | 1.99 |
| Arg | 111 | A | . | . | . | . | . | . | 0.70 | −1.13 | . | . | F | 0.90 | 1.72 |
| Tyr | 112 | A | A | . | . | . | . | . | 1.37 | −0.44 | * | * | . | 0.30 | 0.70 |
| Leu | 113 | A | A | . | . | . | . | . | 0.62 | −0.44 | * | * | . | 0.45 | 1.22 |
| Glu | 114 | A | A | . | . | . | . | . | −0.04 | −0.09 | . | * | . | 0.30 | 0.54 |
| Ile | 115 | A | A | . | . | . | . | . | −0.51 | 0.49 | . | * | . | −0.60 | 0.18 |
| Glu | 116 | A | A | . | . | . | . | . | −0.58 | 0.41 | . | * | . | −0.60 | 0.18 |
| Phe | 117 | A | A | . | . | . | . | . | −0.37 | −0.27 | . | * | . | 0.30 | 0.21 |
| Cys | 118 | A | A | . | . | . | . | . | 0.56 | 0.23 | . | * | . | −0.30 | 0.41 |
| Leu | 119 | A | A | . | . | . | . | . | 0.26 | −0.46 | . | * | . | 0.64 | 0.47 |
| Lys | 120 | . | A | . | . | T | . | . | 0.48 | −0.07 | . | * | . | 1.38 | 0.72 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| His | 121 | . | . | . | . | . | T | T | . | 0.27 | −0.29 | . | * | F | 2.27 | 0.72 |
| Arg | 122 | . | . | . | . | . | T | T | . | 0.76 | −0.43 | . | * | F | 2.76 | 1.36 |
| Ser | 123 | . | . | . | . | . | T | T | . | 1.08 | −0.69 | . | * | F | 3.40 | 1.05 |
| Cys | 124 | . | . | . | . | . | . | T | C | 1.19 | −0.26 | . | * | F | 2.41 | 0.76 |
| Pro | 125 | . | . | . | . | . | . | T | C | 0.80 | 0.03 | . | * | F | 1.47 | 0.34 |
| Pro | 126 | . | . | . | . | . | . | T | . | −0.02 | 0.46 | * | . | F | 1.03 | 0.25 |
| Gly | 127 | . | . | . | . | . | T | T | . | −0.99 | 0.71 | * | . | F | 0.69 | 0.34 |
| Phe | 128 | . | . | . | . | . | T | T | . | −0.69 | 0.79 | . | . | . | 0.20 | 0.17 |
| Gly | 129 | . | . | B | B | . | . | . | . | −0.61 | 0.76 | . | . | . | −0.60 | 0.19 |
| Val | 130 | . | . | B | B | . | . | . | . | −0.74 | 0.83 | . | . | . | −0.60 | 0.19 |
| Val | 131 | . | . | B | B | . | . | . | . | −0.84 | 0.83 | . | . | . | −0.60 | 0.22 |
| Gln | 132 | . | . | B | B | . | . | . | . | −0.71 | 0.53 | . | . | . | −0.60 | 0.32 |
| Ala | 133 | . | . | . | B | . | . | . | C | −0.01 | 0.53 | . | . | . | −0.06 | 0.66 |
| Gly | 134 | . | . | . | B | . | . | . | C | 0.44 | −0.11 | . | . | F | 1.48 | 1.53 |
| Thr | 135 | . | . | . | . | . | T | T | C | 1.30 | −0.76 | . | . | F | 2.52 | 1.73 |
| Pro | 136 | . | . | . | . | . | . | T | C | 1.84 | −0.76 | . | * | F | 2.86 | 2.76 |
| Glu | 137 | . | . | . | . | . | T | T | . | 0.99 | −0.77 | . | . | F | 3.40 | 4.03 |
| Arg | 138 | . | . | . | . | . | T | T | . | 0.91 | −0.56 | . | . | F | 3.06 | 2.07 |
| Asn | 139 | . | . | . | B | . | T | . | . | 1.30 | −0.47 | . | . | F | 1.87 | 0.72 |
| Thr | 140 | . | . | . | B | . | T | . | . | 1.72 | −0.90 | . | * | F | 1.83 | 0.83 |
| Val | 141 | . | . | . | B | . | T | . | . | 1.27 | −0.90 | . | * | . | 1.34 | 0.83 |
| Cys | 142 | . | . | . | B | . | T | . | . | 1.06 | −0.33 | . | . | . | 1.01 | 0.28 |
| Lys | 143 | . | . | . | B | . | T | . | . | 0.94 | −0.30 | . | * | . | 1.32 | 0.30 |
| Arg | 144 | . | . | . | . | . | T | . | . | 0.60 | −0.79 | * | . | F | 2.28 | 0.67 |
| Cys | 145 | . | . | B | . | . | T | . | . | 0.21 | −1.00 | * | . | F | 2.54 | 1.23 |
| Pro | 146 | . | . | . | . | . | T | T | . | 0.37 | −0.79 | * | . | F | 3.10 | 0.53 |
| Asp | 147 | . | . | . | . | . | T | T | . | 0.73 | 0.00 | * | . | F | 1.89 | 0.24 |
| Gly | 148 | . | . | . | . | . | T | T | . | 0.69 | 0.39 | * | . | F | 1.58 | 0.59 |
| Phe | 149 | . | . | . | . | . | . | . | C | 0.58 | 0.21 | * | . | . | 0.72 | 0.61 |
| Phe | 150 | . | . | . | . | . | T | T | C | 0.93 | −0.21 | . | . | . | 1.55 | 0.63 |
| Ser | 151 | . | . | . | . | . | T | T | C | 0.84 | 0.27 | . | . | F | 1.13 | 0.93 |
| Asn | 152 | . | . | . | . | . | T | T | . | 0.54 | 0.23 | . | . | F | 1.82 | 1.43 |
| Glu | 153 | . | . | . | . | . | T | T | . | 0.93 | −0.17 | . | . | F | 2.76 | 2.22 |
| Thr | 154 | . | . | . | . | . | T | T | . | 1.04 | −0.96 | . | . | F | 3.40 | 3.31 |
| Ser | 155 | . | . | . | . | . | T | T | . | 1.53 | −0.84 | . | * | F | 3.06 | 2.08 |
| Ser | 156 | . | . | . | . | . | T | T | . | 1.17 | −0.81 | * | * | F | 3.06 | 1.86 |
| Lys | 157 | A | . | . | . | . | . | T | . | 1.28 | −0.24 | . | * | F | 2.21 | 0.69 |
| Ala | 158 | A | . | . | . | . | . | T | . | 1.32 | −0.73 | . | * | F | 2.66 | 1.01 |
| Pro | 159 | A | . | . | . | . | . | T | . | 1.60 | −1.11 | . | * | F | 2.66 | 1.50 |
| Cys | 160 | . | . | . | . | . | T | T | . | 1.59 | −1.00 | * | * | F | 3.40 | 1.02 |
| Arg | 161 | . | . | . | . | . | T | T | . | 1.89 | −0.51 | * | * | F | 3.06 | 1.46 |
| Lys | 162 | . | . | . | . | . | T | . | . | 1.18 | −0.61 | * | * | F | 2.56 | 1.52 |
| His | 163 | . | . | . | . | . | T | T | . | 1.47 | −0.47 | * | * | F | 2.16 | 1.52 |
| Thr | 164 | . | . | . | . | . | T | T | . | 0.82 | −0.66 | * | * | F | 2.16 | 1.04 |
| Asn | 165 | . | . | . | . | . | T | T | . | 0.79 | −0.01 | . | * | . | 1.26 | 0.39 |
| Cys | 166 | . | . | . | . | . | T | T | . | 0.33 | 0.77 | . | * | . | 0.40 | 0.25 |
| Ser | 167 | . | . | . | . | B | T | . | . | −0.52 | 0.70 | . | . | . | −0.04 | 0.17 |
| Val | 168 | . | . | . | . | B | T | . | . | −1.30 | 0.90 | . | . | . | −0.08 | 0.09 |
| Phe | 169 | A | . | . | . | B | . | . | . | −1.80 | 1.19 | . | . | . | −0.52 | 0.13 |
| Gly | 170 | A | . | . | . | B | . | . | . | −2.11 | 1.30 | . | . | . | −0.56 | 0.08 |
| Leu | 171 | A | . | . | . | B | . | . | . | −1.44 | 1.40 | . | . | . | −0.60 | 0.16 |
| Leu | 172 | A | . | . | . | B | . | . | . | −1.10 | 1.16 | . | . | . | −0.60 | 0.32 |
| Leu | 173 | A | . | . | . | B | . | . | . | −0.59 | 0.37 | . | * | F | 0.13 | 0.64 |
| Thr | 174 | A | . | . | . | B | . | . | . | 0.11 | 0.37 | . | * | F | 0.41 | 0.77 |
| Gln | 175 | A | . | . | . | . | . | T | . | −0.13 | 0.09 | . | * | F | 1.24 | 1.50 |
| Lys | 176 | . | . | . | . | . | T | T | . | 0.37 | −0.10 | . | * | F | 2.52 | 1.84 |
| Gly | 177 | . | . | . | . | . | T | T | . | 1.14 | −0.30 | . | * | F | 2.80 | 1.84 |
| Asn | 178 | . | . | . | . | . | T | T | . | 1.96 | −0.29 | . | * | F | 2.52 | 1.45 |
| Ala | 179 | . | . | . | . | . | . | . | C | 2.27 | −0.69 | . | . | F | 2.14 | 1.21 |
| Thr | 180 | . | . | . | . | . | . | . | C | 1.38 | −0.29 | * | . | F | 1.56 | 1.96 |
| His | 181 | . | . | . | . | . | T | T | . | 0.67 | −0.03 | . | * | . | 1.38 | 0.86 |
| Asp | 182 | . | . | . | . | . | T | T | . | 0.71 | 0.14 | . | . | . | 0.50 | 0.45 |
| Asn | 183 | . | . | . | . | . | T | T | . | 0.37 | 0.03 | . | . | . | 0.50 | 0.42 |
| Ile | 184 | . | . | . | . | . | T | T | . | 0.96 | −0.03 | . | . | . | 1.10 | 0.31 |
| Cys | 185 | . | . | . | . | . | T | T | . | 0.97 | −0.13 | . | . | . | 1.10 | 0.30 |
| Ser | 186 | . | . | . | . | . | T | T | . | 1.00 | 0.26 | . | . | F | 0.95 | 0.25 |
| Gly | 187 | . | . | . | . | . | T | T | . | 0.70 | −0.14 | . | . | F | 1.85 | 0.61 |
| Asn | 188 | . | . | . | . | . | T | T | . | 0.39 | −0.44 | . | . | F | 2.30 | 1.52 |
| Ser | 189 | . | . | . | . | . | . | . | C | 1.28 | −0.53 | . | . | F | 2.50 | 1.64 |
| Glu | 190 | . | . | . | . | . | T | . | . | 1.99 | −0.51 | . | . | F | 3.00 | 2.87 |
| Ser | 191 | . | . | . | . | . | T | . | . | 1.62 | −0.94 | . | . | F | 2.70 | 3.56 |
| Thr | 192 | . | . | . | . | . | T | . | . | 1.62 | −0.77 | . | * | F | 2.62 | 1.43 |
| Gln | 193 | . | . | . | . | . | T | T | . | 0.73 | −0.73 | . | * | F | 2.59 | 0.81 |
| Lys | 194 | . | . | . | . | . | T | . | . | 1.03 | −0.04 | . | * | F | 2.21 | 0.43 |
| Cys | 195 | . | . | . | . | . | T | T | . | 0.18 | −0.43 | * | * | F | 2.13 | 0.49 |
| Gly | 196 | . | . | . | . | . | T | T | . | 0.17 | −0.27 | . | * | . | 2.20 | 0.21 |
| Ile | 197 | . | . | . | B | . | T | . | . | −0.33 | −0.19 | . | * | . | 1.58 | 0.15 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 198 | . | A | B | B | . | . | . | −1.00 | 0.50 | . | * | . | 0.06 | 0.23 |
| Val | 199 | . | A | B | B | . | . | . | −1.04 | 0.50 | . | * | . | −0.16 | 0.13 |
| Thr | 200 | A | A | . | B | . | . | . | −0.38 | 0.07 | . | * | . | −0.08 | 0.31 |
| Leu | 201 | A | A | . | B | . | . | . | −0.62 | −0.61 | . | * | . | 0.60 | 0.33 |
| Cys | 202 | A | A | . | B | . | . | . | −0.43 | −0.11 | . | * | . | 0.30 | 0.44 |
| Glu | 203 | A | A | . | B | . | . | . | −1.13 | 0.03 | * | * | . | −0.30 | 0.27 |
| Glu | 204 | A | A | . | . | . | . | . | −0.17 | 0.33 | * | * | . | −0.30 | 0.28 |
| Ala | 205 | A | A | . | B | . | . | . | −0.56 | −0.36 | * | * | . | 0.45 | 1.02 |
| Phe | 206 | A | A | . | B | . | . | . | −0.33 | −0.14 | . | * | . | 0.30 | 0.51 |
| Phe | 207 | A | A | . | B | . | . | . | −0.52 | 0.36 | * | * | . | −0.30 | 0.30 |
| Arg | 208 | A | A | . | B | . | . | . | −0.73 | 1.00 | * | * | . | −0.60 | 0.22 |
| Phe | 209 | A | A | . | B | . | . | . | −1.04 | 0.93 | * | * | . | −0.60 | 0.39 |
| Ala | 210 | A | A | . | B | . | . | . | −0.41 | 0.63 | . | * | . | −0.60 | 0.65 |
| Val | 211 | . | A | . | B | . | . | C | −0.41 | −0.16 | . | * | . | 0.50 | 0.66 |
| Pro | 212 | . | A | . | B | . | . | C | −0.02 | 0.63 | . | * | F | −0.25 | 0.66 |
| Thr | 213 | . | . | . | B | T | . | . | −0.34 | 0.33 | . | * | F | 0.25 | 0.95 |
| Lys | 214 | . | . | . | B | T | . | . | 0.36 | 0.26 | . | * | F | 0.40 | 1.98 |
| Phe | 215 | . | . | . | . | . | . | C | 0.66 | 0.01 | . | * | F | 0.40 | 2.06 |
| Thr | 216 | . | . | . | . | . | T | C | 0.70 | 0.50 | * | * | F | 0.30 | 1.50 |
| Pro | 217 | . | . | . | . | . | T | C | 0.61 | 0.70 | . | * | F | 0.15 | 0.62 |
| Asn | 218 | . | . | . | . | T | T | . | 0.07 | 1.09 | * | * | . | 0.20 | 0.96 |
| Trp | 219 | . | . | . | . | T | T | . | −0.79 | 0.94 | * | * | . | 0.20 | 0.49 |
| Leu | 220 | . | . | . | B | . | . | C | −0.94 | 1.14 | * | * | . | −0.40 | 0.26 |
| Ser | 221 | . | . | B | B | . | . | . | −0.63 | 1.36 | * | . | . | −0.60 | 0.12 |
| Val | 222 | . | . | B | B | . | . | . | −0.42 | 0.96 | * | . | . | −0.60 | 0.19 |
| Leu | 223 | . | . | B | B | . | . | . | −1.23 | 0.44 | * | . | . | −0.60 | 0.37 |
| Val | 224 | . | . | B | B | . | . | . | −1.16 | 0.44 | * | . | . | −0.60 | 0.23 |
| Asp | 225 | . | . | . | B | T | . | . | −0.69 | 0.49 | * | . | . | −0.20 | 0.48 |
| Asn | 226 | . | . | . | . | . | . | C | −0.70 | 0.27 | . | . | F | 0.25 | 0.58 |
| Leu | 227 | . | . | . | . | . | T | C | 0.20 | 0.07 | . | . | F | 0.60 | 1.12 |
| Pro | 228 | . | . | . | . | . | T | T | 0.16 | −0.57 | . | . | F | 1.70 | 1.34 |
| Gly | 229 | . | . | . | . | . | T | T | 1.01 | 0.07 | . | * | F | 0.65 | 0.62 |
| Thr | 230 | . | . | . | . | . | T | C | 0.42 | 0.07 | . | * | F | 0.60 | 1.21 |
| Lys | 231 | . | . | . | . | . | . | C | 0.42 | −0.11 | . | * | F | 0.85 | 0.79 |
| Val | 232 | . | A | . | . | . | . | . | 0.93 | −0.54 | . | * | F | 1.10 | 1.38 |
| Asn | 233 | A | . | . | . | . | T | . | 0.29 | −0.59 | . | * | F | 1.30 | 1.28 |
| Ala | 234 | A | . | . | . | . | T | . | 0.63 | −0.43 | * | * | F | 0.85 | 0.48 |
| Glu | 235 | A | . | . | . | . | T | . | 1.06 | −0.43 | * | * | F | 1.00 | 1.11 |
| Ser | 236 | A | . | . | . | . | T | . | 0.12 | −1.07 | * | * | F | 1.30 | 1.35 |
| Val | 237 | A | A | . | . | . | . | . | 1.02 | −0.79 | * | * | F | 0.75 | 0.94 |
| Glu | 238 | A | A | . | . | . | . | . | 1.13 | −1.29 | * | * | F | 0.90 | 1.08 |
| Arg | 239 | A | A | . | . | . | . | . | 1.72 | −1.29 | * | * | F | 0.90 | 1.58 |
| Ile | 240 | A | A | . | . | . | . | . | 1.69 | −1.27 | * | . | F | 1.20 | 3.70 |
| Lys | 241 | A | A | . | . | . | . | . | 1.69 | −1.41 | * | . | F | 1.50 | 2.91 |
| Arg | 242 | A | A | . | . | . | . | . | 2.24 | −1.03 | * | . | F | 1.80 | 1.99 |
| Gln | 243 | . | A | . | . | . | . | C | 2.24 | −0.64 | * | * | F | 2.30 | 3.80 |
| His | 244 | . | . | . | . | . | T | C | 2.13 | −0.93 | * | * | F | 3.00 | 3.29 |
| Ser | 245 | . | . | . | . | . | T | C | 3.02 | −0.93 | * | . | F | 2.70 | 2.91 |
| Ser | 246 | . | . | . | . | . | T | C | 2.67 | −0.53 | . | . | F | 2.40 | 2.91 |
| Gln | 247 | . | . | . | . | . | T | C | 1.86 | −0.44 | * | . | F | 1.80 | 3.09 |
| Glu | 248 | . | A | . | . | T | . | . | 1.86 | −0.16 | . | * | F | 1.30 | 1.99 |
| Gln | 249 | A | A | . | . | . | . | . | 1.08 | −0.14 | . | . | F | 0.60 | 2.58 |
| Thr | 250 | A | A | . | . | . | . | . | 0.57 | 0.16 | * | . | F | 0.00 | 1.23 |
| Phe | 251 | A | A | . | . | . | . | . | 0.91 | 0.44 | . | . | . | −0.60 | 0.58 |
| Gln | 252 | A | A | . | . | . | . | . | 0.10 | 0.44 | * | . | . | −0.60 | 0.67 |
| Leu | 253 | A | A | . | . | . | . | . | −0.19 | 0.73 | * | . | . | −0.60 | 0.39 |
| Leu | 254 | A | A | . | . | . | . | . | −0.14 | 1.16 | * | . | . | −0.60 | 0.47 |
| Lys | 255 | A | A | . | . | . | . | . | 0.13 | 0.37 | * | . | . | −0.30 | 0.54 |
| Leu | 256 | A | A | . | . | . | . | . | 0.83 | 0.47 | * | . | . | −0.60 | 0.89 |
| Trp | 257 | A | A | . | . | . | . | . | 0.83 | 0.19 | * | . | . | −0.15 | 1.87 |
| Lys | 258 | A | A | . | . | . | . | . | 1.69 | −0.10 | * | . | F | 0.60 | 1.51 |
| His | 259 | A | A | . | . | . | . | . | 2.50 | −0.10 | * | . | F | 0.60 | 3.65 |
| Gln | 260 | A | A | . | . | . | . | . | 2.46 | −0.79 | * | . | F | 0.90 | 5.80 |
| Asn | 261 | . | . | . | . | T | T | . | 3.27 | −1.30 | . | . | F | 1.70 | 5.02 |
| Lys | 262 | A | . | . | . | . | T | . | 2.67 | −1.30 | * | . | F | 1.30 | 6.17 |
| Asp | 263 | A | . | . | . | . | T | . | 1.77 | −1.11 | * | . | F | 1.30 | 2.50 |
| Gln | 264 | A | . | . | . | . | T | . | 1.84 | −0.87 | * | . | F | 1.30 | 1.15 |
| Asp | 265 | A | . | . | B | . | . | . | 1.89 | −1.27 | * | . | F | 0.90 | 1.15 |
| Ile | 266 | A | . | . | B | . | . | . | 1.00 | −1.27 | * | . | F | 0.90 | 1.38 |
| Val | 267 | A | . | . | B | . | . | . | 0.07 | −0.59 | * | . | F | 0.75 | 0.56 |
| Lys | 268 | A | . | . | B | . | . | . | 0.07 | −0.30 | * | . | . | 0.30 | 0.23 |
| Lys | 269 | A | . | . | B | . | . | . | 0.07 | 0.10 | * | . | . | −0.30 | 0.58 |
| Ile | 270 | A | . | . | B | . | . | . | −0.82 | −0.59 | * | . | . | 0.75 | 1.30 |
| Ile | 271 | A | . | . | B | . | . | . | 0.07 | −0.54 | * | * | . | 0.60 | 0.46 |
| Gln | 272 | A | . | . | B | . | . | . | 0.11 | −0.54 | * | * | . | 0.60 | 0.38 |
| Asp | 273 | . | . | B | B | . | . | . | −0.60 | 0.14 | * | * | . | −0.30 | 0.45 |
| Ile | 274 | A | . | . | B | . | . | . | −0.64 | 0.03 | * | * | . | −0.30 | 0.34 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Asp | 275 | A | . | . | B | . | . | . | 0.24 | −0.66 | * | * | . | 0.60 | 0.34 |
| Leu | 276 | . | . | . | . | T | . | . | 0.83 | −0.66 | * | . | . | 1.20 | 0.33 |
| Cys | 277 | . | . | . | . | T | T | . | −0.02 | −0.27 | * | * | . | 1.10 | 0.63 |
| Glu | 278 | A | . | . | . | . | T | . | −0.02 | −0.31 | * | * | F | 0.85 | 0.28 |
| Asn | 279 | A | . | . | . | . | T | . | 0.98 | 0.09 | * | . | F | 0.25 | 0.59 |
| Ser | 280 | A | . | . | . | . | T | . | 0.94 | −0.60 | * | . | F | 1.30 | 2.15 |
| Val | 281 | A | . | . | B | . | . | . | 0.87 | −0.67 | * | . | F | 0.90 | 1.69 |
| Gln | 282 | A | . | . | B | . | . | . | 1.19 | 0.01 | * | . | F | −0.15 | 0.74 |
| Arg | 283 | A | . | . | B | . | . | . | 1.16 | 0.04 | * | . | . | −0.30 | 0.54 |
| His | 284 | A | . | . | B | . | . | . | 0.57 | 0.16 | * | . | . | −0.30 | 1.00 |
| Ile | 285 | . | . | . | B | . | . | C | 0.87 | 0.01 | * | * | . | −0.10 | 0.58 |
| Gly | 286 | . | . | . | . | . | . | C | 0.91 | 0.01 | * | * | . | 0.10 | 0.48 |
| His | 287 | . | . | . | . | . | . | C | 0.60 | 0.70 | * | * | . | −0.20 | 0.29 |
| Ala | 288 | . | . | . | . | . | . | C | −0.21 | 0.69 | * | * | . | −0.20 | 0.60 |
| Asn | 289 | . | . | . | . | . | . | C | −0.18 | 0.79 | . | * | . | −0.20 | 0.52 |
| Leu | 290 | . | A | . | . | . | . | C | 0.71 | 0.36 | * | * | . | −0.10 | 0.66 |
| Thr | 291 | A | A | . | . | . | . | . | 0.24 | 0.26 | . | * | . | −0.15 | 1.14 |
| Phe | 292 | A | A | . | . | . | . | . | 0.39 | 0.44 | * | * | . | −0.60 | 0.58 |
| Glu | 293 | A | A | . | . | . | . | . | 0.68 | 0.04 | * | * | . | −0.15 | 1.39 |
| Gln | 294 | A | A | . | . | . | . | . | −0.13 | −0.26 | * | * | F | 0.60 | 1.29 |
| Leu | 295 | A | A | . | . | . | . | . | 0.08 | −0.06 | * | * | F | 0.60 | 1.23 |
| Arg | 296 | A | A | . | . | . | . | . | 0.39 | −0.23 | * | * | F | 0.45 | 0.70 |
| Ser | 297 | A | A | . | . | . | . | . | 0.79 | −0.23 | * | . | . | 0.30 | 0.70 |
| Leu | 298 | A | A | . | . | . | . | . | −0.02 | −0.24 | * | * | . | 0.45 | 1.14 |
| Met | 299 | A | A | . | . | . | . | . | −0.23 | −0.24 | * | * | . | 0.30 | 0.48 |
| Glu | 300 | A | A | . | . | . | . | . | 0.23 | 0.19 | * | * | . | −0.30 | 0.55 |
| Ser | 301 | A | . | . | . | . | . | . | 0.17 | 0.23 | . | . | F | 0.05 | 0.66 |
| Leu | 302 | A | . | . | . | . | T | . | 0.51 | −0.46 | . | . | F | 1.00 | 1.34 |
| Pro | 303 | A | . | . | . | . | T | . | 0.47 | −1.07 | * | . | F | 1.30 | 1.55 |
| Gly | 304 | . | . | . | . | T | T | . | 0.72 | −0.43 | * | . | F | 1.25 | 0.86 |
| Lys | 305 | A | . | . | . | . | T | . | 0.13 | −0.39 | * | . | F | 1.00 | 1.03 |
| Lys | 306 | A | A | . | . | . | . | . | 0.43 | −0.57 | . | . | F | 0.75 | 0.67 |
| Val | 307 | A | A | . | . | . | . | . | 1.24 | −1.00 | . | . | F | 0.90 | 1.18 |
| Gly | 308 | A | A | . | . | . | . | . | 0.57 | −1.43 | * | . | F | 0.75 | 0.98 |
| Ala | 309 | A | A | . | . | . | . | . | 0.91 | −0.74 | * | . | F | 0.75 | 0.34 |
| Glu | 310 | A | A | . | . | . | . | . | 0.91 | −0.74 | * | . | F | 0.75 | 0.80 |
| Asp | 311 | A | A | . | . | . | . | . | 0.56 | −1.39 | * | * | F | 0.90 | 1.63 |
| Ile | 312 | A | A | . | . | . | . | . | 0.52 | −1.33 | * | * | F | 0.90 | 2.32 |
| Glu | 313 | A | A | . | . | . | . | . | 0.91 | −1.14 | * | * | F | 0.75 | 0.94 |
| Lys | 314 | A | A | . | . | . | . | . | 0.91 | −1.14 | * | * | F | 0.90 | 1.13 |
| Thr | 315 | A | A | . | . | . | . | . | 0.24 | −0.64 | * | * | F | 0.90 | 1.62 |
| Ile | 316 | A | A | . | . | . | . | . | 0.29 | −0.76 | * | * | F | 0.75 | 0.50 |
| Lys | 317 | A | A | . | . | . | . | . | 0.97 | −0.76 | * | * | F | 0.75 | 0.50 |
| Ala | 318 | A | A | . | . | T | . | . | 0.67 | −0.33 | * | . | . | 0.70 | 0.54 |
| Cys | 319 | . | A | . | . | T | . | . | 0.62 | −0.43 | * | . | . | 0.85 | 1.03 |
| Lys | 320 | A | A | . | . | . | . | . | 0.93 | −1.11 | * | * | F | 0.75 | 0.86 |
| Pro | 321 | A | . | . | . | . | T | . | 0.93 | −0.71 | * | . | F | 1.30 | 1.47 |
| Ser | 322 | A | . | . | . | . | T | . | 0.08 | −0.53 | * | . | F | 1.30 | 1.93 |
| Asp | 323 | A | . | . | . | . | T | . | 0.71 | −0.41 | * | . | F | 0.85 | 0.79 |
| Gln | 324 | A | . | . | . | . | T | . | 0.57 | −0.41 | * | . | F | 1.00 | 1.03 |
| Ile | 325 | A | . | . | B | . | . | . | −0.29 | −0.16 | * | . | . | 0.30 | 0.63 |
| Leu | 326 | A | . | . | B | . | . | . | −0.38 | 0.14 | * | . | . | −0.30 | 0.31 |
| Lys | 327 | A | . | . | B | . | . | . | −0.89 | 0.53 | * | . | . | −0.60 | 0.24 |
| Leu | 328 | A | . | . | B | . | . | . | −1.18 | 0.81 | * | * | . | −0.60 | 0.28 |
| Leu | 329 | A | . | . | B | . | . | . | −1.07 | 1.04 | . | * | . | −0.60 | 0.36 |
| Ser | 330 | A | . | . | B | . | . | . | −1.07 | 0.36 | . | * | . | −0.30 | 0.35 |
| Leu | 331 | A | . | . | B | . | . | . | −0.21 | 1.04 | . | * | . | −0.60 | 0.30 |
| Trp | 332 | A | . | . | B | . | . | . | −0.26 | 0.36 | . | * | . | 0.04 | 0.73 |
| Arg | 333 | A | . | . | B | . | . | . | 0.21 | 0.07 | . | * | . | 0.38 | 0.88 |
| Ile | 334 | . | . | . | B | T | . | . | 1.02 | 0.11 | . | * | F | 1.42 | 1.05 |
| Lys | 335 | . | . | . | B | T | . | . | 1.32 | −0.57 | * | * | F | 2.66 | 1.67 |
| Asn | 336 | . | . | . | . | T | T | . | 2.13 | −1.09 | * | * | F | 3.40 | 1.48 |
| Gly | 337 | . | . | . | . | T | T | . | 2.11 | −1.09 | * | * | F | 3.06 | 3.52 |
| Asp | 338 | . | . | . | . | T | T | . | 1.19 | −1.29 | * | * | F | 2.72 | 2.54 |
| Gln | 339 | . | . | . | . | . | T | C | 2.12 | −0.60 | * | . | F | 2.18 | 1.30 |
| Asp | 340 | A | . | . | . | . | . | . | 1.73 | −1.00 | * | . | F | 1.44 | 2.64 |
| Thr | 341 | A | . | . | . | . | . | . | 0.92 | −1.00 | * | . | F | 1.10 | 1.56 |
| Leu | 342 | A | A | . | . | . | . | . | 0.67 | −0.31 | * | . | F | 0.45 | 0.74 |
| Lys | 343 | A | A | . | . | . | . | . | 0.63 | −0.10 | * | * | F | 0.45 | 0.44 |
| Gly | 344 | A | A | . | . | . | . | . | 0.04 | 0.40 | * | * | . | −0.30 | 0.42 |
| Leu | 345 | A | A | . | . | . | . | . | −0.77 | 0.41 | * | . | . | −0.60 | 0.51 |
| Met | 346 | A | A | . | . | . | . | . | −0.41 | 0.41 | * | . | . | −0.60 | 0.21 |
| His | 347 | A | A | . | . | . | . | . | 0.37 | 0.41 | * | * | . | −0.60 | 0.42 |
| Ala | 348 | A | A | . | . | . | . | . | 0.02 | 0.49 | * | . | . | −0.60 | 0.70 |
| Leu | 349 | A | A | . | . | . | . | . | 0.41 | 0.19 | * | . | . | −0.30 | 0.95 |
| Lys | 350 | A | A | . | . | . | . | . | 0.91 | −0.43 | * | . | . | 0.45 | 1.39 |
| His | 351 | A | A | . | . | . | . | . | 1.27 | −0.44 | . | . | F | 0.60 | 1.99 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 352 | A | . | . | . | . | T | . | 1.27 | −0.19 | . | . | F | 1.00 | 3.78 |
| Lys | 353 | A | . | . | . | . | T | . | 1.16 | −0.37 | . | . | F | 1.00 | 2.57 |
| Thr | 354 | . | . | . | . | T | T | . | 1.76 | 0.41 | . | . | F | 0.50 | 1.64 |
| Tyr | 355 | . | . | . | . | T | T | . | 1.76 | 0.34 | . | . | . | 0.65 | 1.89 |
| His | 356 | . | . | . | . | . | . | C | 1.48 | −0.04 | * | . | . | 0.85 | 1.89 |
| Phe | 357 | . | . | . | . | . | T | C | 0.92 | 0.44 | * | . | . | 0.15 | 1.89 |
| Pro | 358 | . | . | . | . | T | T | . | 0.57 | 0.60 | * | . | F | 0.35 | 0.89 |
| Lys | 359 | . | . | . | . | T | T | . | 0.88 | 0.33 | * | . | F | 0.65 | 0.95 |
| Thr | 360 | A | . | . | . | . | T | . | 0.82 | 0.23 | * | . | F | 0.40 | 1.90 |
| Val | 361 | A | . | . | B | . | . | . | 0.04 | −0.17 | * | . | F | 0.60 | 1.64 |
| Thr | 362 | A | . | . | B | . | . | . | 0.79 | 0.09 | * | . | F | −0.15 | 0.68 |
| Gln | 363 | A | . | . | B | . | . | . | 1.04 | 0.09 | * | . | F | −0.15 | 0.94 |
| Ser | 364 | A | . | . | B | . | . | . | 0.69 | −0.40 | * | . | F | 0.60 | 2.53 |
| Leu | 365 | A | A | . | . | . | . | . | 0.11 | −0.56 | * | * | F | 0.90 | 2.53 |
| Lys | 366 | A | A | . | B | . | . | . | 1.08 | −0.36 | * | * | F | 0.60 | 1.03 |
| Lys | 367 | A | A | . | B | . | . | . | 0.69 | −0.76 | * | * | F | 0.90 | 1.50 |
| Thr | 368 | A | A | . | B | . | . | . | −0.12 | −0.36 | * | * | F | 0.60 | 1.57 |
| Ile | 369 | A | . | . | B | . | . | . | 0.14 | −0.36 | * | * | . | 0.30 | 0.65 |
| Arg | 370 | A | . | . | B | . | . | . | 0.66 | 0.14 | * | * | . | −0.30 | 0.44 |
| Phe | 371 | A | . | . | B | . | . | . | −0.09 | 0.53 | * | * | . | −0.60 | 0.41 |
| Leu | 372 | A | . | . | B | . | . | . | −0.44 | 0.83 | * | * | . | −0.60 | 0.51 |
| His | 373 | A | . | . | B | . | . | . | −0.73 | 0.63 | * | * | . | −0.60 | 0.37 |
| Ser | 374 | . | . | . | B | . | . | C | −0.09 | 1.24 | . | * | . | −0.40 | 0.43 |
| Phe | 375 | A | . | . | B | . | . | . | −0.16 | 1.21 | . | * | . | −0.60 | 0.81 |
| Thr | 376 | A | . | . | B | . | . | . | −0.27 | 0.53 | . | . | . | −0.45 | 1.19 |
| Met | 377 | A | . | . | B | . | . | . | 0.30 | 0.71 | . | . | . | −0.60 | 0.73 |
| Tyr | 378 | A | . | . | B | . | . | . | 0.33 | 1.09 | . | . | . | −0.45 | 1.33 |
| Lys | 379 | A | A | . | B | . | . | . | 0.68 | 0.70 | * | * | . | −0.45 | 1.59 |
| Leu | 380 | A | A | . | B | . | . | . | 0.57 | 0.21 | * | . | . | −0.15 | 3.21 |
| Tyr | 381 | A | A | . | B | . | . | . | 0.18 | 0.29 | * | * | . | −0.15 | 1.69 |
| Gln | 382 | A | A | . | B | . | . | . | −0.03 | 0.31 | * | * | . | −0.30 | 0.73 |
| Lys | 383 | A | A | . | B | . | . | . | 0.21 | 1.00 | * | * | . | −0.60 | 0.73 |
| Leu | 384 | A | A | . | B | . | . | . | −0.43 | 0.31 | * | * | . | −0.30 | 0.81 |
| Phe | 385 | A | A | . | B | . | . | . | −0.51 | 0.17 | . | * | . | −0.30 | 0.46 |
| Leu | 386 | A | A | . | B | . | . | . | −0.61 | 0.46 | * | . | . | −0.60 | 0.16 |
| Glu | 387 | A | A | . | B | . | . | . | −0.61 | 0.89 | . | . | . | −0.60 | 0.19 |
| Met | 388 | A | A | . | B | . | . | . | −0.66 | 0.60 | * | * | . | −0.60 | 0.36 |
| Ile | 389 | A | A | . | B | . | . | . | −0.70 | 0.21 | * | . | . | −0.30 | 0.76 |
| Gly | 390 | A | A | . | B | . | . | . | 0.00 | 0.17 | * | . | . | −0.30 | 0.33 |
| Asn | 391 | A | . | . | B | . | . | . | 0.51 | 0.57 | * | . | F | −0.45 | 0.57 |
| Gln | 392 | A | . | . | B | . | . | . | −0.34 | 0.34 | * | . | F | 0.00 | 1.09 |
| Val | 393 | A | . | . | B | . | . | . | 0.30 | 0.30 | . | * | F | −0.15 | 0.82 |
| Gln | 394 | A | . | . | B | . | . | . | 0.30 | −0.13 | . | * | F | 0.60 | 1.02 |
| Ser | 395 | . | . | . | B | T | . | . | 0.34 | 0.16 | . | * | F | 0.25 | 0.41 |
| Val | 396 | . | . | B | B | . | . | . | −0.32 | 0.14 | . | . | F | −0.15 | 0.74 |
| Lys | 397 | . | . | B | B | . | . | . | −1.13 | 0.07 | . | . | F | −0.15 | 0.23 |
| Ile | 398 | . | . | B | B | . | . | . | −0.67 | 0.36 | . | . | . | −0.30 | 0.14 |
| Ser | 399 | . | . | B | B | . | . | . | −1.06 | 0.40 | . | * | . | −0.30 | 0.24 |
| Cys | 400 | . | . | B | B | . | . | . | −1.14 | 0.19 | . | * | . | −0.30 | 0.16 |
| Leu | 401 | . | . | B | B | . | . | . | −0.68 | 0.61 | . | * | . | −0.60 | 0.28 |

What is claimed is:

1. An isolated antibody, which specifically binds a protein selected from the group consisting of:
   (a) a protein whose sequence consists of the amino acid sequence of SEQ ID NO:2;
   (b) a protein whose sequence consists of amino acids 1 to 380 of SEQ ID NO:2.

2. The antibody of claim 1, which specifically binds a protein whose sequence consists of the amino acid sequence of SEQ ID NO:2.

3. The antibody of claim 1, which specifically binds a protein whose sequence consists of amino acids 1 to 380 of SEQ ID NO:2.

4. The antibody of claim 1, wherein said antibody is polyclonal.

5. The antibody of claim 1, wherein said antibody is monoclonal.

6. The antibody of claim 5, wherein said antibody is produced by a method selected from the group consisting of the hybridoma technique, the trioma technique, the human B-cell hybridoma technique, and the EBV-hybridoma technique.

7. The antibody of claim 1, wherein said antibody is chimeric.

8. The antibody of claim 1, wherein said antibody is humanized.

9. A composition comprising the antibody of claim 1 and a carrier.

10. An isolated antibody fragment, which specifically binds a protein selected from the group consisting of:
    (a) a protein whose sequence consists of the amino acid sequence of SEQ ID NO:2;
    (b) a protein whose sequence consists of amino acids 1 to 380 of SEQ ID NO: 2.

11. The antibody fragment of claim 10, which specifically binds a protein whose sequence consists of the amino acid sequence of SEQ ID NO:2.

12. The antibody fragment of claim 10, which specifically binds a protein whose sequence consists of amino acids 1 to 380 of SEQ ID NO:2.

13. The antibody fragment of claim 10, wherein said antibody fragment comprises a Fab fragment.

14. The antibody fragment of claim 10, wherein said antibody fragment comprises a single chain antibody.

15. The antibody fragment of claim 10, wherein said antibody fragment is chimeric.

16. The antibody fragment of claim 10, wherein said antibody fragment is humanized.

17. The antibody fragment of claim 10, wherein said antibody fragment is the product of an Fab expression library.

18. A composition comprising the antibody fragment of claim 10 and a carrier.

19. An isolated antibody, which specifically binds a protein selected from the group consisting of:
    (a) a protein whose sequence consists of the amino acid sequence encoded by ATCC Deposit No. 75899.

20. The isolated antibody of claim 19, which specifically binds the protein whose sequence consists of the amino acid sequence encoded by ATCC Deposit No. 75899.

21. The antibody of claim 19, wherein said antibody is polyclonal.

22. The antibody of claim 19, wherein said antibody is monoclonal.

23. The antibody of claim 19, wherein said antibody is chimeric.

24. The antibody of claim 19, wherein said antibody is humanized.

25. A composition comprising the antibody of claim 19 and a carrier.

26. An isolated antibody fragment, which specifically binds a protein selected from the group consisting of:
    (a) a protein whose sequence consists of the amino acid sequence encoded by ATCC Deposit No. 75899.

27. The isolated antibody fragment of claim 26, which specifically binds the protein whose sequence consists of the amino acid sequence encoded by ATCC Deposit No. 75899.

28. The antibody fragment of claim 26, wherein said antibody fragment comprises a Fab fragment.

29. The antibody fragment of claim 26, wherein said antibody fragment comprises a single chain antibody.

30. The antibody fragment of claim 26, wherein said antibody fragment is chimeric.

31. The antibody fragment of claim 26, wherein said antibody fragment is humanized.

32. A composition comprising the antibody fragment of claim 26 and a carrier.

* * * * *

SEQUENCE LISTING

<160> NUMBER OF SEQ ID NOS: 11

<210> SEQ ID NO 1
<211> LENGTH: 1527
<212> TYPE: DNA
<213> ORGANISM: Homo sapiens
<220> FEATURE:
<221> NAME/KEY: sig_peptide
<222> LOCATION: (46)..(106)
<220> FEATURE:
<221> NAME/KEY: mat_peptide
<222> LOCATION: (109)..(1248)
<220> FEATURE:
<221> NAME/KEY: CDS
<222> LOCATION: (46)..(1248)

<400> SEQUENCE: 1

```
cgcccagccg ccgcctccaa gcccctgagg tttccgggga ccaca atg aac aag ttg      57
                                                Met Asn Lys Leu
                                                -20 ctg tgc tgc gcg ctc gtg ttt ctg gac atc tcc att aag tgg acc acc       105
Leu Cys Cys Ala Leu Val Phe Leu Asp Ile Ser Ile Lys Trp Thr Thr
    -15                 -10                 -5 cag gaa acg ttt cct cca aag tac ctt cat tat gac gaa gaa acc tct       153
Gln Glu Thr Phe Pro Pro Lys Tyr Leu His Tyr Asp Glu Glu Thr Ser
 -1   1                 5                  10                  15 cat cag ctg ttg tgt gac aaa tgt cct cct ggt acc tac cta aaa caa       201
His Gln Leu Leu Cys Asp Lys Cys Pro Pro Gly Thr Tyr Leu Lys Gln
                 20                  25                  30 cac tgt aca gca aag tgg aag acc gtg tgc gcc cct tgc cct gac cac       249
His Cys Thr Ala Lys Trp Lys Thr Val Cys Ala Pro Cys Pro Asp His
             35                  40                  45 tac tac aca gac agc tgg cac acc agt gac gag tgt cta tac tgc agc       297
Tyr Tyr Thr Asp Ser Trp His Thr Ser Asp Glu Cys Leu Tyr Cys Ser
         50                  55                  60 ccc gtg tgc aag gag ctg cag tac gtc aag cag gag tgc aat cgc acc       345
Pro Val Cys Lys Glu Leu Gln Tyr Val Lys Gln Glu Cys Asn Arg Thr
     65                  70                  75 cac aac cgc gtg tgc gaa tgc aag gaa ggg cgc tac ctt gag ata gag       393
His Asn Arg Val Cys Glu Cys Lys Glu Gly Arg Tyr Leu Glu Ile Glu
 80                  85                  90                  95 ttc tgc ttg aaa cat agg agc tgc cct cct gga ttt gga gtg gtg caa       441
Phe Cys Leu Lys His Arg Ser Cys Pro Pro Gly Phe Gly Val Val Gln
                100                 105                 110 gct gga acc cca gag cga aat aca gtt tgc aaa aga tgt cca gat ggg       489
Ala Gly Thr Pro Glu Arg Asn Thr Val Cys Lys Arg Cys Pro Asp Gly
            115                 120                 125 ttc ttc tca aat gag acg tca tct aaa gca ccc tgt aga aaa cac aca       537
Phe Phe Ser Asn Glu Thr Ser Ser Lys Ala Pro Cys Arg Lys His Thr
        130                 135                 140 aat tgc agt gtc ttt ggt ctc ctg cta act cag aaa gga aat gca aca       585
Asn Cys Ser Val Phe Gly Leu Leu Leu Thr Gln Lys Gly Asn Ala Thr
    145                 150                 155 cac gac aac ata tgt tcc gga aac agt gaa tca act caa aaa tgt gga       633
His Asp Asn Ile Cys Ser Gly Asn Ser Glu Ser Thr Gln Lys Cys Gly
160                 165                 170                 175 ata gat gtt acc ctg tgt gag gag gca ttc ttc agg ttt gct gtt cct       681
Ile Asp Val Thr Leu Cys Glu Glu Ala Phe Phe Arg Phe Ala Val Pro
                180                 185                 190 aca aag ttt acg cct aac tgg ctt agt gtc ttg gta gac aat ttg cct       729
Thr Lys Phe Thr Pro Asn Trp Leu Ser Val Leu Val Asp Asn Leu Pro
            195                 200                 205 ggc acc aaa gta aac gca gag agt gta gag agg ata aaa cgg caa cac       777
Gly Thr Lys Val Asn Ala Glu Ser Val Glu Arg Ile Lys Arg Gln His
        210                 215                 220 agc tca caa gaa cag act ttc cag ctg ctg aag tta tgg aaa cat caa       825
Ser Ser Gln Glu Gln Thr Phe Gln Leu Leu Lys Leu Trp Lys His Gln
    225                 230                 235 aac aaa gac caa gat ata gtc aag aag atc atc caa gat att gac ctc       873
Asn Lys Asp Gln Asp Ile Val Lys Lys Ile Ile Gln Asp Ile Asp Leu
240                 245                 250                 255 tgt gaa aac agc gtg cag cgg cac att gga cat gct aac ctc acc ttc       921
Cys Glu Asn Ser Val Gln Arg His Ile Gly His Ala Asn Leu Thr Phe
                260                 265                 270 gag cag ctt cgt agc ttg atg gaa agc tta ccg gga aag aaa gtg gga       969
Glu Gln Leu Arg Ser Leu Met Glu Ser Leu Pro Gly Lys Lys Val Gly
            275                 280                 285
```

```
gca gaa gac att gaa aaa aca ata aag gca tgc aaa ccc agt gac cag    1017
Ala Glu Asp Ile Glu Lys Thr Ile Lys Ala Cys Lys Pro Ser Asp Gln
        290                 295                 300 atc ctg aag ctg ctc agt ttg tgg cga ata aaa aat ggc gac caa gac    1065
Ile Leu Lys Leu Leu Ser Leu Trp Arg Ile Lys Asn Gly Asp Gln Asp
    305                 310                 315 acc ttg aag ggc cta atg cac gca cta aag cac tca aag acg tac cac    1113
Thr Leu Lys Gly Leu Met His Ala Leu Lys His Ser Lys Thr Tyr His
320                 325                 330                 335 ttt ccc aaa act gtc act cag agt cta aag aag acc atc agg ttc ctt    1161
Phe Pro Lys Thr Val Thr Gln Ser Leu Lys Lys Thr Ile Arg Phe Leu
                340                 345                 350 cac agc ttc aca atg tac aaa ttg tat cag aag tta ttt tta gaa atg    1209
His Ser Phe Thr Met Tyr Lys Leu Tyr Gln Lys Leu Phe Leu Glu Met
            355                 360                 365 ata ggt aac cag gtc caa tca gta aaa ata agc tgc tta taactggaaa    1258
Ile Gly Asn Gln Val Gln Ser Val Lys Ile Ser Cys Leu
        370                 375                 380 tggccattga gctgtttcct cacaattggc gagatcccat ggatgagtaa actgtttctc    1318
aggcacttga ggctttcagt gatatctttc tcattaccag tgactaattt tgccacaggg    1378
tactaaaaga aactatgatg tggagaaagg actaacatct cctccaataa accccaaatg    1438
gttaatccaa ctgtcagatc tggatcgtta tctactgact atattttccc ttattactgc    1498
ttgcagtaat tcaactggaa aaaaaaaaa                                      1527

<210> SEQ ID NO 2
<211> LENGTH: 401
<212> TYPE: PRT
<213> ORGANISM: Homo sapiens

<400> SEQUENCE: 2

Met Asn Lys Leu Leu Cys Cys Ala Leu Val Phe Leu Asp Ile Ser Ile
        -20                 -15                 -10

Lys Trp Thr Thr Gln Glu Thr Phe Pro Pro Lys Tyr Leu His Tyr Asp
-5                   -1  1               5                   10

Glu Glu Thr Ser His Gln Leu Leu Cys Asp Lys Cys Pro Pro Gly Thr
                15                  20                  25

Tyr Leu Lys Gln His Cys Thr Ala Lys Trp Lys Thr Val Cys Ala Pro
            30                  35                  40

Cys Pro Asp His Tyr Tyr Thr Asp Ser Trp His Thr Ser Asp Glu Cys
        45                  50                  55

Leu Tyr Cys Ser Pro Val Cys Lys Glu Leu Gln Tyr Val Lys Gln Glu
60                  65                  70                  75

Cys Asn Arg Thr His Asn Arg Val Cys Glu Cys Lys Glu Gly Arg Tyr
                80                  85                  90

Leu Glu Ile Glu Phe Cys Leu Lys His Arg Ser Cys Pro Pro Gly Phe
            95                  100                 105

Gly Val Val Gln Ala Gly Thr Pro Glu Arg Asn Thr Val Cys Lys Arg
        110                 115                 120

Cys Pro Asp Gly Phe Phe Ser Asn Glu Thr Ser Ser Lys Ala Pro Cys
    125                 130                 135

Arg Lys His Thr Asn Cys Ser Val Phe Gly Leu Leu Leu Thr Gln Lys
140                 145                 150                 155

Gly Asn Ala Thr His Asp Asn Ile Cys Ser Gly Asn Ser Glu Ser Thr
                160                 165                 170
```

```
Gln Lys Cys Gly Ile Asp Val Thr Leu Cys Glu Glu Ala Phe Phe Arg
            175                 180                 185

Phe Ala Val Pro Thr Lys Phe Thr Pro Asn Trp Leu Ser Val Leu Val
        190                 195                 200

Asp Asn Leu Pro Gly Thr Lys Val Asn Ala Glu Ser Val Glu Arg Ile
    205                 210                 215

Lys Arg Gln His Ser Ser Gln Glu Gln Thr Phe Gln Leu Leu Lys Leu
220                 225                 230                 235

Trp Lys His Gln Asn Lys Asp Gln Asp Ile Val Lys Ile Ile Gln
                240                 245                 250

Asp Ile Asp Leu Cys Glu Asn Ser Val Gln Arg His Ile Gly His Ala
            255                 260                 265

Asn Leu Thr Phe Glu Gln Leu Arg Ser Leu Met Glu Ser Leu Pro Gly
        270                 275                 280

Lys Lys Val Gly Ala Glu Asp Ile Glu Lys Thr Ile Lys Ala Cys Lys
285                 290                 295

Pro Ser Asp Gln Ile Leu Lys Leu Leu Ser Leu Trp Arg Ile Lys Asn
300                 305                 310                 315

Gly Asp Gln Asp Thr Leu Lys Gly Leu Met His Ala Leu Lys His Ser
                320                 325                 330

Lys Thr Tyr His Phe Pro Lys Thr Val Thr Gln Ser Leu Lys Lys Thr
            335                 340                 345

Ile Arg Phe Leu His Ser Phe Thr Met Tyr Lys Leu Tyr Gln Lys Leu
        350                 355                 360

Phe Leu Glu Met Ile Gly Asn Gln Val Gln Ser Val Lys Ile Ser Cys
    365                 370                 375

Leu
380

<210> SEQ ID NO 3
<211> LENGTH: 1188
<212> TYPE: DNA
<213> ORGANISM: Homo sapiens
<220> FEATURE:
<221> NAME/KEY: sig_peptide
<222> LOCATION: (1)..(61)
<220> FEATURE:
<221> NAME/KEY: mat_peptide
<222> LOCATION: (64)..(1185)
<220> FEATURE:
<221> NAME/KEY: CDS
<222> LOCATION: (1)..(1185)

<400> SEQUENCE: 3 atg aac aag ttg ctg tgc tgc gcg ctc gtg ttt ctg gac atc tcc att    48
Met Asn Lys Leu Leu Cys Cys Ala Leu Val Phe Leu Asp Ile Ser Ile
    -20                 -15                 -10 aag tgg acc acc cag gaa acg ttt cct cca aag tac ctt cat tat gac    96
Lys Trp Thr Thr Gln Glu Thr Phe Pro Pro Lys Tyr Leu His Tyr Asp
 -5              -1   1               5                  10 gaa gaa acc tct cat cag ctg ttg tgt gac aaa tgt cct cct ggt acc   144
Glu Glu Thr Ser His Gln Leu Leu Cys Asp Lys Cys Pro Pro Gly Thr
                15                  20                  25 tac cta aaa caa cac tgt aca gca aag tgg aag acc gtg tgc gcc cct   192
Tyr Leu Lys Gln His Cys Thr Ala Lys Trp Lys Thr Val Cys Ala Pro
            30                  35                  40 tgc cct gac cac tac tac aca gac agc tgg cac acc agt gac gag tgt   240
Cys Pro Asp His Tyr Tyr Thr Asp Ser Trp His Thr Ser Asp Glu Cys
        45                  50                  55
```

-continued

| | | |
|---|---|---|
| cta tac tgc agc ccc gtg tgc aag gag ctg cag tac gtc aag cag gag<br>Leu Tyr Cys Ser Pro Val Cys Lys Glu Leu Gln Tyr Val Lys Gln Glu<br>60                           65                    70                      75 | 288 |
| tgc aat cgc acc cac aac cgc gtg tgc gaa tgc aag gaa ggg cgc tac<br>Cys Asn Arg Thr His Asn Arg Val Cys Glu Cys Lys Glu Gly Arg Tyr<br>                    80                         85                        90 | 336 |
| ctt gag ata gag ttc tgc ttg aaa cat agg agc tgc cct cct gga ttt<br>Leu Glu Ile Glu Phe Cys Leu Lys His Arg Ser Cys Pro Pro Gly Phe<br>               95                         100                    105 | 384 |
| gga gtg gtg caa gct gga acc cca gag cga aat aca gtt tgc aaa aga<br>Gly Val Val Gln Ala Gly Thr Pro Glu Arg Asn Thr Val Cys Lys Arg<br>110                         115                    120 | 432 |
| tgt cca gat ggg ttc ttc tca aat gag acg tca tct aaa gca ccc tgt<br>Cys Pro Asp Gly Phe Phe Ser Asn Glu Thr Ser Ser Lys Ala Pro Cys<br>125                         130                    135 | 480 |
| aga aaa cac aca aat tgc agt gtc ttt ggt ctc ctg cta act cag aaa<br>Arg Lys His Thr Asn Cys Ser Val Phe Gly Leu Leu Leu Thr Gln Lys<br>140                         145                    150                    155 | 528 |
| gga aat gca aca cac gac aac ata tgt tcc gga aac agt gaa tca act<br>Gly Asn Ala Thr His Asp Asn Ile Cys Ser Gly Asn Ser Glu Ser Thr<br>                    160                        165                    170 | 576 |
| caa aaa tgt gga ata gat gtt acc ctg tgt gag gag gca ttc ttc agg<br>Gln Lys Cys Gly Ile Asp Val Thr Leu Cys Glu Glu Ala Phe Phe Arg<br>                    175                        180                    185 | 624 |
| ttt gct gtt cct aca aag ttt acg cct aac tgg ctt agt gtc ttg gta<br>Phe Ala Val Pro Thr Lys Phe Thr Pro Asn Trp Leu Ser Val Leu Val<br>                    190                        195                    200 | 672 |
| gac aat ttg cct ggc acc aaa gta aac gca gag agt gta gag agg ata<br>Asp Asn Leu Pro Gly Thr Lys Val Asn Ala Glu Ser Val Glu Arg Ile<br>205                         210                    215 | 720 |
| aaa cgg caa cac agc tca caa gaa cag act ttc cag ctg ctg aag tta<br>Lys Arg Gln His Ser Ser Gln Glu Gln Thr Phe Gln Leu Leu Lys Leu<br>220                       225                    230                    235 | 768 |
| tgg aaa cat caa aac aaa gac caa gat ata gtc aag aag atc atc caa<br>Trp Lys His Gln Asn Lys Asp Gln Asp Ile Val Lys Lys Ile Ile Gln<br>                    240                        245                    250 | 816 |
| gat att gac ctc tgt gaa aac agc gtg cag cgg cac att gga cat gct<br>Asp Ile Asp Leu Cys Glu Asn Ser Val Gln Arg His Ile Gly His Ala<br>                    255                        260                    265 | 864 |
| aac ctc acc ttc gag cag ctt cgt agc ttg atg gaa agc tta ccg gga<br>Asn Leu Thr Phe Glu Gln Leu Arg Ser Leu Met Glu Ser Leu Pro Gly<br>                    270                        275                    280 | 912 |
| aag aaa gtg gga gca gaa gac att gaa aaa aca ata aag gca tgc aaa<br>Lys Lys Val Gly Ala Glu Asp Ile Glu Lys Thr Ile Lys Ala Cys Lys<br>285                         290                    295 | 960 |
| ccc agt gac cag atc ctg aag ctg ctc agt ttg tgg cga ata aaa aat<br>Pro Ser Asp Gln Ile Leu Lys Leu Leu Ser Leu Trp Arg Ile Lys Asn<br>300                       305                    310                    315 | 1008 |
| ggc gac caa gac acc ttg aag ggc cta atg cac gca cta aag cac tca<br>Gly Asp Gln Asp Thr Leu Lys Gly Leu Met His Ala Leu Lys His Ser<br>                    320                        325                    330 | 1056 |
| aag acg tac cac ttt ccc aaa act gtc act cag agt cta aag aag acc<br>Lys Thr Tyr His Phe Pro Lys Thr Val Thr Gln Ser Leu Lys Lys Thr<br>                    335                        340                    345 | 1104 |
| atc agg ttc ctt cac agc ttc aca atg tac aaa ttg tat cag aag tta<br>Ile Arg Phe Leu His Ser Phe Thr Met Tyr Lys Leu Tyr Gln Lys Leu<br>350                         355                    360 | 1152 |
| ttt tta gaa atg ata ggt aat cta gaa aag atc taa<br>Phe Leu Glu Met Ile Gly Asn Leu Glu Lys Ile<br>365                         370 | 1188 |

<210> SEQ ID NO 4
<211> LENGTH: 395
<212> TYPE: PRT
<213> ORGANISM: Homo sapiens

<400> SEQUENCE: 4

```
Met Asn Lys Leu Leu Cys Cys Ala Leu Val Phe Leu Asp Ile Ser Ile
    -20              -15              -10
Lys Trp Thr Thr Gln Glu Thr Phe Pro Pro Lys Tyr Leu His Tyr Asp
 -5            -1   1            5                     10
Glu Glu Thr Ser His Gln Leu Leu Cys Asp Lys Cys Pro Pro Gly Thr
             15                  20                  25
Tyr Leu Lys Gln His Cys Thr Ala Lys Trp Lys Thr Val Cys Ala Pro
         30                  35                  40
Cys Pro Asp His Tyr Tyr Thr Asp Ser Trp His Thr Ser Asp Glu Cys
     45                  50                  55
Leu Tyr Cys Ser Pro Val Cys Lys Glu Leu Gln Tyr Val Lys Gln Glu
 60                  65                  70                  75
Cys Asn Arg Thr His Asn Arg Val Cys Glu Cys Lys Glu Gly Arg Tyr
             80                  85                  90
Leu Glu Ile Glu Phe Cys Leu Lys His Arg Ser Cys Pro Pro Gly Phe
         95                 100                 105
Gly Val Val Gln Ala Gly Thr Pro Glu Arg Asn Thr Val Cys Lys Arg
        110                 115                 120
Cys Pro Asp Gly Phe Phe Ser Asn Glu Thr Ser Ser Lys Ala Pro Cys
125                 130                 135
Arg Lys His Thr Asn Cys Ser Val Phe Gly Leu Leu Leu Thr Gln Lys
140                 145                 150                 155
Gly Asn Ala Thr His Asp Asn Ile Cys Ser Gly Asn Ser Glu Ser Thr
                160                 165                 170
Gln Lys Cys Gly Ile Asp Val Thr Leu Cys Glu Glu Ala Phe Phe Arg
            175                 180                 185
Phe Ala Val Pro Thr Lys Phe Thr Pro Asn Trp Leu Ser Val Leu Val
        190                 195                 200
Asp Asn Leu Pro Gly Thr Lys Val Asn Ala Glu Ser Val Glu Arg Ile
205                 210                 215
Lys Arg Gln His Ser Ser Gln Glu Gln Thr Phe Gln Leu Leu Lys Leu
220                 225                 230                 235
Trp Lys His Gln Asn Lys Asp Gln Asp Ile Val Lys Lys Ile Ile Gln
                240                 245                 250
Asp Ile Asp Leu Cys Glu Asn Ser Val Gln Arg His Ile Gly His Ala
            255                 260                 265
Asn Leu Thr Phe Glu Gln Leu Arg Ser Leu Met Glu Ser Leu Pro Gly
        270                 275                 280
Lys Lys Val Gly Ala Glu Asp Ile Glu Lys Thr Ile Lys Ala Cys Lys
285                 290                 295
Pro Ser Asp Gln Ile Leu Lys Leu Leu Ser Leu Trp Arg Ile Lys Asn
300                 305                 310                 315
Gly Asp Gln Asp Thr Leu Lys Gly Leu Met His Ala Leu Lys His Ser
                320                 325                 330
Lys Thr Tyr His Phe Pro Lys Thr Val Thr Gln Ser Leu Lys Lys Thr
            335                 340                 345
Ile Arg Phe Leu His Ser Phe Thr Met Tyr Lys Leu Tyr Gln Lys Leu
```

```
                  350                 355                 360
Phe Leu Glu Met Ile Gly Asn Leu Glu Lys Ile
    365                 370

<210> SEQ ID NO 5
<211> LENGTH: 461
<212> TYPE: PRT
<213> ORGANISM: Homo sapiens

<400> SEQUENCE: 5

Met Ala Pro Val Ala Val Trp Ala Ala Leu Ala Val Gly Leu Glu Leu
 1               5                  10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350
```

-continued

Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
            370                 375                 380

Val Asn Val Cys Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                    405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
            450                 455                 460

<210> SEQ ID NO 6
<211> LENGTH: 33
<212> TYPE: DNA
<213> ORGANISM: Homo sapiens

<400> SEQUENCE: 6
gccagaggat ccgaaacgtt tcctccaaag tac                               33

<210> SEQ ID NO 7
<211> LENGTH: 33
<212> TYPE: DNA
<213> ORGANISM: Homo sapiens

<400> SEQUENCE: 7
cggcttctag aattacctat catttctaaa aat                               33

<210> SEQ ID NO 8
<211> LENGTH: 32
<212> TYPE: DNA
<213> ORGANISM: Homo sapiens

<400> SEQUENCE: 8
cgcggatccg ccatcatgaa caagttgctg tg                                32

<210> SEQ ID NO 9
<211> LENGTH: 26
<212> TYPE: DNA
<213> ORGANISM: Homo sapiens

<400> SEQUENCE: 9
cgcggtaccc aattgtgagg aaacag                                       26

<210> SEQ ID NO 10
<211> LENGTH: 31
<212> TYPE: DNA
<213> ORGANISM: Homo sapiens

<400> SEQUENCE: 10
gcgcggatcc atgaacaagt tgctgtgctg c                                 31

<210> SEQ ID NO 11
<211> LENGTH: 34

```
<212> TYPE: DNA
<213> ORGANISM: Homo sapiens

<400> SEQUENCE: 11
gcgctctaga ttacctatca tttctaaaaa taac                           34
```